United States Patent [19]

Markvicka et al.

(10) Patent No.: US 11,484,374 B2
(45) Date of Patent: *Nov. 1, 2022

(54) LOCAL CONTROL ROBOTIC SURGICAL DEVICES AND RELATED METHODS

(71) Applicant: Board of Regents of the University of Nebraska, Lincoln, NE (US)

(72) Inventors: Eric Markvicka, Brush, CO (US); Tom Frederick, Lincoln, NE (US); Jack Mondry, Edina, MN (US); Joe Bartels, Pittsburgh, PA (US); Shane Farritor, Lincoln, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 486 days.

This patent is subject to a terminal disclaimer.

(21) Appl. No.: 16/596,034

(22) Filed: Oct. 8, 2019

(65) Prior Publication Data

US 2020/0046440 A1 Feb. 13, 2020

Related U.S. Application Data

(63) Continuation of application No. 14/656,109, filed on Mar. 12, 2015, now Pat. No. 10,470,828, which is a
(Continued)

(51) Int. Cl.
  *A61B 34/30* (2016.01)
  *A61B 90/00* (2016.01)
(Continued)

(52) U.S. Cl.
  CPC ............ *A61B 34/30* (2016.02); *A61B 90/361* (2016.02); *A61B 2017/2906* (2013.01);
(Continued)

(58) Field of Classification Search
  CPC ............ A61B 34/30; A61B 2017/2906; A61B 2034/302; Y10T 74/20317; Y10T 74/20329
  See application file for complete search history.

(56) References Cited

U.S. PATENT DOCUMENTS 3,870,264 A 3/1975 Robinson
3,989,952 A 11/1976 Timberlake et al.
(Continued)

FOREIGN PATENT DOCUMENTS

CN 102821918 12/2012
DE 102010040405 3/2012
(Continued)

OTHER PUBLICATIONS

Abbott et al., "Design of an Endoluminal NOTES Robotic System," from the Proceedings of the 2007 IEEE/RSJ Int'l Conf. on Intelligent Robot Systems, San Diego, CA, Oct. 29-Nov. 2, 2007, pp. 410-416.
(Continued)

*Primary Examiner* — Sarah A Simpson
(74) *Attorney, Agent, or Firm* — Sean Solberg

(57) ABSTRACT

The various robotic medical devices include robotic devices that are disposed within a body cavity and positioned using a support component disposed through an orifice or opening in the body cavity. Additional embodiments relate to devices having arms coupled to a device body wherein the device has a minimal profile such that the device can be easily inserted through smaller incisions in comparison to other devices without such a small profile. Further embodiments relate to methods of operating the above devices.

20 Claims, 49 Drawing Sheets

Related U.S. Application Data continuation of application No. 13/834,792, filed on Mar. 15, 2013, now Pat. No. 9,010,214.

(60) Provisional application No. 61/663,194, filed on Jun. 22, 2012.

(51) Int. Cl.
 *A61B 18/00* (2006.01)
 *A61B 17/29* (2006.01)

(52) U.S. Cl.
 CPC .......... *A61B 2018/00595* (2013.01); *A61B 2018/00982* (2013.01); *A61B 2034/302* (2016.02); *Y10T 74/20317* (2015.01); *Y10T 74/20329* (2015.01)

(56) References Cited

U.S. PATENT DOCUMENTS

| | | |
|---|---|---|
| 4,258,716 A | 3/1981 | Sutherland |
| 4,278,077 A | 7/1981 | Mizumoto |
| 4,538,594 A | 9/1985 | Boebel et al. |
| 4,568,311 A | 2/1986 | Miyaki |
| 4,736,645 A | 4/1988 | Zimmer |
| 4,771,652 A | 9/1988 | Zimmer |
| 4,852,391 A | 8/1989 | Ruch |
| 4,896,015 A | 1/1990 | Taboada et al. |
| 4,922,755 A | 5/1990 | Oshiro et al. |
| 4,922,782 A | 5/1990 | Kawai |
| 4,990,050 A | 2/1991 | Tsuge et al. |
| 5,019,968 A | 5/1991 | Wang et al. |
| 5,172,639 A | 12/1992 | Wiesman et al. |
| 5,195,388 A | 3/1993 | Zona et al. |
| 5,201,325 A | 4/1993 | McEwen et al. |
| 5,271,384 A | 12/1993 | McEwen et al. |
| 5,284,096 A | 2/1994 | Pelrine et al. |
| 5,297,443 A | 3/1994 | Wentz |
| 5,297,536 A | 3/1994 | Wilk |
| 5,304,899 A | 4/1994 | Sasaki et al. |
| 5,307,447 A | 4/1994 | Asano et al. |
| 5,353,807 A | 10/1994 | DeMarco |
| 5,363,935 A | 11/1994 | Schempf et al. |
| 5,382,885 A | 1/1995 | Salcudean et al. |
| 5,441,494 A | 1/1995 | Ortiz |
| 5,388,528 A | 2/1995 | Pelrine et al. |
| 5,436,542 A | 7/1995 | Petelin et al. |
| 5,458,131 A | 10/1995 | Wilk |
| 5,458,583 A | 10/1995 | McNeely et al. |
| 5,458,598 A | 10/1995 | Feinberg et al. |
| 5,471,515 A | 11/1995 | Fossum et al. |
| 5,515,478 A | 5/1996 | Wang |
| 5,524,180 A | 6/1996 | Wang et al. |
| 5,553,198 A | 9/1996 | Wang et al. |
| 5,562,448 A | 10/1996 | Mushabac |
| 5,588,442 A | 12/1996 | Scovil et al. |
| 5,620,417 A | 4/1997 | Jang et al. |
| 5,623,582 A | 4/1997 | Rosenberg |
| 5,624,380 A | 4/1997 | Takayama et al. |
| 5,624,398 A | 4/1997 | Smith et al. |
| 5,632,761 A | 5/1997 | Smith et al. |
| 5,645,520 A | 7/1997 | Nakamura et al. |
| 5,657,429 A | 8/1997 | Wang et al. |
| 5,657,584 A | 8/1997 | Hamlin |
| 5,672,168 A | 9/1997 | de la Torre et al. |
| 5,674,030 A | 10/1997 | Sigel |
| 5,728,599 A | 3/1998 | Rosteker et al. |
| 5,736,821 A | 4/1998 | Suyama et al. |
| 5,754,741 A | 5/1998 | Wang et al. |
| 5,762,458 A | 6/1998 | Wang et al. |
| 5,769,640 A | 6/1998 | Jacobus et al. |
| 5,791,231 A | 8/1998 | Cohn et al. |
| 5,792,135 A | 8/1998 | Madhani et al. |
| 5,797,538 A | 8/1998 | Heaton et al. |
| 5,797,900 A | 8/1998 | Madhani et al. |
| 5,807,377 A | 9/1998 | Madhani et al. |
| 5,808,665 A | 9/1998 | Green |
| 5,815,640 A | 9/1998 | Wang et al. |
| 5,825,982 A | 10/1998 | Wright et al. |
| 5,841,950 A | 11/1998 | Wang et al. |
| 5,845,646 A | 12/1998 | Lemelson |
| 5,855,583 A | 1/1999 | Wang et al. |
| 5,876,325 A | 3/1999 | Mizuno et al. |
| 5,878,193 A | 3/1999 | Wang et al. |
| 5,878,783 A | 3/1999 | Smart |
| 5,895,417 A | 4/1999 | Pomeranz et al. |
| 5,906,591 A | 5/1999 | Dario et al. |
| 5,907,664 A | 5/1999 | Wang et al. |
| 5,910,129 A | 6/1999 | Koblish et al. |
| 5,911,036 A | 6/1999 | Wright et al. |
| 5,971,976 A | 10/1999 | Wang et al. |
| 5,993,467 A | 11/1999 | Yoon |
| 6,001,108 A | 12/1999 | Wang et al. |
| 6,007,550 A | 12/1999 | Wang et al. |
| 6,030,365 A | 2/2000 | Laufer |
| 6,031,371 A | 2/2000 | Smart |
| 6,058,323 A | 5/2000 | Lemelson |
| 6,063,095 A | 5/2000 | Wang et al. |
| 6,066,090 A | 5/2000 | Yoon |
| 6,086,529 A | 7/2000 | Arndt |
| 6,102,850 A | 8/2000 | Wang et al. |
| 6,107,795 A | 8/2000 | Smart |
| 6,132,368 A | 10/2000 | Cooper |
| 6,132,441 A | 10/2000 | Grace |
| 6,139,563 A | 10/2000 | Cosgrove, III et al. |
| 6,156,006 A | 12/2000 | Brosens et al. |
| 6,159,146 A | 12/2000 | El Gazayerli |
| 6,162,171 A | 12/2000 | Ng et al. |
| D438,617 S | 3/2001 | Cooper et al. |
| 6,206,903 B1 | 3/2001 | Ramans |
| D441,076 S | 4/2001 | Cooper et al. |
| 6,223,100 B1 | 4/2001 | Green |
| D441,862 S | 5/2001 | Cooper et al. |
| 6,238,415 B1 | 5/2001 | Sepetka et al. |
| 6,240,312 B1 | 5/2001 | Alfano et al. |
| 6,241,730 B1 | 6/2001 | Alby |
| 6,244,809 B1 | 6/2001 | Wang et al. |
| 6,246,200 B1 | 6/2001 | Blumenkranz et al. |
| D444,555 S | 7/2001 | Cooper et al. |
| 6,286,514 B1 | 9/2001 | Lemelson |
| 6,296,635 B1 | 10/2001 | Smith et al. |
| 6,309,397 B1 | 10/2001 | Julian et al. |
| 6,309,403 B1 | 10/2001 | Minoret et al. |
| 6,312,435 B1 | 11/2001 | Wallace et al. |
| 6,321,106 B1 | 11/2001 | Lemelson |
| 6,327,492 B1 | 12/2001 | Lemelson |
| 6,331,181 B1 | 12/2001 | Tierney et al. |
| 6,346,072 B1 | 2/2002 | Cooper |
| 6,352,503 B1 | 3/2002 | Matsui et al. |
| 6,364,888 B1 | 4/2002 | Niemeyer et al. |
| 6,371,952 B1 | 4/2002 | Madhani et al. |
| 6,394,998 B1 | 5/2002 | Wallace et al. |
| 6,398,726 B1 | 6/2002 | Ramans et al. |
| 6,400,980 B1 | 6/2002 | Lemelson |
| 6,408,224 B1 | 6/2002 | Lemelson |
| 6,424,885 B1 | 7/2002 | Niemeyer et al. |
| 6,432,112 B2 | 8/2002 | Brock et al. |
| 6,436,107 B1 | 8/2002 | Wang et al. |
| 6,441,577 B2 | 8/2002 | Blumenkranz et al. |
| 6,450,104 B1 | 9/2002 | Grant et al. |
| 6,451,027 B1 | 9/2002 | Cooper et al. |
| 6,454,758 B1 | 9/2002 | Thompson et al. |
| 6,459,926 B1 | 10/2002 | Nowlin et al. |
| 6,463,361 B1 | 10/2002 | Wang et al. |
| 6,468,203 B2 | 10/2002 | Belson |
| 6,468,265 B1 | 10/2002 | Evans et al. |
| 6,470,236 B2 | 10/2002 | Ohtsuki |
| 6,491,691 B1 | 12/2002 | Morley et al. |
| 6,491,701 B2 | 12/2002 | Nemeyer et al. |
| 6,493,608 B1 | 12/2002 | Niemeyer et al. |
| 6,496,099 B2 | 12/2002 | Wang et al. |
| 6,497,651 B1 | 12/2002 | Kan et al. |
| 6,508,413 B2 | 1/2003 | Bauer et al. |
| 6,512,345 B2 | 1/2003 | Borenstein |
| 6,522,906 B1 | 2/2003 | Salisbury, Jr. et al. |

(56) References Cited

U.S. PATENT DOCUMENTS

| | | |
|---|---|---|
| 6,544,276 B1 | 4/2003 | Azizi |
| 6,548,982 B1 | 4/2003 | Papanikolopoulos et al. |
| 6,554,790 B1 | 4/2003 | Moll |
| 6,565,554 B1 | 5/2003 | Niemeyer |
| 6,574,355 B2 | 6/2003 | Green |
| 6,587,750 B2 | 7/2003 | Gerbi et al. |
| 6,591,239 B1 | 7/2003 | McCall et al. |
| 6,594,552 B1 | 7/2003 | Nowlin et al. |
| 6,610,007 B2 | 8/2003 | Belson et al. |
| 6,620,173 B2 | 9/2003 | Gerbi et al. |
| 6,642,836 B1 | 11/2003 | Wang et al. |
| 6,645,196 B1 | 11/2003 | Nixon et al. |
| 6,646,541 B1 | 11/2003 | Wang et al. |
| 6,648,814 B2 | 11/2003 | Kim et al. |
| 6,659,939 B2 | 12/2003 | Moll et al. |
| 6,661,571 B1 | 12/2003 | Shioda et al. |
| 6,671,581 B2 | 12/2003 | Niemeyer et al. |
| 6,676,684 B1 | 1/2004 | Morley et al. |
| 6,684,129 B2 | 1/2004 | Salisbury, Jr. et al. |
| 6,685,648 B2 | 2/2004 | Flaherty et al. |
| 6,685,698 B2 | 2/2004 | Morley et al. |
| 6,687,571 B1 | 2/2004 | Byme et al. |
| 6,692,485 B1 | 2/2004 | Brock et al. |
| 6,699,177 B1 | 3/2004 | Wang et al. |
| 6,699,235 B2 | 3/2004 | Wallace et al. |
| 6,702,734 B2 | 3/2004 | Kim et al. |
| 6,702,805 B1 | 3/2004 | Stuart |
| 6,714,839 B2 | 3/2004 | Salisbury, Jr. et al. |
| 6,714,841 B1 | 3/2004 | Wright et al. |
| 6,719,684 B2 | 4/2004 | Kim et al. |
| 6,720,988 B1 | 4/2004 | Gere et al. |
| 6,726,699 B1 | 4/2004 | Wright et al. |
| 6,728,599 B2 | 4/2004 | Wright et al. |
| 6,730,021 B2 | 5/2004 | Vassiliades, Jr. et al. |
| 6,731,988 B1 | 5/2004 | Green |
| 6,746,443 B1 | 6/2004 | Morley et al. |
| 6,764,441 B2 | 7/2004 | Chiel et al. |
| 6,764,445 B2 | 7/2004 | Ramans et al. |
| 6,766,204 B2 | 7/2004 | Niemeyer et al. |
| 6,770,081 B1 | 8/2004 | Cooper et al. |
| 6,774,597 B1 | 8/2004 | Borenstein |
| 6,776,165 B2 | 8/2004 | Jin |
| 6,780,184 B2 | 8/2004 | Fanrisever |
| 6,783,524 B2 | 8/2004 | Anderson et al. |
| 6,785,593 B2 | 8/2004 | Wang et al. |
| 6,788,018 B1 | 9/2004 | Blumenkranz |
| 6,792,663 B2 | 9/2004 | Krzyzanowski |
| 6,793,653 B2 | 9/2004 | Sanchez et al. |
| 6,799,065 B1 | 9/2004 | Niemeyer |
| 6,799,088 B2 | 9/2004 | Wang et al. |
| 6,801,325 B2 | 10/2004 | Farr et al. |
| 6,804,581 B2 | 10/2004 | Wang et al. |
| 6,810,281 B2 | 10/2004 | Brock et al. |
| 6,817,972 B2 | 11/2004 | Snow |
| 6,817,974 B2 | 11/2004 | Cooper et al. |
| 6,817,975 B1 | 11/2004 | Farr et al. |
| 6,820,653 B1 | 11/2004 | Schempf et al. |
| 6,824,508 B2 | 11/2004 | Kim et al. |
| 6,824,510 B2 | 11/2004 | Kim et al. |
| 6,832,988 B2 | 12/2004 | Sprout |
| 6,832,996 B2 | 12/2004 | Woloszko et al. |
| 6,836,703 B2 | 12/2004 | Wang et al. |
| 6,837,846 B2 | 1/2005 | Jaffe et al. |
| 6,837,883 B2 | 1/2005 | Moll et al. |
| 6,839,612 B2 | 1/2005 | Sanchez et al. |
| 6,840,938 B1 | 1/2005 | Morley et al. |
| 6,852,107 B2 | 2/2005 | Wang et al. |
| 6,858,003 B2 | 2/2005 | Evans et al. |
| 6,860,346 B2 | 3/2005 | Burt et al. |
| 6,860,877 B1 | 3/2005 | Sanchez et al. |
| 6,866,671 B2 | 3/2005 | Tiemey et al. |
| 6,870,343 B2 | 3/2005 | Borenstein et al. |
| 6,871,117 B2 | 3/2005 | Wang et al. |
| 6,871,563 B2 | 3/2005 | Choset et al. |
| 6,879,880 B2 | 4/2005 | Nowlin et al. |
| 6,892,112 B2 | 5/2005 | Wang et al. |
| 6,899,705 B2 | 5/2005 | Niemeyer |
| 6,902,560 B1 | 6/2005 | Morley et al. |
| 6,905,460 B2 | 6/2005 | Wang et al. |
| 6,905,491 B1 | 6/2005 | Wang et al. |
| 6,911,916 B1 | 6/2005 | Wang et al. |
| 6,917,176 B2 | 7/2005 | Schempf et al. |
| 6,933,695 B2 | 8/2005 | Blumenkranz |
| 6,936,001 B1 | 8/2005 | Snow |
| 6,936,003 B2 | 8/2005 | Iddan |
| 6,936,042 B2 | 8/2005 | Wallace et al. |
| 6,943,663 B2 | 9/2005 | Wang et al. |
| 6,949,096 B2 | 9/2005 | Davison et al. |
| 6,951,535 B2 | 10/2005 | Ghodoussi et al. |
| 6,965,812 B2 | 11/2005 | Wang et al. |
| 6,974,411 B2 | 12/2005 | Belson |
| 6,974,449 B2 | 12/2005 | Niemeyer |
| 6,979,423 B2 | 12/2005 | Moll |
| 6,984,203 B2 | 1/2006 | Tartaglia et al. |
| 6,984,205 B2 | 1/2006 | Gazdzinski |
| 6,991,627 B2 | 1/2006 | Madhani et al. |
| 6,993,413 B2 | 1/2006 | Sunaoshi |
| 6,994,703 B2 | 2/2006 | Wang et al. |
| 6,994,708 B2 | 2/2006 | Manzo |
| 6,997,908 B2 | 2/2006 | Carrillo, Jr. et al. |
| 7,025,064 B2 | 4/2006 | Wang et al. |
| 7,027,892 B2 | 4/2006 | Wang et al. |
| 7,033,344 B2 | 4/2006 | Imran |
| 7,039,453 B2 | 5/2006 | Mullick |
| 7,042,184 B2 | 5/2006 | Oleynikov et al. |
| 7,048,745 B2 | 5/2006 | Tierney et al. |
| 7,053,752 B2 | 5/2006 | Wang et al. |
| 7,063,682 B1 | 6/2006 | Whayne et al. |
| 7,066,879 B2 | 6/2006 | Fowler et al. |
| 7,066,926 B2 | 6/2006 | Wallace et al. |
| 7,074,179 B2 | 7/2006 | Wang et al. |
| 7,077,446 B2 | 7/2006 | Kameda et al. |
| 7,083,571 B2 | 8/2006 | Wang et al. |
| 7,083,615 B2 | 8/2006 | Peterson et al. |
| 7,087,049 B2 | 8/2006 | Nowlin et al. |
| 7,090,683 B2 | 8/2006 | Brock et al. |
| 7,097,640 B2 | 8/2006 | Wang et al. |
| 7,105,000 B2 | 9/2006 | McBrayer |
| 7,107,090 B2 | 9/2006 | Salisbury, Jr. et al. |
| 7,109,678 B2 | 9/2006 | Kraus et al. |
| 7,118,582 B1 | 10/2006 | Wang et al. |
| 7,121,781 B2 | 10/2006 | Sanchez et al. |
| 7,125,403 B2 | 10/2006 | Julian et al. |
| 7,126,303 B2 | 10/2006 | Farritor et al. |
| 7,147,650 B2 | 12/2006 | Lee |
| 7,155,315 B2 | 12/2006 | Niemeyer et al. |
| 7,169,141 B2 | 1/2007 | Brock et al. |
| 7,182,025 B2 | 2/2007 | Ghorbel et al. |
| 7,182,089 B2 | 2/2007 | Ries |
| 7,199,545 B2 | 4/2007 | Oleynikov et al. |
| 7,206,626 B2 | 4/2007 | Quaid, III |
| 7,206,627 B2 | 4/2007 | Abovitz et al. |
| 7,210,364 B2 | 5/2007 | Ghorbel et al. |
| 7,214,230 B2 | 5/2007 | Brock et al. |
| 7,217,240 B2 | 5/2007 | Snow |
| 7,239,940 B2 | 7/2007 | Wang et al. |
| 7,250,028 B2 | 7/2007 | Julian et al. |
| 7,259,652 B2 | 8/2007 | Wang et al. |
| 7,273,488 B2 | 9/2007 | Nakamura et al. |
| 7,311,107 B2 | 12/2007 | Harel et al. |
| 7,339,341 B2 | 3/2008 | Oleynikov et al. |
| 7,372,229 B2 | 5/2008 | Farritor et al. |
| 7,447,537 B1 | 11/2008 | Funda et al. |
| 7,492,116 B2 | 2/2009 | Oleynikov et al. |
| 7,566,300 B2 | 7/2009 | Devierre et al. |
| 7,574,250 B2 | 8/2009 | Niemeyer |
| 7,637,905 B2 | 12/2009 | Saadat et al. |
| 7,645,230 B2 | 1/2010 | Mikkaichi et al. |
| 7,655,004 B2 | 2/2010 | Long |
| 7,670,329 B2 | 3/2010 | Flaherty et al. |
| 7,731,727 B2 | 6/2010 | Sauer |
| 7,762,825 B2 | 7/2010 | Burbank et al. |
| 7,772,796 B2 | 8/2010 | Farritor et al. |
| 7,785,251 B2 | 8/2010 | Wilk |

(56) References Cited

U.S. PATENT DOCUMENTS

| | | |
|---|---|---|
| 7,785,333 B2 | 8/2010 | Miyamoto et al. |
| 7,789,825 B2 | 9/2010 | Nobis et al. |
| 7,794,494 B2 | 9/2010 | Sahatjian et al. |
| 7,865,266 B2 | 1/2011 | Moll et al. |
| 7,960,935 B2 | 6/2011 | Farritor et al. |
| 3,021,358 A1 | 9/2011 | Doyle et al. |
| 8,231,610 B2 | 7/2012 | Jo et al. |
| 8,353,897 B2 | 1/2013 | Doyle et al. |
| 9,089,353 B2 | 7/2015 | Farritor et al. |
| 9,649,020 B2 | 5/2017 | Finlay |
| 10,470,828 B2 * | 11/2019 | Markvicka ............. A61B 34/30 |
| 2001/0018591 A1 | 8/2001 | Brock et al. |
| 2001/0049497 A1 | 12/2001 | Kalloo et al. |
| 2002/0003173 A1 | 1/2002 | Bauer et al. |
| 2002/0013601 A1 | 1/2002 | Nobles et al. |
| 2002/0026186 A1 | 2/2002 | Woloszko et al. |
| 2002/0038077 A1 | 3/2002 | de la Torre et al. |
| 2002/0065507 A1 | 5/2002 | Zando-Azizi |
| 2002/0091374 A1 | 6/2002 | Cooper |
| 2002/0103417 A1 | 8/2002 | Gazdzinski |
| 2002/0111535 A1 | 8/2002 | Kim et al. |
| 2002/0120254 A1 | 8/2002 | Julian et al. |
| 2002/0128552 A1 | 9/2002 | Nowlin et al. |
| 2002/0140392 A1 | 10/2002 | Borenstein et al. |
| 2002/0147487 A1 | 10/2002 | Sundquist et al. |
| 2002/0151906 A1 | 10/2002 | Demarais et al. |
| 2002/0156347 A1 | 10/2002 | Kim et al. |
| 2002/0171385 A1 | 11/2002 | Kim et al. |
| 2002/0173700 A1 | 11/2002 | Kim et al. |
| 2002/0190682 A1 | 12/2002 | Schempf et al. |
| 2003/0020810 A1 | 1/2003 | Takizawa et al. |
| 2003/0045888 A1 | 3/2003 | Brock et al. |
| 2003/0065250 A1 | 4/2003 | Chiel et al. |
| 2003/0089267 A1 | 5/2003 | Ghorbel et al. |
| 2003/0092964 A1 | 5/2003 | Kim et al. |
| 2003/0097129 A1 | 5/2003 | Davison et al. |
| 2003/0100817 A1 | 5/2003 | Wang et al. |
| 2003/0114731 A1 | 6/2003 | Cadeddu et al. |
| 2003/0135203 A1 | 6/2003 | Wang et al. |
| 2003/0139742 A1 | 7/2003 | Wampler et al. |
| 2003/0144656 A1 | 7/2003 | Deel et al. |
| 2003/0167000 A1 | 9/2003 | Mullick |
| 2003/0172871 A1 | 9/2003 | Scherer |
| 2003/0179308 A1 | 9/2003 | Zamorano et al. |
| 2003/0181788 A1 | 9/2003 | Kokoi et al. |
| 2003/0229268 A1 | 12/2003 | Uchiyama et al. |
| 2003/0229338 A1 | 12/2003 | Irion et al. |
| 2003/0230372 A1 | 12/2003 | Schmidt |
| 2004/0024311 A1 | 2/2004 | Quaid |
| 2004/0034282 A1 | 2/2004 | Quaid |
| 2004/0034283 A1 | 2/2004 | Quaid |
| 2004/0034302 A1 | 2/2004 | Abovitz et al. |
| 2004/0050394 A1 | 3/2004 | Jin |
| 2004/0070822 A1 | 4/2004 | Shioda et al. |
| 2004/0099175 A1 | 5/2004 | Perrot et al. |
| 2004/0102772 A1 | 5/2004 | Baxter et al. |
| 2004/0106916 A1 | 6/2004 | Quaid et al. |
| 2004/0111113 A1 | 6/2004 | Nakamura et al. |
| 2004/0117032 A1 | 6/2004 | Roth |
| 2004/0138525 A1 | 7/2004 | Saadat et al. |
| 2004/0138552 A1 | 7/2004 | Harel et al. |
| 2004/0140786 A1 | 7/2004 | Borenstein |
| 2004/0153057 A1 | 8/2004 | Davison |
| 2004/0173116 A1 | 9/2004 | Ghorbel et al. |
| 2004/0176664 A1 | 9/2004 | Iddan |
| 2004/0215331 A1 | 10/2004 | Chew et al. |
| 2004/0225229 A1 | 11/2004 | Viola |
| 2004/0254680 A1 | 12/2004 | Sunaoshi |
| 2004/0267326 A1 | 12/2004 | Ocel et al. |
| 2005/0014994 A1 | 1/2005 | Fowler et al. |
| 2005/0021069 A1 | 1/2005 | Feuer et al. |
| 2005/0029978 A1 | 2/2005 | Oleynikov et al. |
| 2005/0043583 A1 | 2/2005 | Killmann et al. |
| 2005/0049462 A1 | 3/2005 | Kanazawa |
| 2005/0054901 A1 | 3/2005 | Koshino |
| 2005/0054902 A1 | 3/2005 | Konno |
| 2005/0064378 A1 | 3/2005 | Toly |
| 2005/0065400 A1 | 3/2005 | Banik et al. |
| 2005/0083460 A1 | 4/2005 | Hattori et al. |
| 2005/0095650 A1 | 5/2005 | Julius et al. |
| 2005/0096502 A1 | 5/2005 | Khalili |
| 2005/0143644 A1 | 6/2005 | Gilad et al. |
| 2005/0154376 A1 | 7/2005 | Riviere et al. |
| 2005/0165449 A1 | 7/2005 | Cadeddu et al. |
| 2005/0234435 A1 | 10/2005 | Layer |
| 2005/0283137 A1 | 12/2005 | Doyle et al. |
| 2005/0288555 A1 | 12/2005 | Binmoeller |
| 2005/0288665 A1 | 12/2005 | Woloszko |
| 2006/0020272 A1 | 1/2006 | Gildenberg |
| 2006/0046226 A1 | 3/2006 | Bergler et al. |
| 2006/0100501 A1 | 5/2006 | Berkelman et al. |
| 2006/0119304 A1 | 6/2006 | Farritor et al. |
| 2006/0149135 A1 | 7/2006 | Paz |
| 2006/0152591 A1 | 7/2006 | Lin |
| 2006/0155263 A1 | 7/2006 | Lipow |
| 2006/0195015 A1 | 8/2006 | Mullick et al. |
| 2006/0196301 A1 | 9/2006 | Oleynikov et al. |
| 2006/0198619 A1 | 9/2006 | Oleynikov et al. |
| 2006/0241570 A1 | 10/2006 | Wilk |
| 2006/0241732 A1 | 10/2006 | Denker |
| 2006/0253109 A1 | 11/2006 | Chu |
| 2006/0258954 A1 | 11/2006 | Timberlake et al. |
| 2007/0032701 A1 | 2/2007 | Fowler et al. |
| 2007/0043397 A1 | 2/2007 | Ocel et al. |
| 2007/0055342 A1 | 3/2007 | Wu et al. |
| 2007/0080658 A1 | 4/2007 | Farritor et al. |
| 2007/0106113 A1 | 5/2007 | Ravo |
| 2007/0123748 A1 | 5/2007 | Meglan |
| 2007/0135803 A1 | 6/2007 | Belson |
| 2007/0142725 A1 | 6/2007 | Hardin et al. |
| 2007/0156019 A1 | 7/2007 | Larkin et al. |
| 2007/0156211 A1 | 7/2007 | Ferren et al. |
| 2007/0167955 A1 | 7/2007 | De La Menardiere et al. |
| 2007/0225633 A1 | 9/2007 | Ferren et al. |
| 2007/0225634 A1 | 9/2007 | Ferren et al. |
| 2007/0241714 A1 | 10/2007 | Oleynikov et al. |
| 2007/0244520 A1 | 10/2007 | Ferren et al. |
| 2007/0250064 A1 | 10/2007 | Darois et al. |
| 2007/0255273 A1 | 11/2007 | Fernandez et al. |
| 2008/0004634 A1 * | 1/2008 | Farritor .................. A61B 18/00 901/1 |
| 2008/0015565 A1 | 1/2008 | Davison |
| 2008/0015566 A1 | 1/2008 | Livneh |
| 2008/0033569 A1 | 2/2008 | Ferren et al. |
| 2008/0045803 A1 | 2/2008 | Williams et al. |
| 2008/0058835 A1 | 3/2008 | Farritor et al. |
| 2008/0058989 A1 | 3/2008 | Oleynikov et al. |
| 2008/0103440 A1 | 5/2008 | Ferren et al. |
| 2008/0109014 A1 | 5/2008 | de la Pena |
| 2008/0111513 A1 | 5/2008 | Farritor et al. |
| 2008/0119870 A1 | 5/2008 | Williams et al. |
| 2008/0132890 A1 | 6/2008 | Woloszko et al. |
| 2008/0161804 A1 | 6/2008 | Rioux et al. |
| 2008/0164079 A1 | 7/2008 | Ferren et al. |
| 2008/0183033 A1 | 7/2008 | Bern et al. |
| 2008/0221591 A1 | 9/2008 | Farritor et al. |
| 2008/0269557 A1 | 10/2008 | Marescaux et al. |
| 2008/0269562 A1 | 10/2008 | Marescaux et al. |
| 2009/0012532 A1 | 1/2009 | Quaid et al. |
| 2009/0020724 A1 | 1/2009 | Paffrath |
| 2009/0024142 A1 | 1/2009 | Ruiz Morales |
| 2009/0048612 A1 | 2/2009 | Farritor et al. |
| 2009/0054909 A1 | 2/2009 | Farritor et al. |
| 2009/0069821 A1 | 3/2009 | Farritor et al. |
| 2009/0076536 A1 | 3/2009 | Rentschler et al. |
| 2009/0137952 A1 | 5/2009 | Ramamurthy et al. |
| 2009/0143787 A9 | 6/2009 | De La Pena |
| 2009/0163929 A1 | 6/2009 | Yeung et al. |
| 2009/0171373 A1 | 7/2009 | Farritor et al. |
| 2009/0234369 A1 | 9/2009 | Bax et al. |
| 2009/0236400 A1 | 9/2009 | Cole et al. |
| 2009/0240246 A1 | 9/2009 | Devill et al. |
| 2009/0247821 A1 | 10/2009 | Rogers |
| 2009/0248038 A1 | 10/2009 | Blumenkranz et al. |

(56) References Cited

U.S. PATENT DOCUMENTS

| | | |
|---|---|---|
| 2009/0281377 A1 | 11/2009 | Newell et al. |
| 2009/0305210 A1 | 12/2009 | Guru et al. |
| 2010/0010294 A1 | 1/2010 | Conlon et al. |
| 2010/0016659 A1 | 1/2010 | Weitzner et al. |
| 2010/0016853 A1 | 1/2010 | Burbank |
| 2010/0042097 A1 | 2/2010 | Newton et al. |
| 2010/0056863 A1 | 3/2010 | Dejima et al. |
| 2010/0069710 A1 | 3/2010 | Yamatani et al. |
| 2010/0069940 A1 | 3/2010 | Miller et al. |
| 2010/0081875 A1 | 4/2010 | Fowler et al. |
| 2010/0139436 A1 | 6/2010 | Kawashima et al. |
| 2010/0185212 A1 | 7/2010 | Sholev |
| 2010/0198231 A1 | 8/2010 | Manzo et al. |
| 2010/0204713 A1 | 8/2010 | Ruiz Morales |
| 2010/0245549 A1 | 9/2010 | Allen et al. |
| 2010/0262162 A1 | 10/2010 | Omori |
| 2010/0292691 A1 | 11/2010 | Brogna |
| 2010/0318059 A1 | 12/2010 | Farritor et al. |
| 2011/0020779 A1 | 1/2011 | Hannaford et al. |
| 2011/0071347 A1 | 3/2011 | Rogers et al. |
| 2011/0071544 A1 | 3/2011 | Steger et al. |
| 2011/0077478 A1 | 3/2011 | Freeman et al. |
| 2011/0098529 A1 | 4/2011 | Ostrovsky et al. |
| 2011/0224605 A1 | 9/2011 | Farritor et al. |
| 2011/0230894 A1 | 9/2011 | Simaan et al. |
| 2011/0237890 A1 | 9/2011 | Farritor et al. |
| 2011/0238080 A1 | 9/2011 | Ranjit et al. |
| 2011/0264078 A1 | 10/2011 | Lipow et al. |
| 2011/0270443 A1 | 11/2011 | Kamiya et al. |
| 2011/0276046 A1 | 11/2011 | Heimbecker et al. |
| 2012/0029727 A1 | 2/2012 | Sholev |
| 2012/0035582 A1 | 2/2012 | Nelson et al. |
| 2012/0109150 A1 | 5/2012 | Quaid et al. |
| 2012/0116362 A1 | 5/2012 | Kieturakis |
| 2012/0179168 A1 | 7/2012 | Farritor et al. |
| 2012/0253515 A1 | 10/2012 | Coste-Maniere et al. |
| 2013/0131695 A1* | 5/2013 | Scarfogliero .......... A61B 34/30 606/130 |
| 2013/0345717 A1 | 12/2013 | Markvicka et al. |
| 2014/0039515 A1 | 2/2014 | Mondry et al. |
| 2014/0046340 A1 | 2/2014 | Wilson et al. |
| 2014/0058205 A1 | 2/2014 | Frederick et al. |
| 2014/0303434 A1 | 10/2014 | Farritor et al. |
| 2015/0051446 A1 | 2/2015 | Farritor et al. |

FOREIGN PATENT DOCUMENTS

| | | |
|---|---|---|
| EP | 1354670 | 10/2003 |
| EP | 1354670 A1 | 10/2003 |
| EP | 2286756 | 2/2011 |
| EP | 2286756 A1 | 2/2011 |
| EP | 2329787 | 6/2011 |
| EP | 2563261 | 3/2013 |
| JP | 05-115425 | 5/1993 |
| JP | 2006508049 | 9/1994 |
| JP | 07-016235 | 1/1995 |
| JP | 07-136173 | 5/1995 |
| JP | 7306155 | 11/1995 |
| JP | 08-224248 | 9/1996 |
| JP | 2001500510 | 1/2001 |
| JP | 2001505810 | 5/2001 |
| JP | 2003220065 | 8/2003 |
| JP | 2004144533 | 5/2004 |
| JP | 2004-180781 | 7/2004 |
| JP | 2004322310 | 11/2004 |
| JP | 2004329292 | 11/2004 |
| JP | 2006507809 | 3/2006 |
| JP | 2009106606 | 5/2009 |
| JP | 2010533045 | 10/2010 |
| JP | 2010536436 | 12/2010 |
| JP | 2011504794 | 2/2011 |
| JP | 2011045500 | 3/2011 |
| JP | 2011115591 | 6/2011 |
| WO | 199221291 | 5/1991 |
| WO | 2001089405 | 11/2001 |
| WO | 2002082979 | 10/2002 |
| WO | 2002100256 | 12/2002 |
| WO | 2005009211 | 7/2004 |
| WO | 2005044095 | 5/2005 |
| WO | 2006052927 | 8/2005 |
| WO | 2006005075 | 1/2006 |
| WO | 2006079108 | 1/2006 |
| WO | 2006079108 | 7/2006 |
| WO | 2007011654 | 1/2007 |
| WO | 2007111571 | 10/2007 |
| WO | 2007149559 | 12/2007 |
| WO | 2009023851 | 2/2009 |
| WO | 2009144729 | 12/2009 |
| WO | 2010050771 | 5/2010 |
| WO | 2011075693 | 6/2011 |
| WO | 2011118646 | 9/2011 |
| WO | 2011118646 A1 | 9/2011 |
| WO | 2011135503 | 11/2011 |
| WO | WO-2011135503 A1 * | 11/2011 ......... A61B 19/2203 |
| WO | 2013009887 | 1/2013 |
| WO | 2014011238 | 1/2014 |

OTHER PUBLICATIONS

Allendorf et al., "Postoperative Immune Function Varies Inversely with the Degree of Surgical Trauma in a Murine Model," Surgical Endoscopy 1997; 11:427-430.

Ang, "Active Tremor Compensation in Handheld Instrument for Microsurgery," Doctoral Dissertation, tech report CMU-RI-TR-04-28, Robotics Institute, Carnegie Mellon Unviersity, May 2004, 167pp.

Atmel 80C5X2 Core, http://www.atmel.com, 2006, 186pp.

Bailey et al., "Complications of Laparoscopic Surgery," Quality Medical Publishers, Inc., 1995, 25pp.

Ballantyne, "Robotic Surgery, Telerobotic Surgery, Telepresence, and Telementoring," Surgical Endoscopy, 2002 16: 1389-1402.

Bauer et al., "Case Report: Remote Percutaneous Renal Percutaneous Renal Access Using a New Automated Telesurgical Robotic System," Telemedicine Journal and e-Health 2001; (4): 341-347.

Begos et al., "Laparoscopic Cholecystectomy: From Gimmick to Gold Standard," J Clin Gastroenterol, 1994; 19(4):325-330.

Berg et al., "Surgery with Cooperative Robots," Medicine Meets Virtual Reality, Feb. 2007, 1 pg.

Breda et al., "Future developments and perspectives in laparoscopy," Eur. Urology 2001; 40(1): 84-91.

Breedveld et al., "Design of Steerable Endoscopes to Improve the Visual Perception of Depth During Laparoscopic Surgery," ASME, Jan. 2004; vol. 126, pp. 1-5.

Breedveld et al., "Locomotion through the Intestine by means of Rolling Stents," Proceedings of the ASME Design Engineering Technical Conferences, 2004, pp. 1-7.

Calafiore et al., Multiple Arterial Conduits Without Cardiopulmonary Bypass: Early Angiographic Results,: Ann Thorac Surg, 1999; 67: 450-456.

Camarillo et al., "Robotic Technology in Surgery: Past, Present and Future," The American Journal of Surgery, 2004; 188: 2S-15.

Cavusoglu et al., "Telesurgery and Surgical Simulation: Haptic Interfaces to Real and Virtual Surgical Environments," In McLaughliin, M.L., Hespanha, J.P., and Sukhatme, G., editors. Touch in virtual environments, IMSC Series in Multimedia 2001, 28pp.

Dumpert et al., "Stereoscopic In Vivo Surgical Robots," IEEE Sensors Special Issue on In Vivo Sensors for Medicine, Jan. 2007, 10 pp.

Green, "Telepresence Surgery", Jan. 1, 1995, Publisher: IEEE Engineering in Medicine and Biology.

Cleary et al., "State of the Art in Surgical Rooties: Clinical Applications and Technology Challenges", "Computer Aided Surgery", Jan. 1, 2002, pp. 312-328, vol. 6.

Stoianovici et al., "Robotic Tools for Minimally Invasive Urologic Surgery", Jan. 1, 2002, pp. 1-17.

Franzino, "The Laprotek Surgical System and the Next Generation of Robotics," Surg Clin North Am, 2003 83(6): 1317-1320.

(56) References Cited

OTHER PUBLICATIONS

Franklin et al.," Prospective Comparison of Open vs. Laparoscopic Colon Surgery for Carcinoma: Five-Year Results," Dis Colon Rectum, 1996; 39: S35-S46.

Flynn et al., "Tomorrow's surgery: micromotors and microrobots for minimally invasive procedures," Minimally Invasive Surgery & Allied Technologies, 1998; 7(4): 343-352.

Fireman et al., "Diagnosing small bowel Crohn's desease with wireless capsule endoscopy," Gut 2003; 52: 390-392.

Fearing et al., "Wing Transmission for a Micromechanical Flying Insect," Proceedings of the 2000 IEEE International Conference to Robotics & Automation, Apr. 2000; 1509-1516.

Faraz et al., "Engineering Approaches to Mechanical and Robotic Design for Minimaly Invasive Surgery (MIS)," Kluwer Academic Publishers (Boston), 2000, 13pp.

Falcone et al., "Robotic Surgery," Clin. Obstet. Gynecol. 2003, 46(1): 37-13.

Fraulob et al., "Miniature assistance module for robot-assisted heart surgery," Biomed. Tech. 2002, 47 Suppl. 1, Pt. 1: 12-15.

Fukuda et al., "Mechanism and Swimming Experiment of Micro Mobile Robot in Water," Proceedings of the 1994 IEEE International Conference on Robotics and Automation, 1994: 814-819.

Fukuda et al., "Micro Active Catheter System with Multi Degrees of Freedom," Proceedings of the IEEE International Conference on Robotics and Automation, May 1994, pp. 2290-2295.

Fuller et al., "Laparoscopic Trocar Injuries: A Report from a U.S. Food and Drug Administration (FDA) Center for Devices and Radiological Health (CDRH) Systematic Technology Assessment of Medical Products (STAMP) Committe," U.S. Food and Drug Adminstration, available at http://www.fdaJ:?;ov, Finalized: Nov. 7, 2003; Updated: Jun. 24, 2005, 11 pp.

Dumpert et al., "Improving in Vivo Robot Visioin Quality," from the Proceedings of Medicine Meets Virtual Realtiy, Long Beach, CA, Jan. 26-29, 2005. 1 pg.

Dakin et al., "Comparison of laparoscopic skills performance between standard instruments and two surgical robotic systems," Surg Endosc., 2003; 17: 574-579.

Cuschieri, "Technology for Minimal Access Surgery," BMJ, 1999, 319: 1-6.

Grady, "Doctors Try New Surgery for Gallbladder Removal," The New York Times, Apr. 20, 2007, 3 pp.

Choi et al., "Flexure-based Manipulator for Active Handheld Microsurgical Instrument," Proceedings of the 27th Annual International Conference of the IEEE Engineering in Medicine and Biology Society (EMBS), Sep. 2005, 4pp.

Chanthasopeephan et al., (2003), "Measuring Forces in Liver Cutting: New Equipment and Experimenal Results," Annals of Biomedical Engineering 31:1372-1382.

Cavusoglu et al.,"Robotics for Telesurgery: Second Generation Berkeley/UCSF Laparoscopic Telesurgical Workstation and Looking Towards the Future Applications," Industrial Robot: An International Journal, 2003; 30(1): 22-29.

Guber et al., "Miniaturized Instrument Systems for Minimally Invasive Diagnosis and Therapy," Biomedizinische Technic. 2002, Band 47, Erganmngsband 1: 198-201.

\* cited by examiner

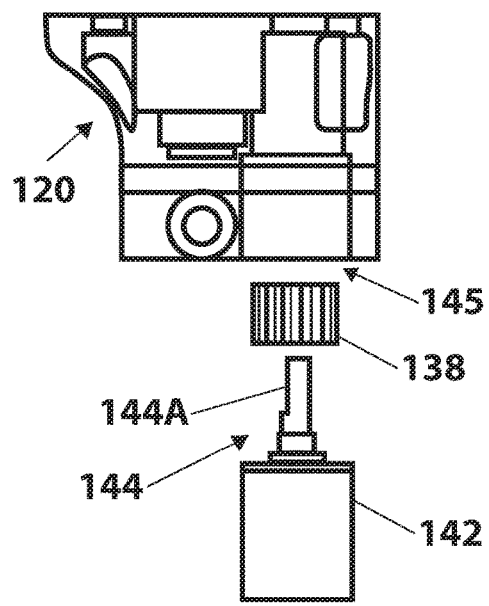
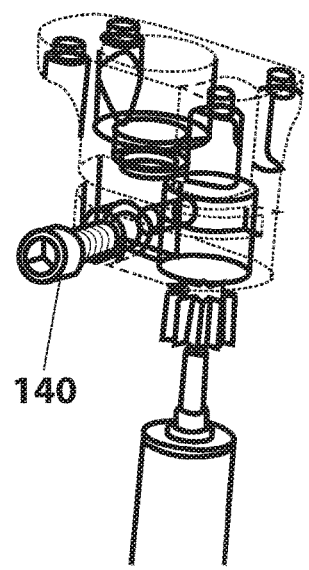
Figure 13A
Figure 13B
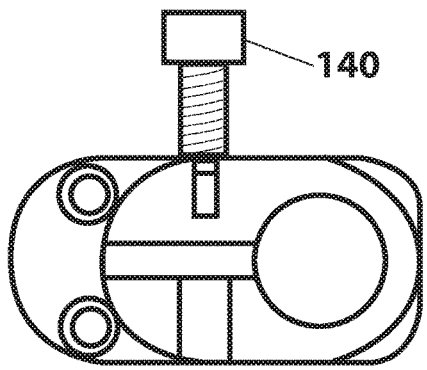
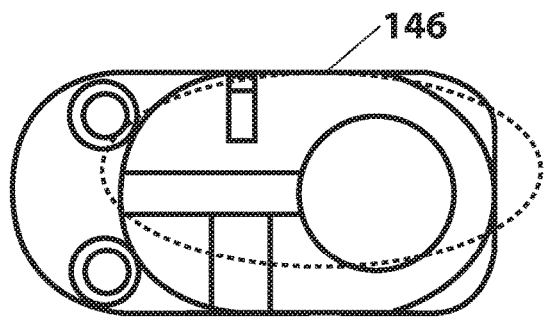
Figure 13C
Figure 13D
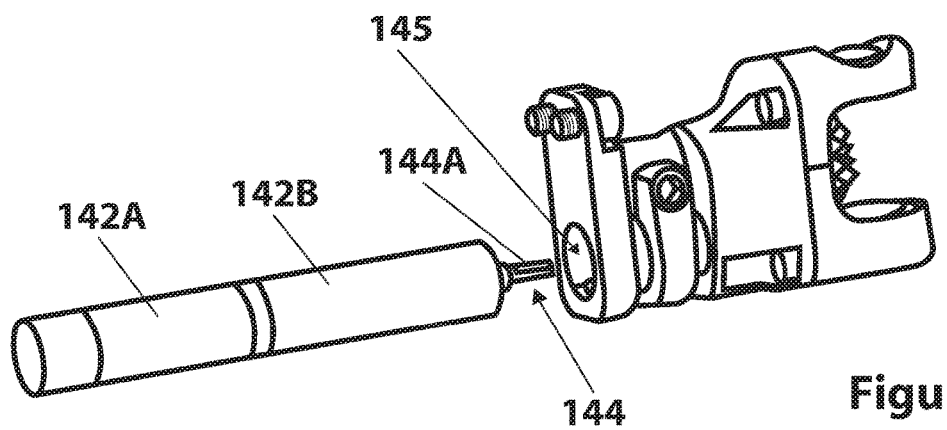
Figure 13E

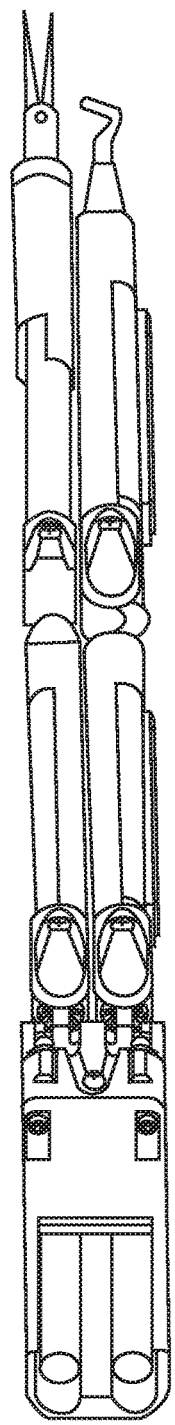
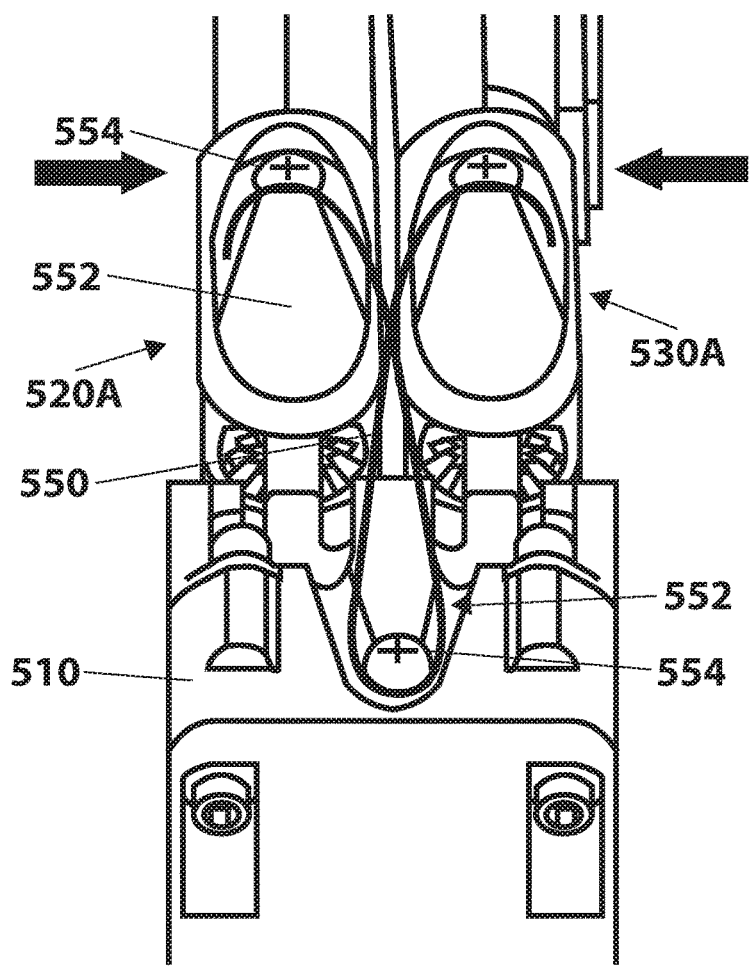
Figure 31A
Figure 31B

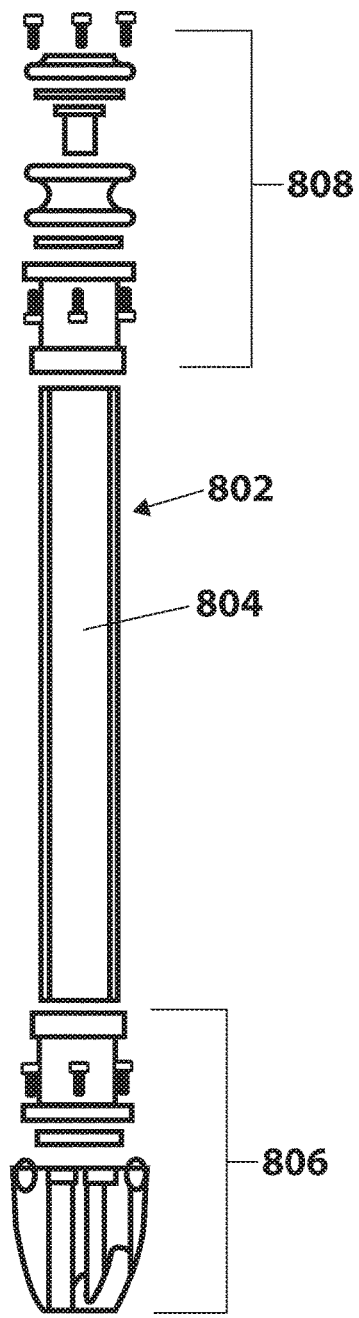
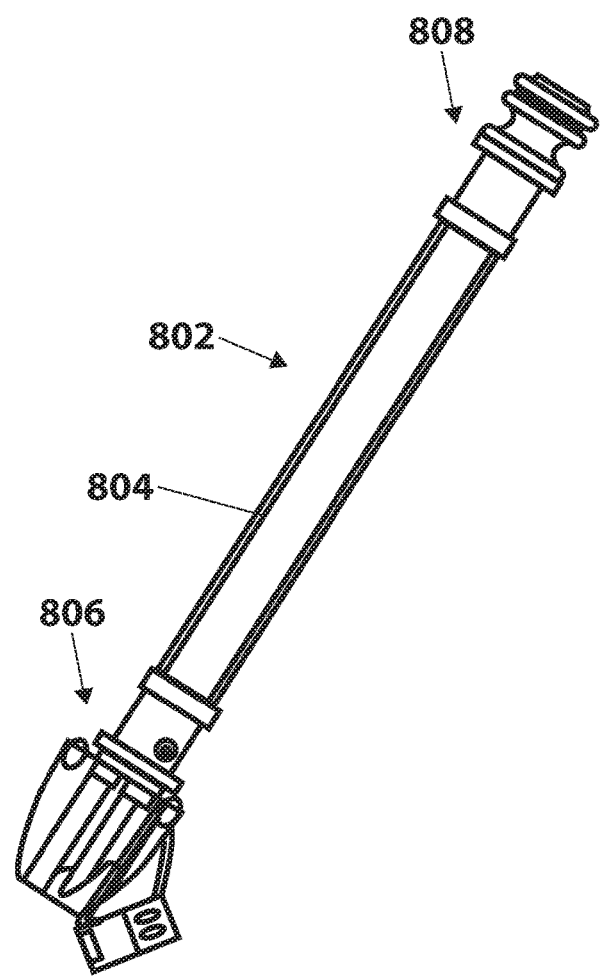
Figure 41A
Figure 41B

LOCAL CONTROL ROBOTIC SURGICAL DEVICES AND RELATED METHODS

CROSS-REFERENCE TO RELATED APPLICATION(S)

This application claims priority as a continuation application to U.S. application Ser. No. 14/656,109, filed Mar. 12, 2015, and entitled "Local Control Robotic Surgical Devices and Related Methods," which claims priority as a continuation application to U.S. application Ser. No. 13/834,792, filed Mar. 15, 2013, and entitled "Local Control Robotic Surgical Devices and Related Methods," which issued as U.S. Pat. No. 9,010,214 on Apr. 21, 2015, which claims the benefit under 35 U.S.C. § 119(e) to U.S. Patent Application 61,663,194, filed on Jun. 22, 2012, all of which are hereby incorporated herein by reference in their entireties.

GOVERNMENT SUPPORT

This invention was made with government support under Grant No. NNX09AO71A and NNX10AJ26G awarded by the National Aeronautics and Space Administration and Grant No. W81XWH-09-2-0185 awarded by U.S. Army Medical Research and Materiel Command within the Department of Defense. The government has certain rights in the invention.

FIELD OF THE INVENTION

The embodiments disclosed herein relate to various medical devices and related components, including robotic and/or in vivo medical devices and related components. Certain embodiments include various robotic medical devices, including robotic devices that are disposed within a body cavity and positioned using a support component disposed through an orifice or opening in the body cavity. Further embodiment relate to methods of operating the above devices.

BACKGROUND OF THE INVENTION

Invasive surgical procedures are essential for addressing various medical conditions. When possible, minimally invasive procedures such as laparoscopy are preferred.

However, known minimally invasive technologies such as laparoscopy are limited in scope and complexity due in part to 1) mobility restrictions resulting from using rigid tools inserted through access ports, and 2) limited visual feedback. Known robotic systems such as the da Vinci® Surgical System (available from Intuitive Surgical, Inc., located in Sunnyvale, Calif.) are also restricted by the access ports, as well as having the additional disadvantages of being very large, very expensive, unavailable in most hospitals, and having limited sensory and mobility capabilities.

There is a need in the art for improved surgical methods, systems, and devices.

BRIEF SUMMARY OF THE INVENTION

Discussed herein are various embodiments relating to robotic surgical devices, including robotic devices configured to be disposed within a cavity of a patient and positioned using a support or positioning component disposed through an orifice or opening in the cavity.

In Example 1, a robotic device comprises a device body, a first arm, and a second arm. The device body has a motor housing and a gear housing. The motor housing comprises a first motor and a second motor. The gear housing has a first gear positioned at a distal end of the gear housing, the first gear operably coupled to the first motor, and a second gear positioned at a distal end of the gear housing, the second gear operably coupled to the second motor. The first arm is operably coupled to the first gear and positioned substantially within a longitudinal cross-section of the device body when the first arm is extended in a straight configuration. The second arm is operably coupled to the second gear and positioned substantially within the longitudinal cross-section of the device body when the second arm is extended in a straight configuration.

Example 2 relates to the robotic device according to Example 1, wherein the gear housing comprises first, second, and third housing protrusions disposed at the distal end of the gear housing, wherein the first gear is disposed between the first and second housing protrusions and the second gear is disposed between the second and third housing protrusions.

In Example 3, a robotic device comprises a device body, a first arm, and a second arm. The device body has a first gear and a second gear. The first gear is positioned at a distal end of the device body and configured to rotate around a first axis parallel to a length of the device body. The second gear is positioned at the distal end of the device body and configured to rotate around a second axis parallel to the length of the device body. The first arm is operably coupled to the first gear at a first shoulder joint, wherein the first shoulder joint is positioned substantially within a longitudinal cross-section of the device body. The second arm is operably coupled to the second gear at a second shoulder joint, wherein the second shoulder joint is positioned substantially within the longitudinal cross-section of the device body.

In Example 4, a robotic device comprises a device body, a first arm, and a second arm. The device body has a motor housing and a gear housing. The motor housing has a first motor and a second motor. The gear housing has a first gear and a second gear. The first gear is positioned at a distal end of the gear housing, is operably coupled to the first motor, and is positioned to rotate around a first axis parallel to a length of the device body. The second gear is positioned at a distal end of the gear housing, is operably coupled to the second motor, and is positioned to rotate around a second axis parallel to a length of the device body. The first arm is operably coupled to the first gear and has a first upper arm and a first forearm. The first arm is positioned substantially within a longitudinal cross-section of the device body when the first arm is extended in a straight configuration such that the first upper arm and the first forearm are collinear. The second arm is operably coupled to the second gear and has a second upper arm and a second forearm. The second arm is positioned substantially within the longitudinal cross-section of the device body when the second arm is extended in a straight configuration such that the second upper arm and the second forearm are collinear.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

BRIEF DESCRIPTION OF THE DRAWINGS

FIG. 13A is a side view of a portion of an upper arm, according to one embodiment.

FIG. 13B is a perspective view of the portion of the upper arm in FIG. 13A.

FIG. 13C is a cross-section view of the portion of the upper arm in FIG. 13A.

FIG. 13D is a cross-section view of the portion of the upper arm in FIG. 13A.

FIG. 13E is a different perspective view of the portion of the upper arm in FIG. 13A.

FIG. 31A is a top view of the medical device of FIG. 30.

FIG. 31B is an expanded top view of a portion of the device in FIG. 31A.

FIG. 40B-2 is a perspective view of the access and insertion device of FIG. 40B-1 in use.

FIG. 40B-3 is a perspective view of the access and insertion device of FIG. 40B-1 in use.

FIG. 40B-4 is a perspective view of the access and insertion device of FIG. 40B-1 in use.

FIG. 41A is a side view of an access and insertion device, according to one embodiment.

FIG. 41B is a perspective view of the access and insertion device of FIG. 41A.

DETAILED DESCRIPTION

Figure 1A:
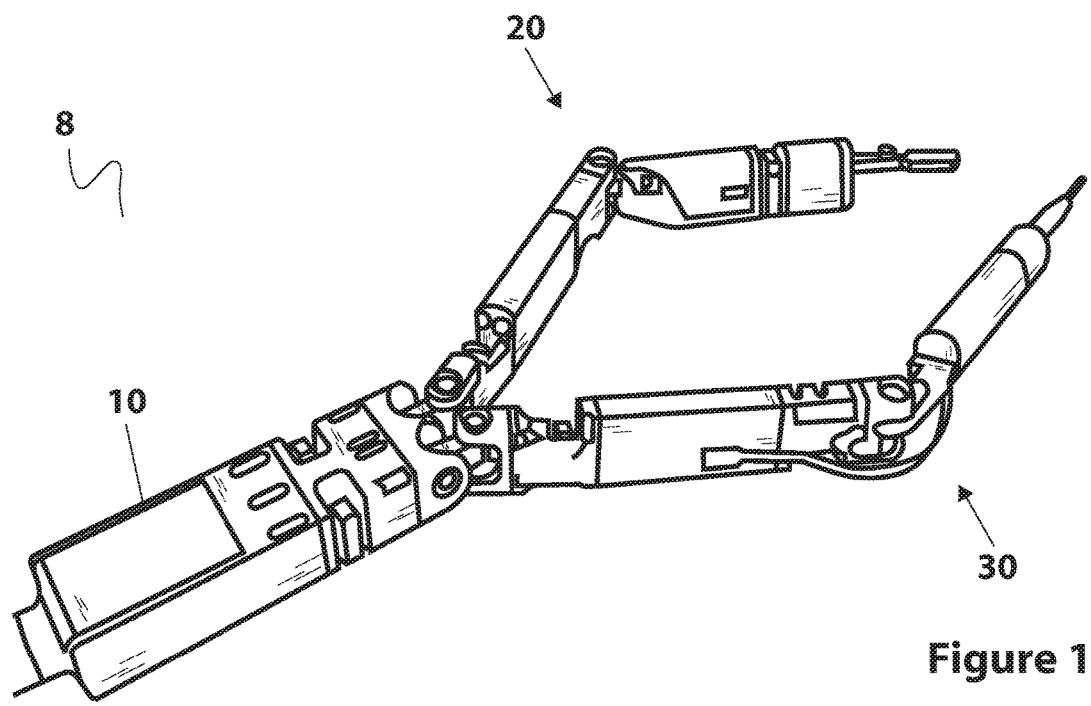
FIG. 1A is a perspective view a robotic medical device, according to one embodiment.

The various systems and devices disclosed herein relate to devices for use in medical procedures and systems. More specifically, various embodiments relate to various medical devices, including robotic devices and related methods and systems.

It is understood that the various embodiments of robotic devices and related methods and systems disclosed herein can be incorporated into or used with any other known medical devices, systems, and methods. For example, the various embodiments disclosed herein may be incorporated into or used with any of the medical devices and systems disclosed in copending U.S. application Ser. No. 11/766,683 (filed on Jun. 21, 2007 and entitled "Magnetically Coupleable Robotic Devices and Related Methods"), Ser. No. 11/766,720 (filed on Jun. 21, 2007 and entitled "Magnetically Coupleable Surgical Robotic Devices and Related Methods"), Ser. No. 11/966,741 (filed on Dec. 28, 2007 and entitled "Methods, Systems, and Devices for Surgical Visualization and Device Manipulation"), 61/030,588 (filed on Feb. 22, 2008), Ser. No. 12/171,413 (filed on Jul. 11, 2008 and entitled "Methods and Systems of Actuation in Robotic Devices"), Ser. No. 12/192,663 (filed Aug. 15, 2008 and entitled Medical Inflation, Attachment, and Delivery Devices and Related Methods"), Ser. No. 12/192,779 (filed on Aug. 15, 2008 and entitled "Modular and Cooperative Medical Devices and Related Systems and Methods"), Ser. No. 12/324,364 (filed Nov. 26, 2008 and entitled "Multifunctional Operational Component for Robotic Devices"), 61/640,879 (filed on May 1, 2012), Ser. No. 13/493,725 (filed Jun. 11, 2012 and entitled "Methods, Systems, and Devices Relating to Surgical End Effectors"), Ser. No. 13/546,831 (filed Jul. 11, 2012 and entitled "Robotic Surgical Devices, Systems, and Related Methods"), 61/680,809 (filed Aug. 8, 2012), Ser. No. 13/573,849 (filed Oct. 9, 2012 and entitled "Robotic Surgical Devices, Systems, and Related Methods"), and Ser. No. 13/738,706 (filed Jan. 10, 2013 and entitled "Methods, Systems, and Devices for Surgical Access and Insertion"), and U.S. Pat. No. 7,492,116 (filed on Oct. 31, 2007 and entitled "Robot for Surgical Applications"), 7,772,796 (filed on Apr. 3, 2007 and entitled "Robot for Surgical Applications"), and U.S. Pat. No. 8,179,073 (issued May 15, 2011, and entitled "Robotic Devices with Agent Delivery Components and Related Methods"), all of which are hereby incorporated herein by reference in their entireties.

Certain device and system implementations disclosed in the applications listed above can be positioned within a body cavity of a patient in combination with a support component similar to those disclosed herein. An "in vivo device" as used herein means any device that can be positioned, operated, or controlled at least in part by a user while being positioned within a body cavity of a patient, including any device that is coupled to a support component such as a rod or other such component that is disposed through an opening or orifice of the body cavity, also including any device positioned substantially against or adjacent to a wall of a body cavity of a patient, further including any such device that is internally actuated (having no external source of motive force), and additionally including any device that may be used laparoscopically or endoscopically during a surgical procedure. As used herein, the terms "robot," and "robotic device" shall refer to any device that can perform a task either automatically or in response to a command.

Certain embodiments provide for insertion of the present invention into the cavity while maintaining sufficient insufflation of the cavity. Further embodiments minimize the physical contact of the surgeon or surgical users with the present invention during the insertion process. Other implementations enhance the safety of the insertion process for the patient and the present invention. For example, some embodiments provide visualization of the present invention as it is being inserted into the patient's cavity to ensure that no damaging contact occurs between the system/device and the patient. In addition, certain embodiments allow for minimization of the incision size/length. Further implementations reduce the complexity of the access/insertion procedure and/or the steps required for the procedure. Other embodiments relate to devices that have minimal profiles, minimal size, or are generally minimal in function and appearance to enhance ease of handling and use.

Certain embodiments herein relate to robotic devices (also referred to herein as "platforms") configured to be inserted into a patient cavity—such as an insufflated abdominal cavity—and related systems and methods. In some embodiments, the systems include direct visualization of the device during the procedure. Other embodiments relate to various access or insertion devices that can be used to position the above robotic devices in the patient's cavity.

Figure 1B:
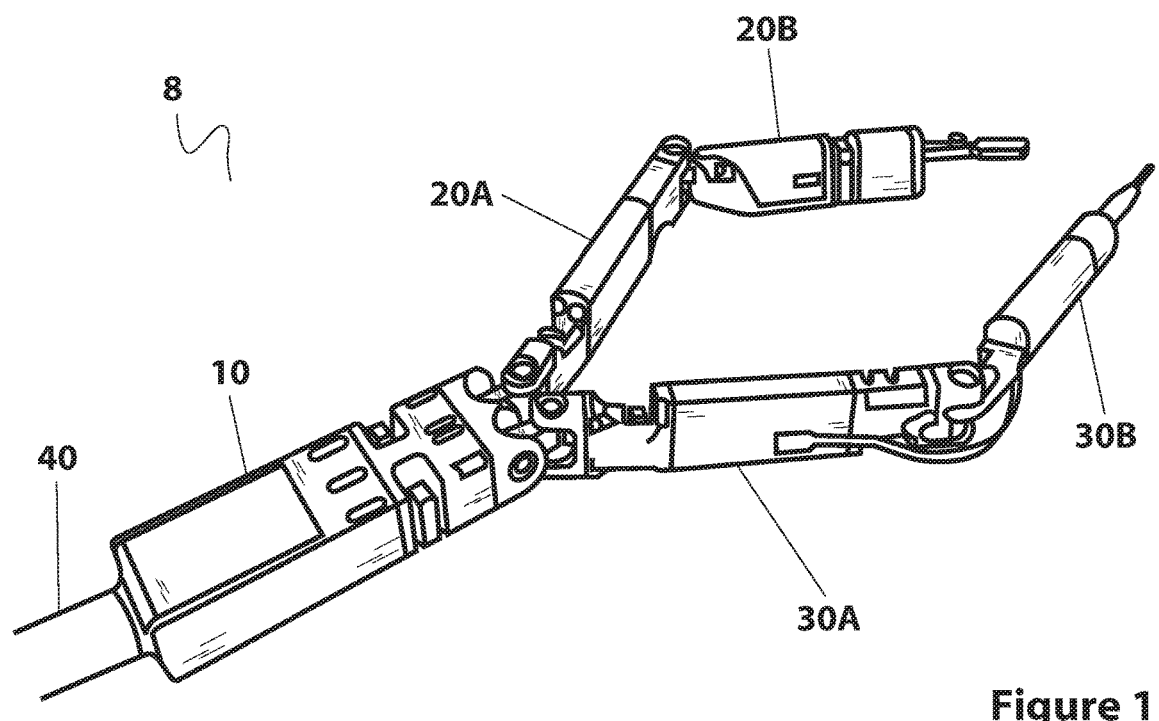
FIG. 1B is a perspective view of the robotic medical device of FIG. 1A.
Figure 1C:
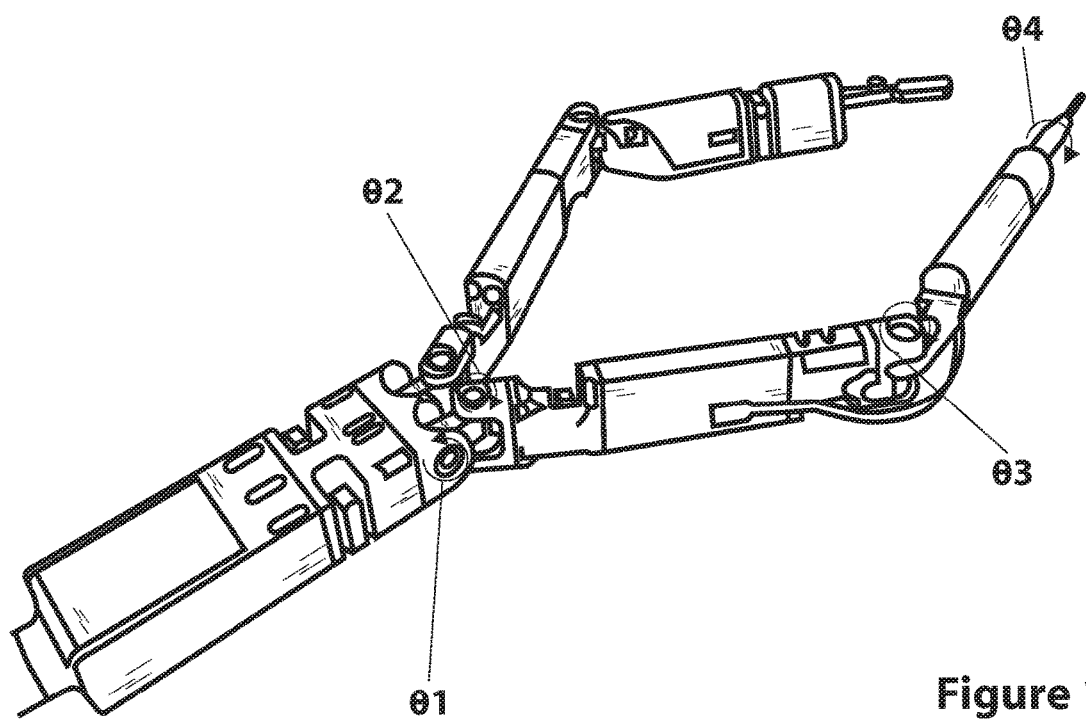
FIG. 1C is a perspective view of the robotic medical device of FIG. 1A.
Figure 2:
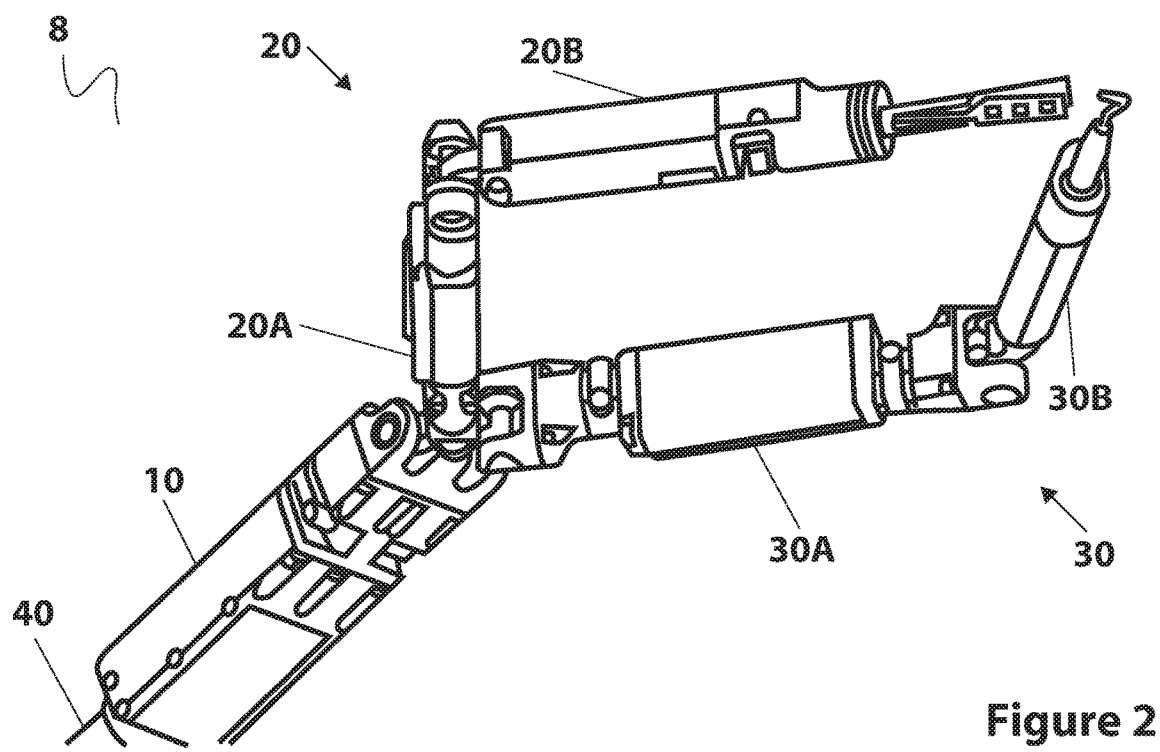
FIG. 2 is a perspective view of the robotic medical device of FIG. 1A.

One embodiment of a robotic device 8 is depicted in FIGS. 1A-1C and 2. This embodiment has a device body 10, a left arm 20, and a right arm 30, as shown in FIGS. 1A and 2. Both the left and right arms 20, 30 are each comprised of 2 segments: an upper arm (or "first link") and a forearm (or "second link"). Thus, as best shown in FIG. 1B, the left arm 20 has an upper arm 20A and a forearm 20B and the right arm 30 has an upper arm 30A and a forearm 30B. As also shown in FIGS. 1B and 2, the device main body 10 can, in some embodiments, be coupled to an insertion rod 40.

As best shown in FIG. 1C, the various joints in the right arm 30 provide for various degrees of freedom. More specifically, the right shoulder (the joint at which the upper arm 30A is coupled to the device body 10) provides two degrees of freedom: shoulder pitch $\theta 1$ and shoulder yaw $\theta 2$. The elbow joint (the joint at which the forearm 30B is coupled to the upper arm 30A) provides elbow yaw $\theta 3$, and the end effector on the distal end of the forearm 30B provides end effector roll $\theta 4$.

As shown in FIGS. 1A-1C and 2, the device 8 is configured to have a reduced profile and/or cross-section. That is, the shoulder joints (where the upper arms 20A, 30A couple with the body 10), are positioned within the longitudinal cross-section of the body 10 such that shoulder joints and the proximal ends of the upper arms 20A, 30A do not extend beyond or exceed that cross-section. Further, when the arms 20, 30 are positioned in a straight configuration such that the upper arms 20A, 30A and forearms 20B, 30B extend along the same axis (the elbows are not bent), no part of the arms 20, 30 extend beyond the longitudinal cross-section of the body 10. This minimal cross-section greatly simplifies insertion of the device 8 into an incision. For purposes of this application, the "longitudinal cross-section" is the cross-section of the body 10 as viewed when looking at the distal end or the proximal end of the body 10 such that one is looking along the longitudinal axis of the body 10.

Figure 3A:
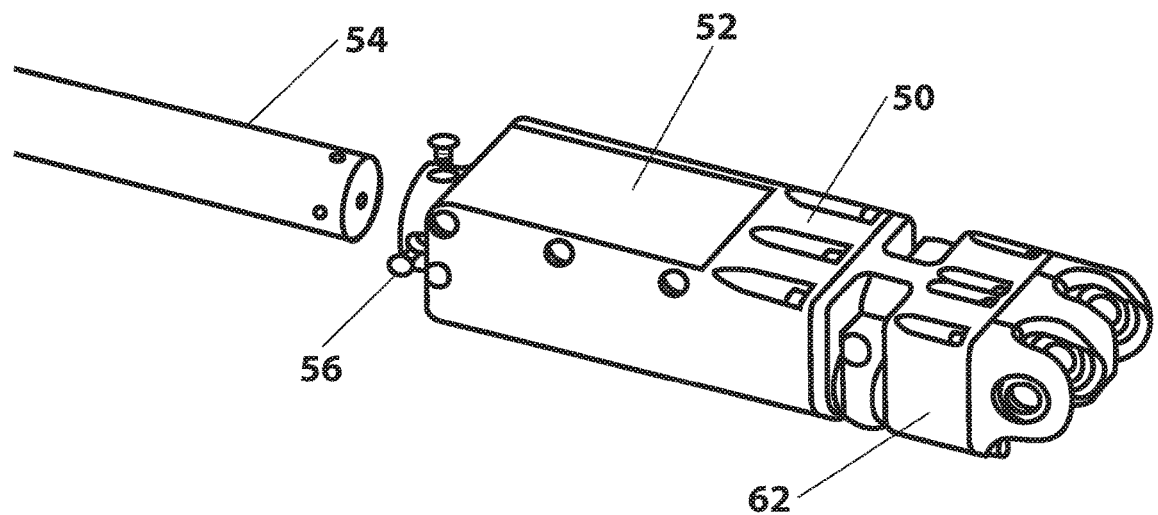
FIG. 3A is a perspective view of a device body of a robotic device, according to one embodiment.
Figure 3B:
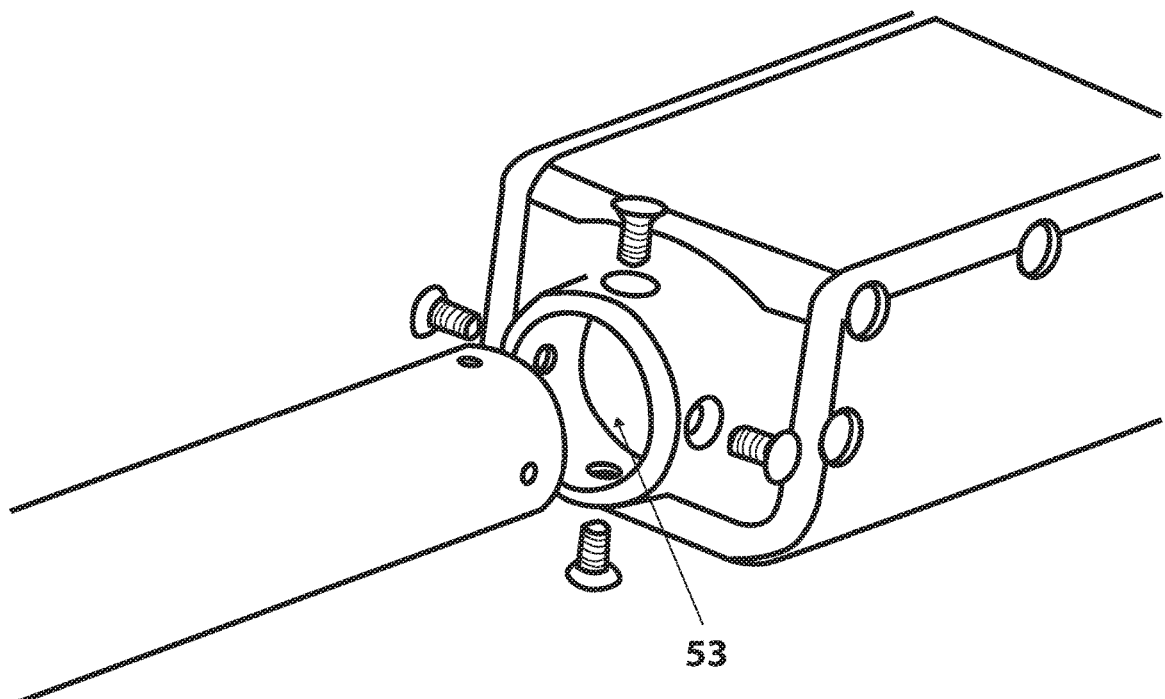
FIG. 3B is a different perspective view of the device body of FIG. 3A.

Various embodiments of the device body 10 are depicted in FIGS. 3A-9B. As shown in FIGS. 3A and 3B, the device body 10 has a motor housing 50 that is configured to contain at least one motor (described below) and a master control board (not shown) or other processor configured to control various components and/or actions of the device. The device body 10 also has a gear housing 62 coupled to the motor housing 50. In addition, as best shown in FIGS. 3A and 5A, the housing 50 has a housing cover 52 that is configured to be coupleable to the housing 50 and to provide access to the at least one motor positioned within an internal portion of the housing 50.

In one embodiment as shown in FIGS. 3A and 3B, the housing cover 52 has an opening 53 defined in the portion of the housing cover 52 that covers the proximal end of the housing 50. The opening 53 is configured to receive an insertion rod 54 (also referred to as a "positioning rod" or "positioning component"). In accordance with one implementation, screws 56 or other fastening components are used to couple the rod 54 to the cover 52 as shown. According to one implementation, the insertion rod 54 is used to advance the device 8 during insertion. In other implementations, it can also be used to position the device 8 within the patient's cavity during the procedure. In accordance with certain embodiments, the rod 54 will have communication and power wires (also referred to herein as "cables" or "connection components") disposed in one or more lumens defined in the rod 54 that will operably couple the device 8 to an external controller (not shown). For example, the external controller can be a personal computer, a joystick-like controller, or any other known controller that allows a user to operate the device 8. In further embodiments in which the device 8 has at least one camera, the connection components can also include one or more camera and/or lighting wires.

Figure 4A:
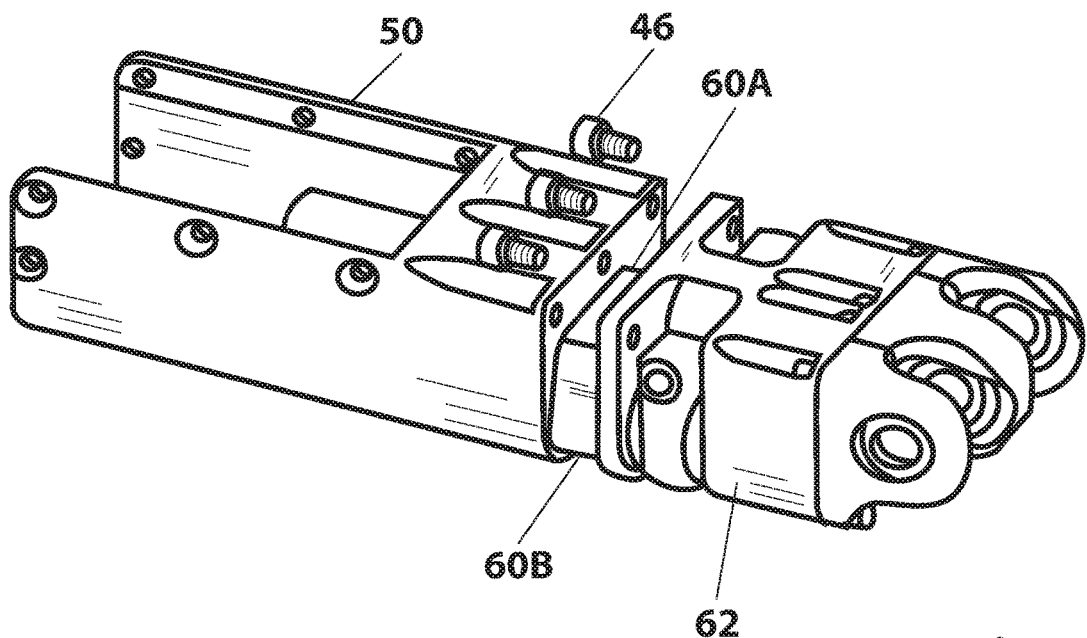
FIG. 4A is a different perspective view of the device body of FIG. 3A.
Figure 4B:
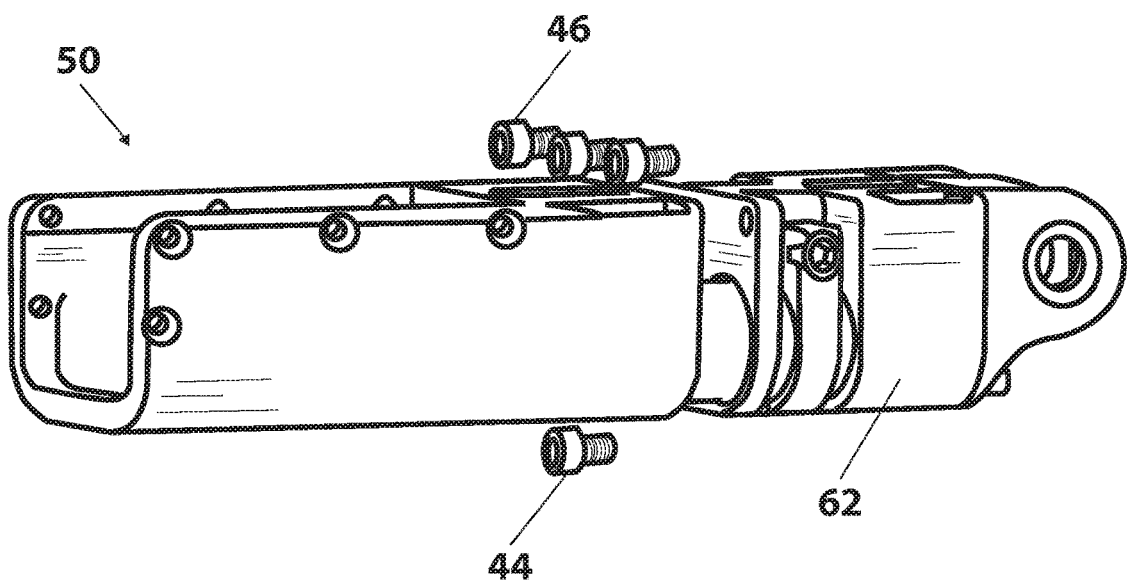
FIG. 4B is a side view of the device body of FIG. 3A.

As best shown in FIGS. 4A and 4B, the motor housing 50 is coupled to the gear housing 62 such that a portion of each of the motor assemblies 60A, 60B is positioned in the motor housing 50 and a portion is positioned in the gear housing 62. In one embodiment, the motor housing 50 is coupled to the gear housing 62 with screws 44, 46 that are positioned through holes in the motor housing 50 and threadably coupled within holes in the gear housing 62.

Figure 5A:
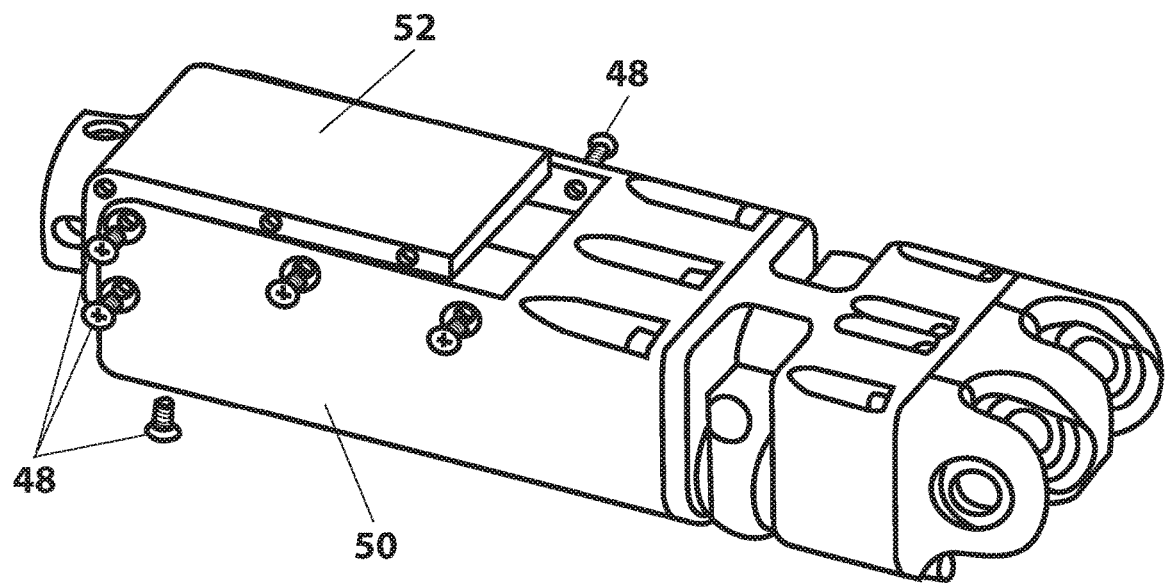
FIG. 5A is a different perspective view of the device body of FIG. 3A.
Figure 5B:
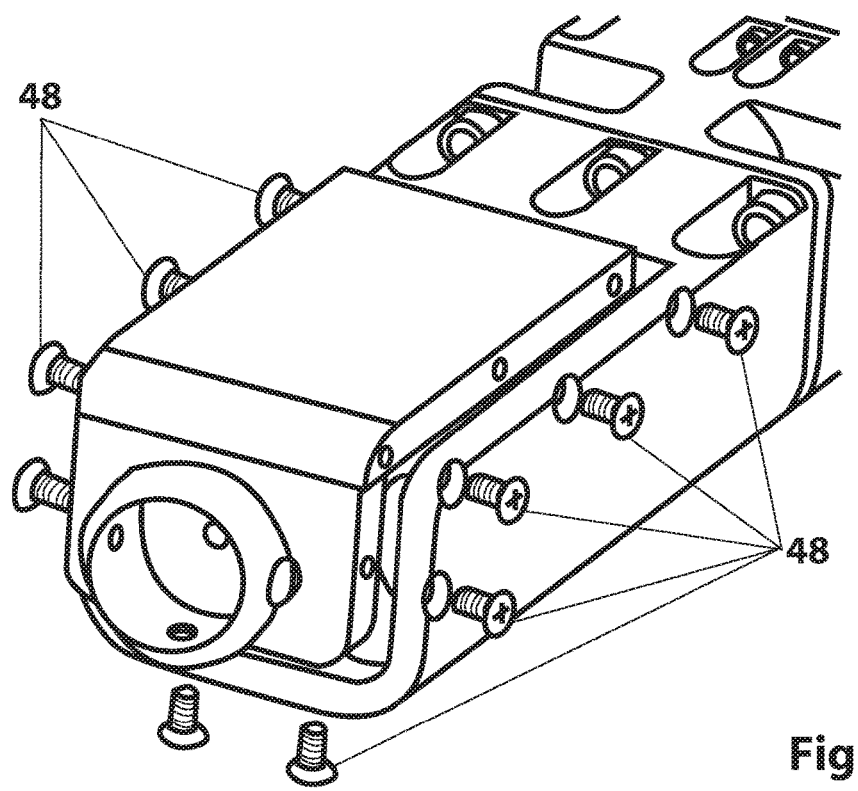
FIG. 5B is a different perspective view of the device body of FIG. 3A.

As best shown in FIGS. 5A and 5B, in one embodiment the housing cover 52 is removably coupled to the motor housing 50 with screws 48. The screws 48 are positioned through holes defined in the housing 50 and threadably coupled within holes in the housing cover 52. Alternatively, any known coupling mechanisms, such as bolts or snap or friction fit mechanisms, can be used to removably couple the cover 52 to the housing 50.

As discussed above and depicted in FIGS. 4A, 4B, 5A, and 5B, the device body 10 contains the two motor assemblies 60A, 60B. The two motor assemblies 60A, 60B actuate the movement of the left and right arms 20, 30, as will be described in further detail below. In addition, the body 10 can also contain a master control board (not shown) and a stereoscopic camera (not shown). In one embodiment, the master control board controls the motors 60A, 60B.

In accordance with one embodiment, each of the two motor assemblies 60A, 60B is the actuator for a drive train with a three stage gear head. That is, the left motor assembly 60A is the actuator for a drive train coupled to the left arm 20, while the right motor assembly 60B is the actuator for a drive train coupled to the right arm 30. While the following description will focus on the right motor 60B and its drive train, it is understood that the left motor assembly 60A and its drive train will have similar components and operate in a similar fashion.

Figure 8A:
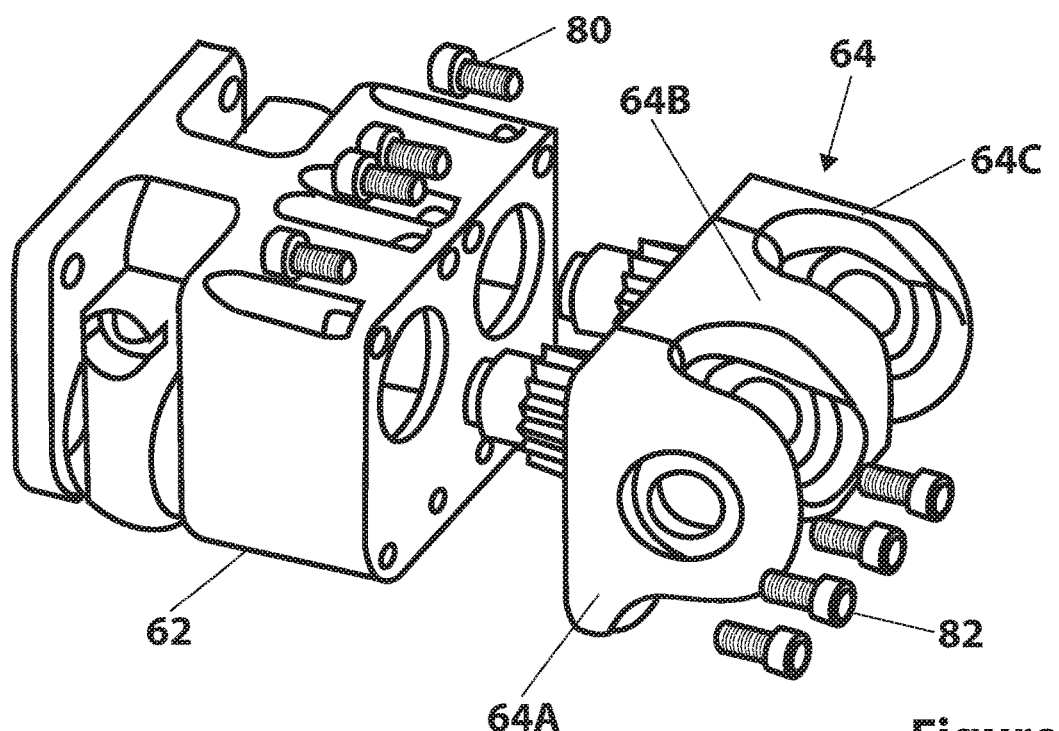
FIG. 8A is a perspective view of a gear housing, according to one embodiment.
Figure 8B:
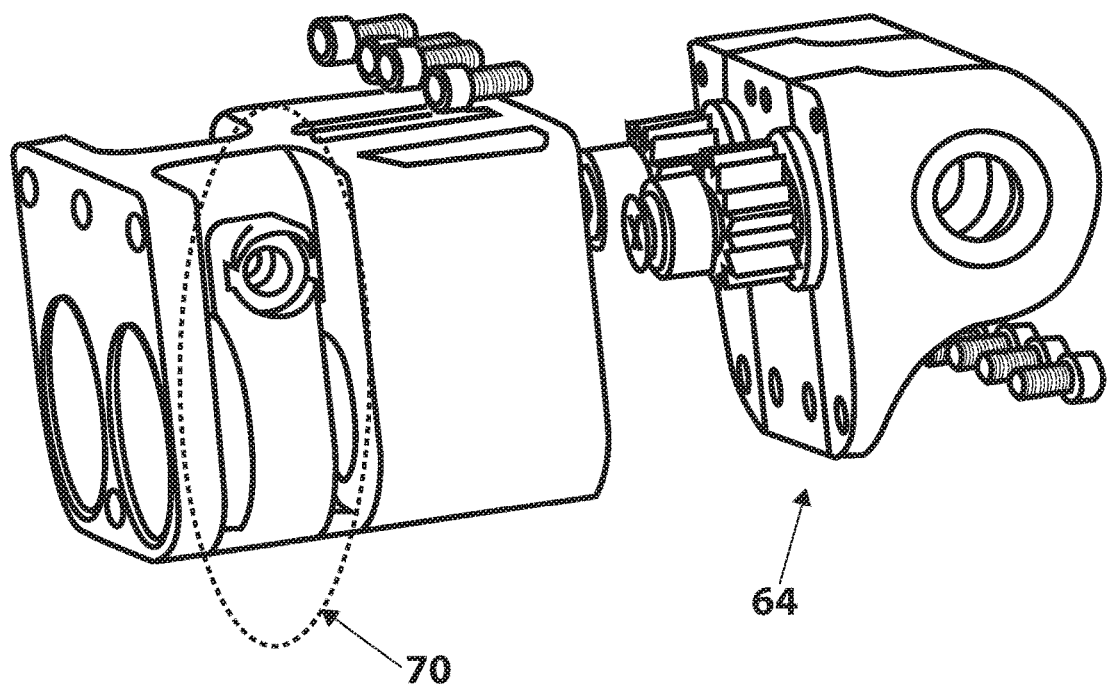
FIG. 8B is a different perspective view of the gear housing of FIG. 8A.
Figure 9A:
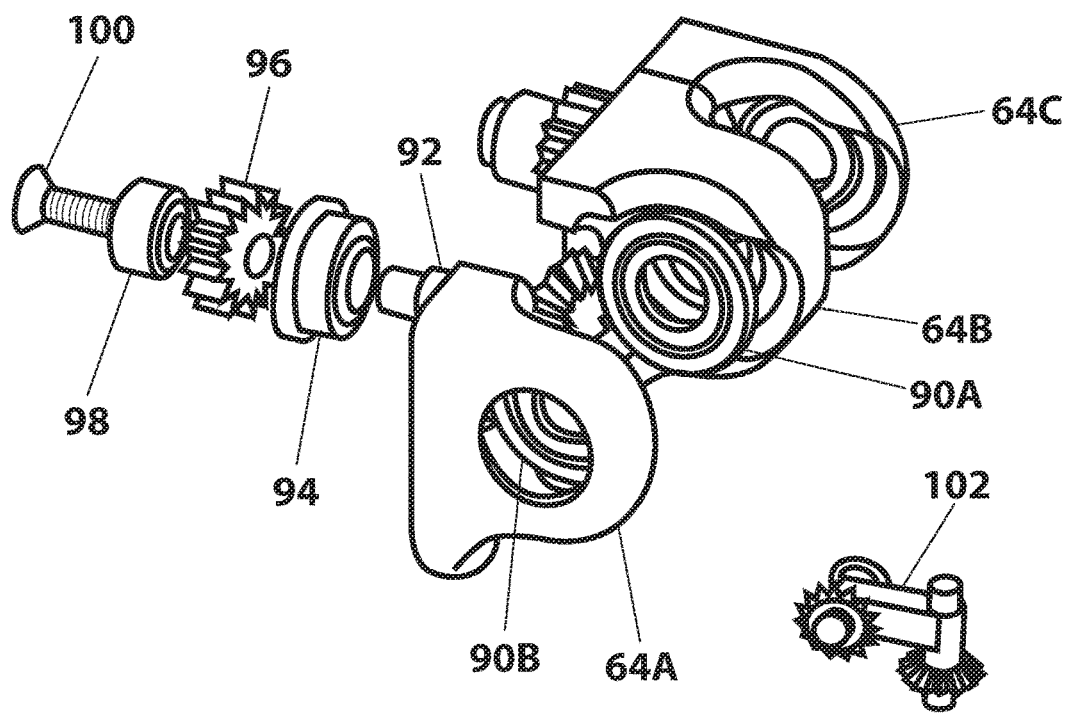
FIG. 9A is a different perspective view of parts of the gear housing of FIG. 8A.

In one implementation, as best shown in FIGS. 6A, 6B, 8A, 8B, 9A, and 9B, the first stage of the three stage gear head is the gear head 60B-2 attached to the motor 60B-1 of the motor assembly 60B. The second stage is the spur gear set, which is made up of the motor gear 68 and the driven gear 96 as best shown in FIG. 9A. The motor gear 68 and the driven gear 96 are rotationally coupled to each other in the gear housing 62. In one embodiment, the motor gear 68 and driven gear 96 are spur gears. Alternatively, they can be any known gears. The motor gear 68 is also known as a "first gear," "drive gear," or "driving gear." The driven gear 96 is also known as a "second gear" or "coupling gear." The third stage is the bevel gear set, which is made up of the housing bevel gear 92 and the link bevel gear 102. The housing bevel gear 92 and the link bevel gear 102 are rotationally coupled to each other as best shown in FIG. 9A. These components and gear sets will be discussed in detail below. The housing bevel gear 92 is also known as the "third gear," "housing gear," "second drive gear," or "first shoulder gear." The link bevel gear 102 is also know as the "fourth gear," "link gear," or "second shoulder gear."

Figure 6A:
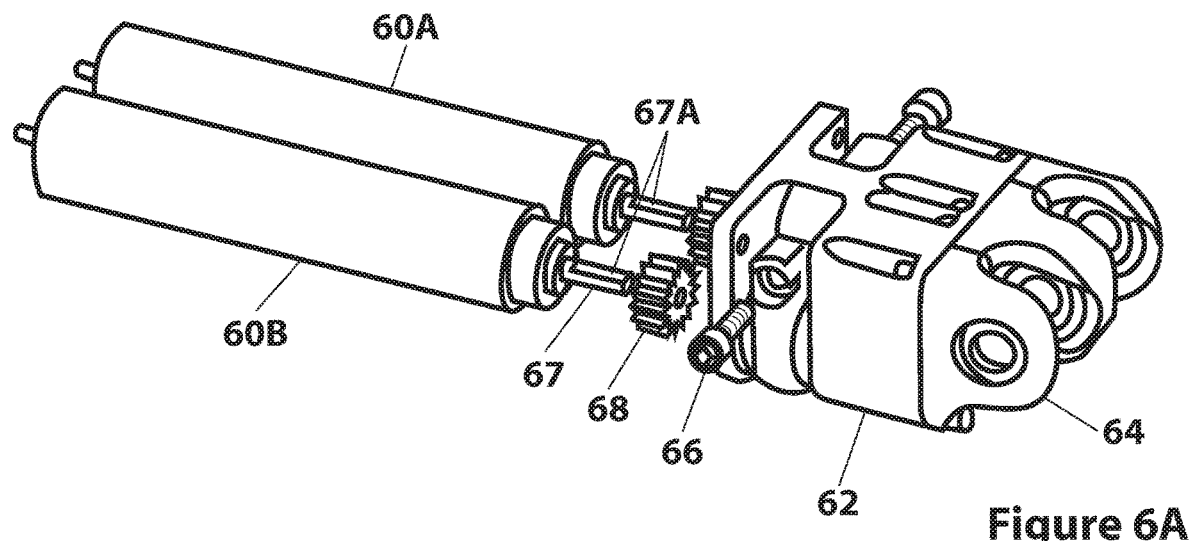
FIG. 6A is a perspective view of some of the internal components of the device body of FIG. 3A.
Figure 6B:
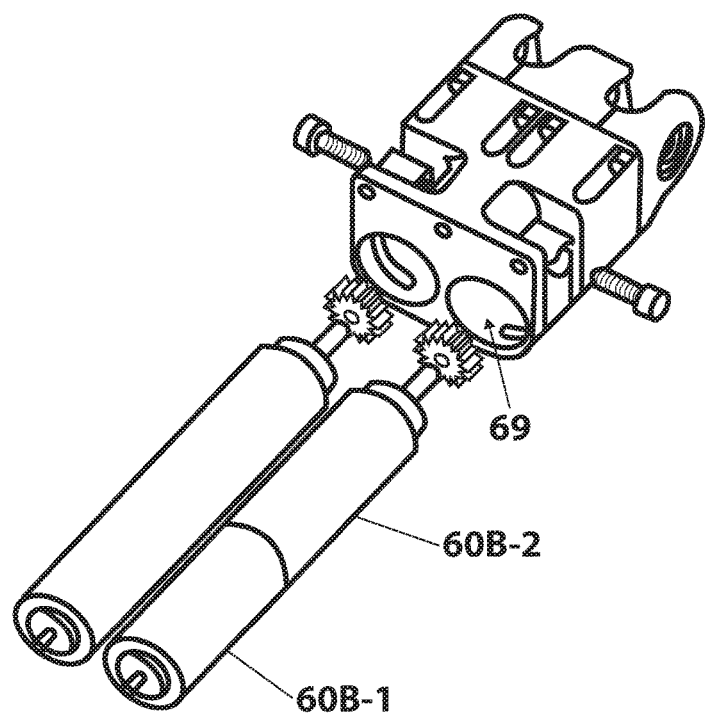
FIG. 6B is a different perspective view of the internal components of the device body of FIG. 6A.
Figure 7:
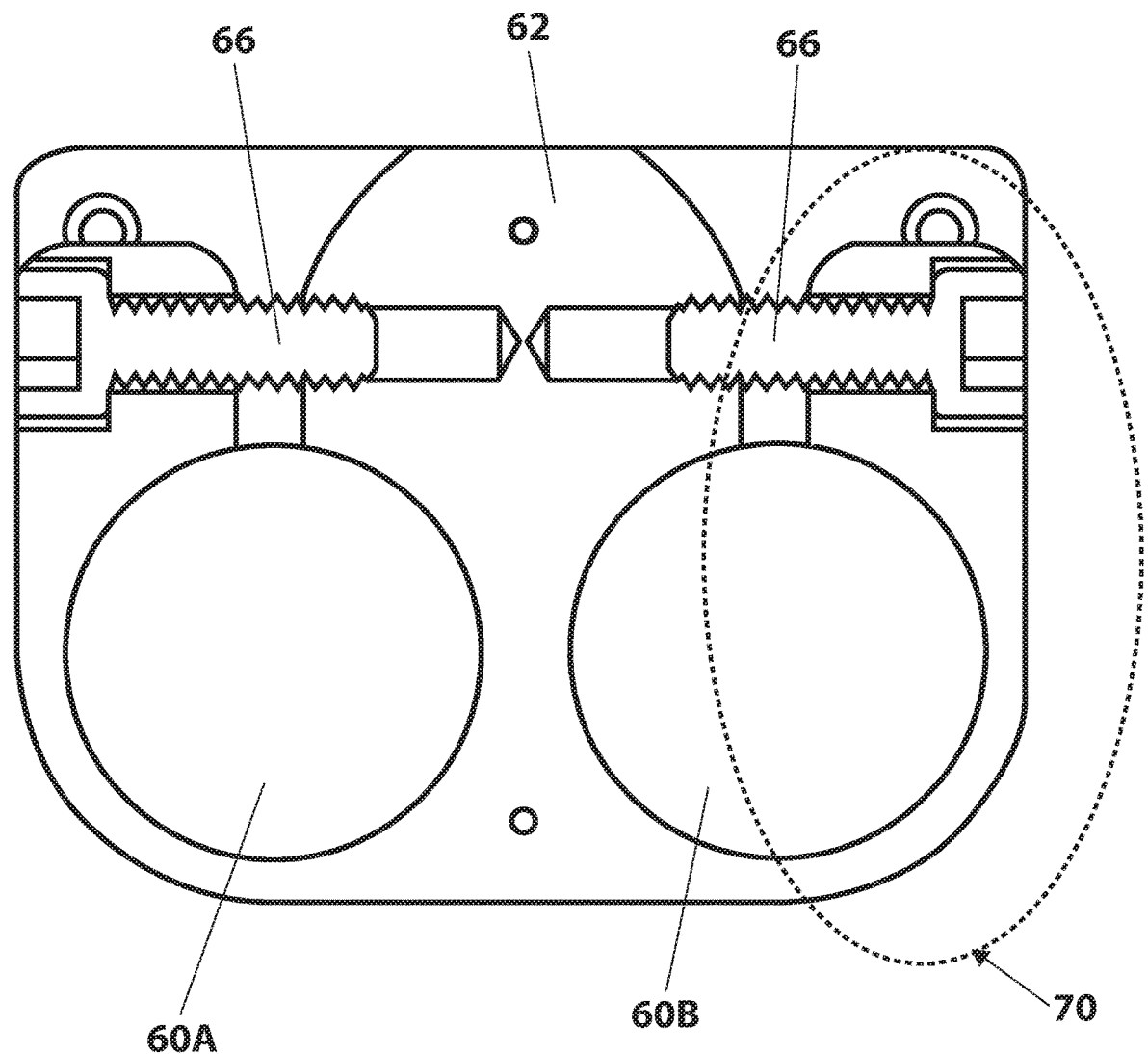
FIG. 7 is a cross-section view of the device body of FIG. 3A.

As best shown in FIGS. 6A, 6B, and 7, both the right and left motor assemblies 60A, 60B are positioned at their distal ends into the gear housing 62. The right motor assembly 60B has a motor 60B-1 and a gearhead 60B-2. In this embodiment, the gearhead 60B-2 is the first stage gear head and is operably coupled to the motor 60B-1. The motor assembly 60B has a motor shaft 67 operably coupled at the distal end of the assembly 60B. In one embodiment, the motor shaft 67 has a flat surface 67A that creates a "D" configuration that geometrically couples the shaft 67 to the spur gear 68. The right motor assembly 60B is positioned in the right motor gear opening 69 of the gear housing 62, as best shown in FIG. 6B. In one embodiment, the motor assembly 60B has a configuration or structure that allows for the assembly 60B to be geometrically coupled within the right motor gear opening 69. Further, as best shown in FIG. 7, the gear housing 62 has a clamp 70 that can be used to retain the motor assembly 60B within the motor gear opening 69. That is, a threaded screw 66 or other coupling mechanism is positioned in the clamp 70 and threaded into the clamp 70, thereby urging the clamp 70 against the assembly 60B, thereby retaining it in place. Alternatively, the assemblies 60A, 60B can be secured to the housing 62 via adhesive or any other known coupling or securement mechanisms or methods.

As best shown in FIGS. 8A and 8B, the gear housing 62 is coupled to a bearing housing 64. In one embodiment, the bearing housing 64 is comprised of three housing projections 64A, 64B, 64C. As best shown in FIG. 8B in combination with FIGS. 9A and 9B, the right driven spur gear assembly 96 is rotationally coupled to the bearing housing 64. More specifically, the right driven spur gear assembly 96 is rotationally retained in the bearing housing by the bearings 94, 98 as shown in FIG. 9A. The bearings 94, 98 are positioned in and supported by the bearing housing 64 and the gear housing 62.

Figure 9B:
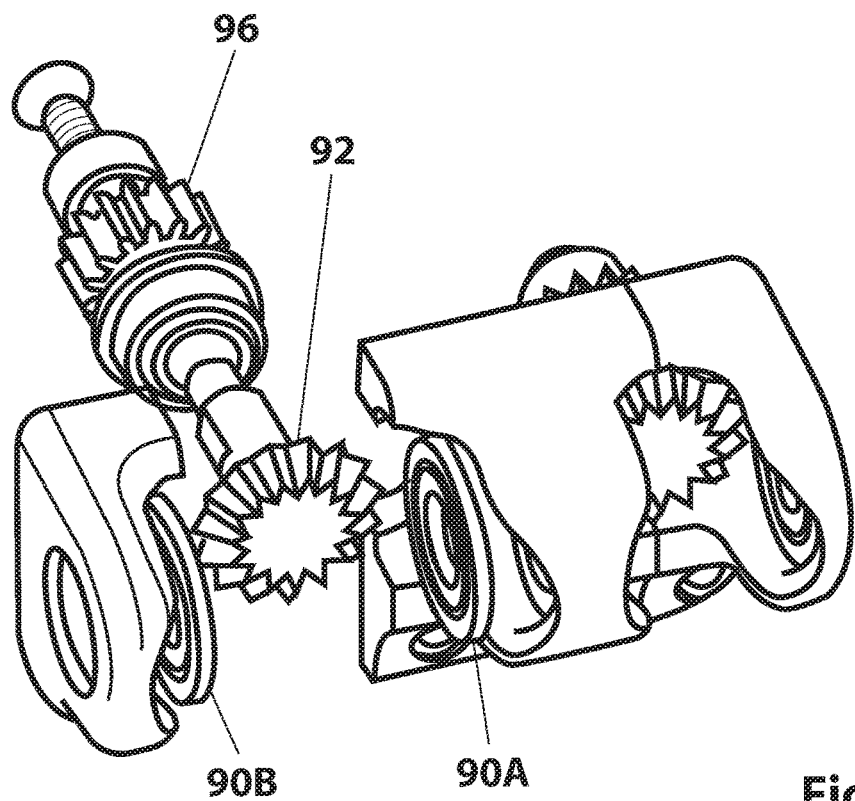
FIG. 9B is a different perspective view of parts of the gear housing of FIG. 8A.

As best shown in FIGS. 8A and 8B in combination with FIGS. 9A and 9B, the spur gear assembly 96 is operably coupled to the housing bevel gear 92 such that the spur gear 96 drives the bevel gear 92. More specifically, the spur gear 96 is positioned over the proximal portion of the bevel gear 92, with the proximal portion having a flat portion or other configuration that rotationally couples the spur gear 96 to the bevel gear 92 such that the spur gear 96 and bevel gear 92 are not rotatable in relation to each other. Further, the bevel gear 92 is positioned between the first and second housing projections 64A and 64B and supported by bearings 94, 98. As best shown in FIG. 9A, the bearings 94, 98 and the spur gear 96 are secured to the gear 92 by screw 100, which is threadably coupled to the bevel gear 92. Further, the bevel gear 92 is rotationally coupled to the first and second projections 64A, 64B. The spur gear 96 and bevel gear 92 are rotationally coupled to housing 62 and housing 64 by screws 80, 82 (as best shown in FIG. 8A), which are threadably coupled to the housings 62, 64 such that the housings 62, 64 are coupled to each other.

As mentioned above, the bevel gear 92 is rotationally coupled to the link 102, which is operably coupled to the right arm 30 of the device 8 as described in further detail below. Thus, the link 102 couples the device body 10 to the right arm 30 such that actuation of the motor 60B results in actuation of some portion or component of the right arm 30. The link 102 is supported by bearings 90A, 90B, which are coupled to the housing 64 as best shown in FIGS. 9A and 9B.

Figure 10A:
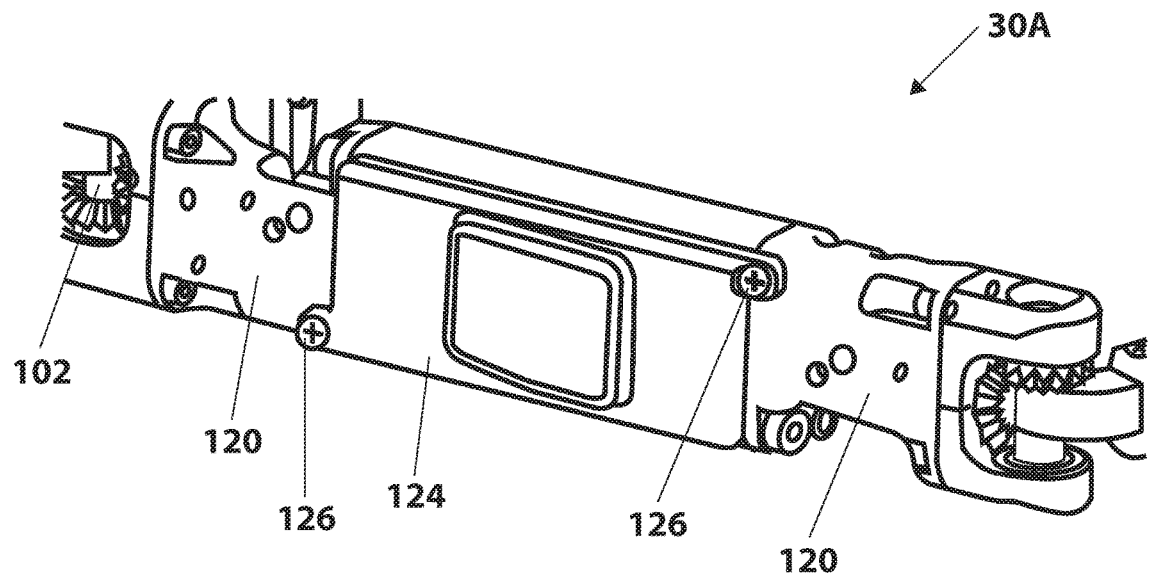
FIG. 10A is a perspective view of an upper arm, according to one embodiment.
Figure 10B:
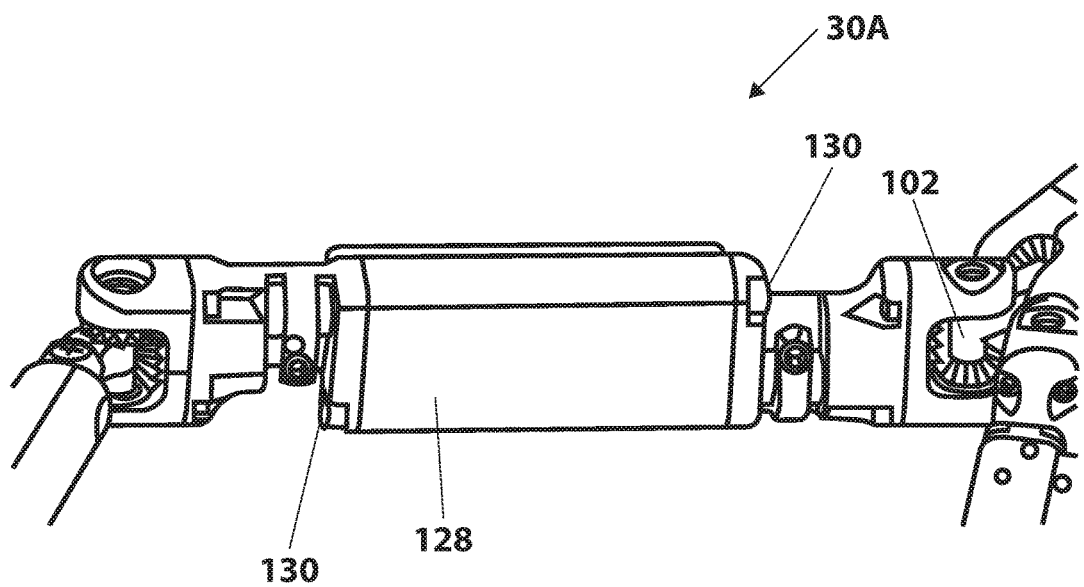
FIG. 10B is a different perspective view of the upper arm of FIG. 10A.

In one implementation, the right upper arm 30A is coupled to the device body 10. And in certain embodiments, the right upper arm 30A is more specifically coupled to the link 102 discussed above. As best shown in FIGS. 10A and 10B, the upper arm 30A is coupled to the device body 10 at the link 102. The upper arm 30A has a motor housing 128 configured to hold at least one motor and a housing cover 124 coupled to the housing 128. The housing cover 124 is coupled to the motor housing 128 by screws 126, which are threadably coupled to the motor housing 128 as shown. Alternatively, any mechanical coupling mechanisms can be used. The motor housing 128 is operably coupled to a spur gear housing 120 at each end of the motor housing 128 such that there are two spur gear housings 120 coupled to the motor housing 128.

Figure 11A:
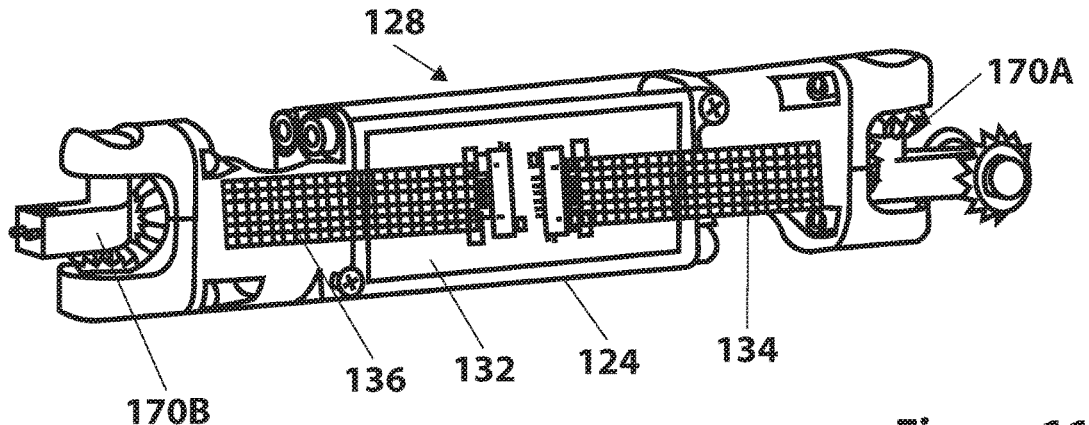
FIG. 11A is a different perspective and cutaway view of the upper arm of FIG. 10A.
Figure 11B:
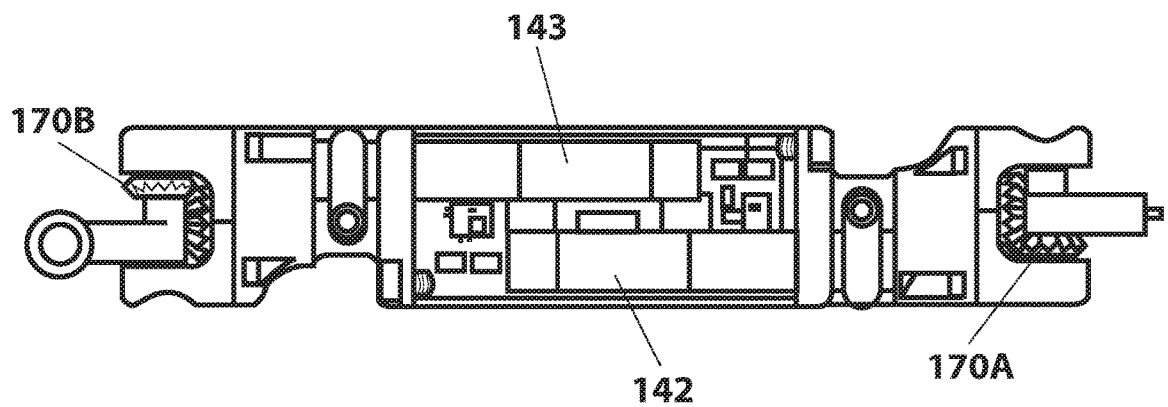
FIG. 11B is a side and cutaway view of the upper arm of FIG. 10A.
Figure 11C:
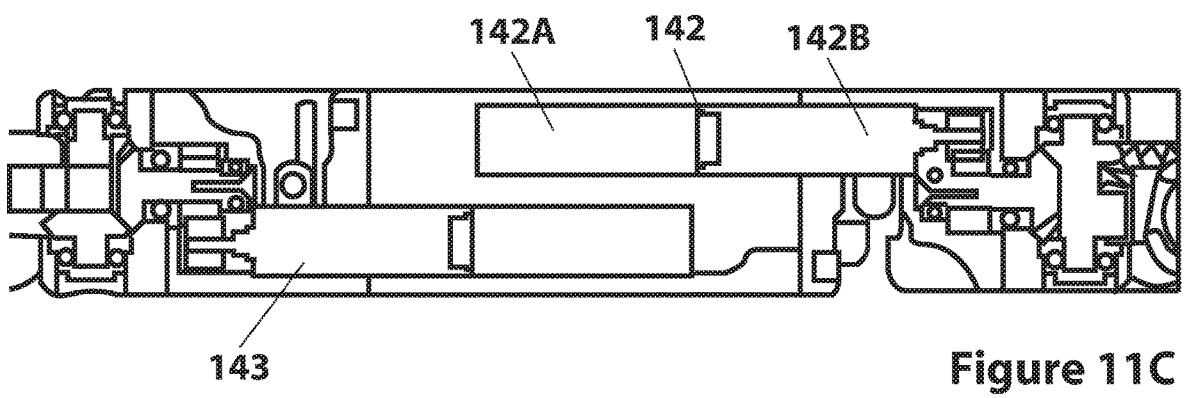
FIG. 11C is a cross-section view of the upper arm of FIG. 10A.

As best shown in FIGS. 11A, 11B, and 11C, the housing 128 contains two motor and gear head assemblies 142, 143 and a local control board 132, which will be described in further detail below. The two assemblies 142, 143 are secured to the housing 128 with screws 130, which are threadably coupled to motor housing 128 as best shown in FIG. 10B.

As best shown in FIG. 11A, the local control board 132 is operably coupled to the motor housing 128 and housing cover 124 and controls the two motor assemblies 142, 143 in the housing 128. The board 132 is also operably connected to both of the motor assemblies 142, 143 within the housing 128 via flexible electrical ribbon cable (either FFC or FPC) 134, 136. The board 132 receives communications (such as commands and requests, for example) from the master control board (not shown) located in the device body 10 via the flexible electrical ribbon cable 134. Further, the board 132 also transmits, passes, or relays communications (such as commands and requests) from the master board to the next device component, which—in this embodiment—is the right forearm 30B via the flexible electrical ribbon cable 136.

According to one implementation, each of the local boards disclosed herein is "daisy chained" or wired together in a sequence in the device 8. In this context, "daisy chain" is intended to have its standard definition as understood in the art. The local boards are daisy chained together using flexible ribbon cable such as the cable 134, 136 such that the cable can transmit power, analog signals, and digital data. The use of a daisy chain configuration can create an electrical bus and reduce the number of wires required.

Figure 12A:
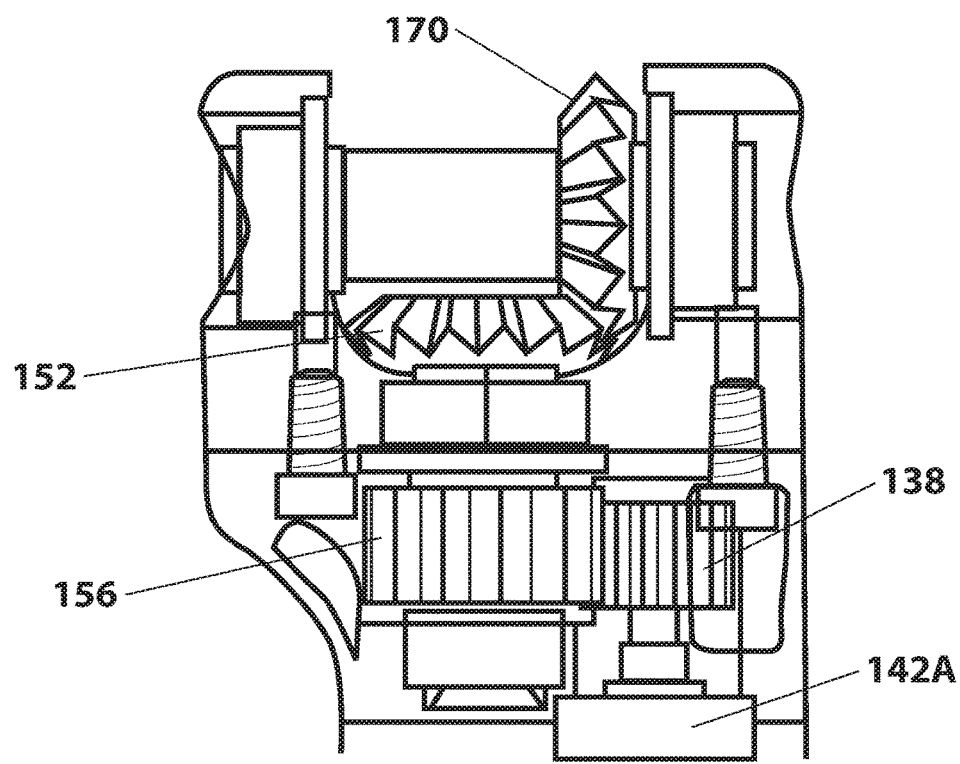
FIG. 12A is a side view of a portion of an upper arm, according to one embodiment.
Figure 12B:
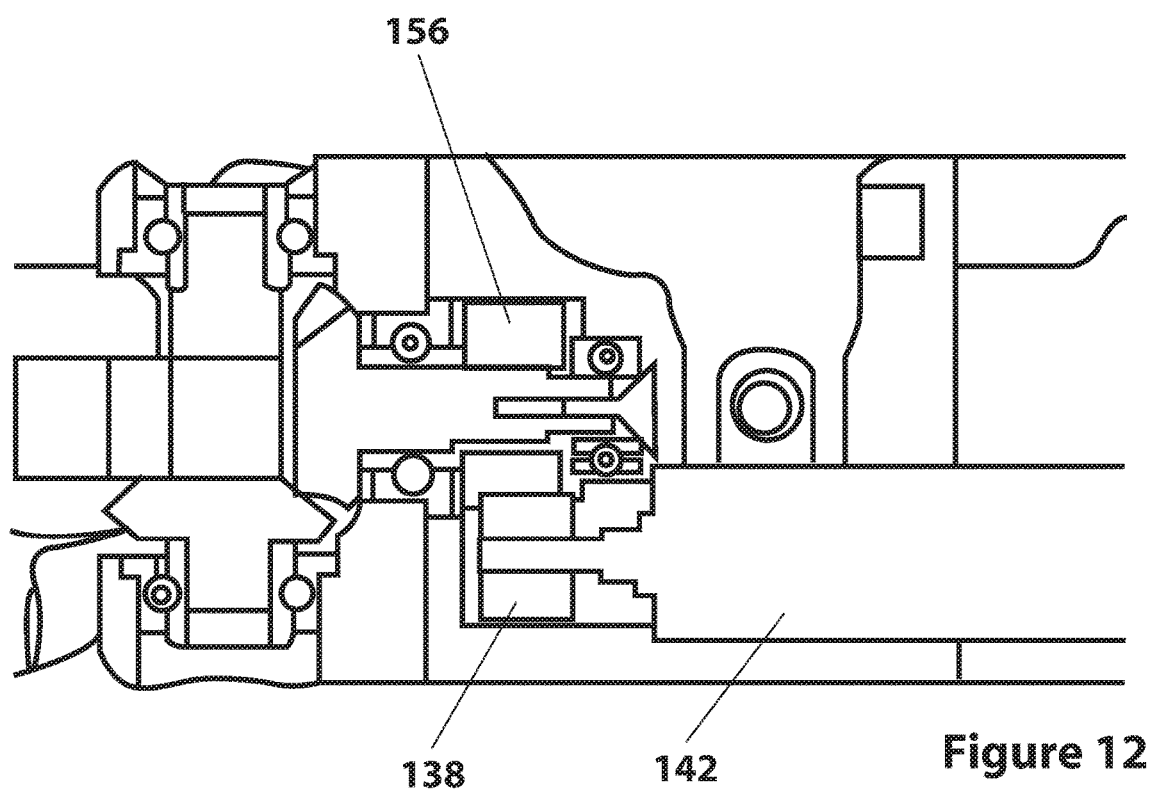
FIG. 12B is a cross-section view of the portion of the upper arm in FIG. 12A.
Figure 14A:
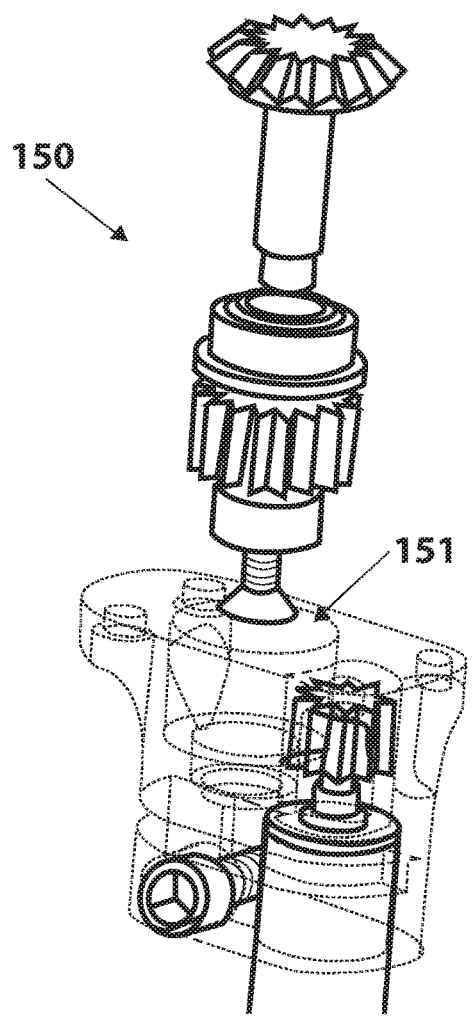
FIG. 14A is a perspective view of a portion of an upper arm, according to one embodiment.
Figure 14B:
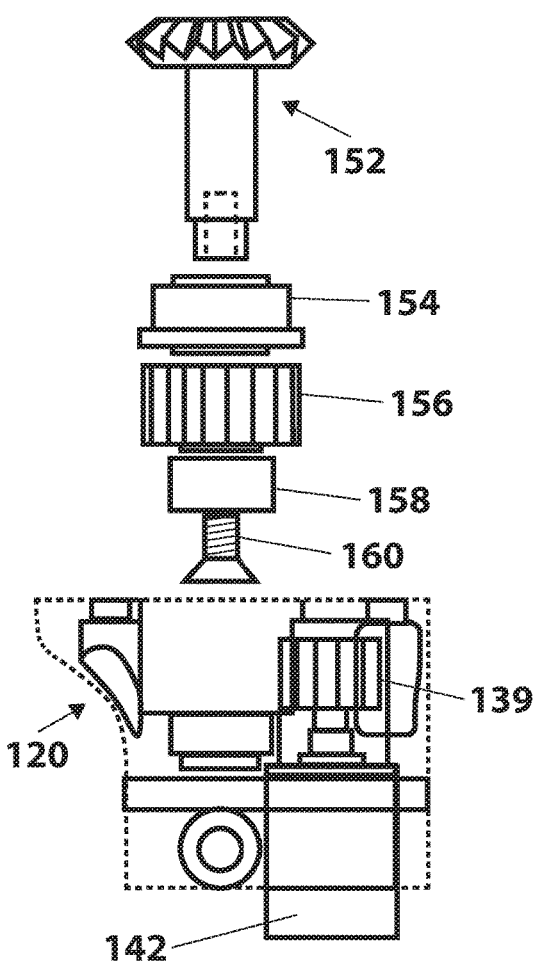
FIG. 14B is a side view of the portion of the upper arm in FIG. 14A.
Figure 15A:
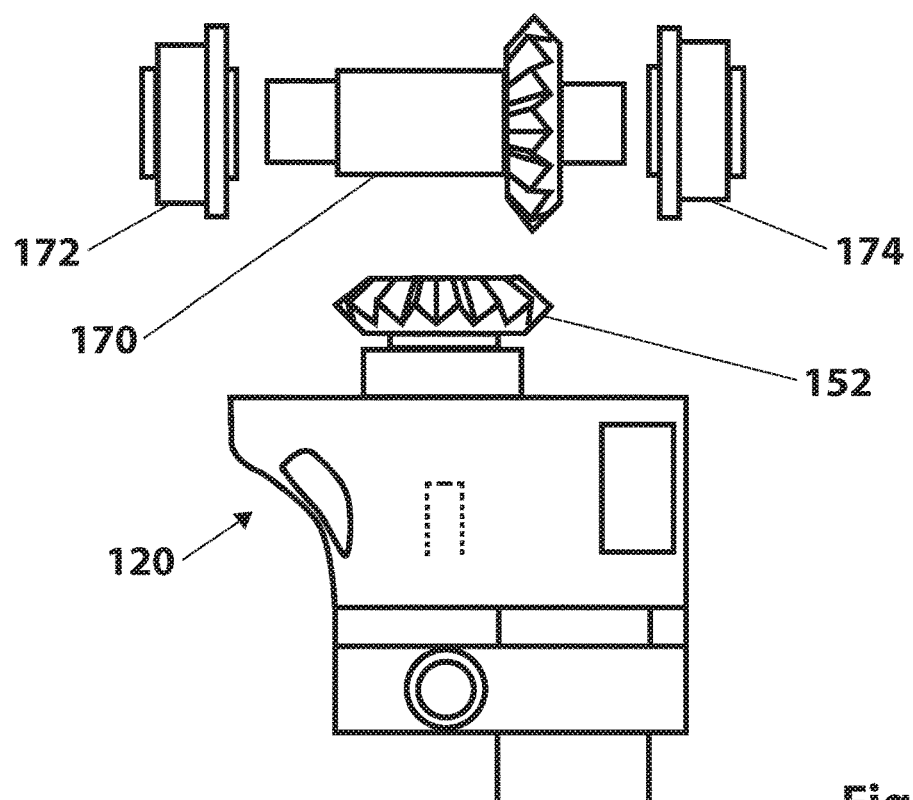
FIG. 15A is a side view of a portion of an upper arm, according to one embodiment.
Figure 15B:
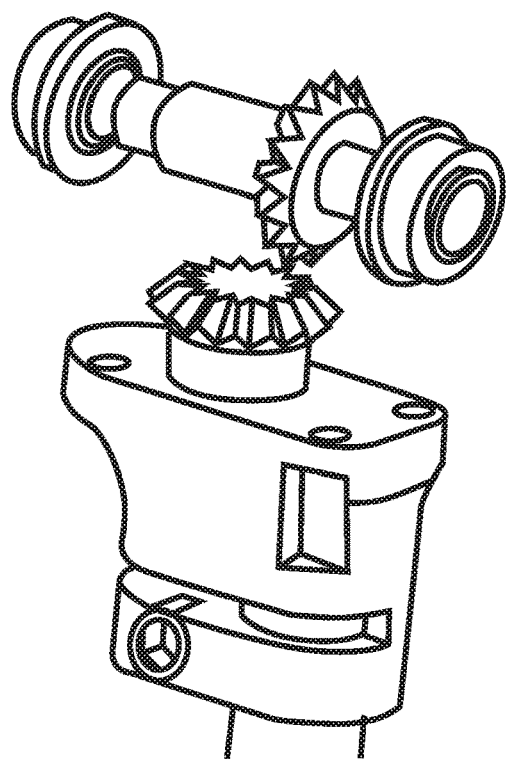
FIG. 15B is a perspective view of the portion of the upper arm in FIG. 15A.

In one embodiment, the two motor assemblies 142, 143 are responsible for the right arm 30 shoulder yaw and elbow pitch as best shown in FIG. 10. Like the description of the motor assemblies in the device body 10 as discussed above, the two motor assemblies 142, 143 in the upper arm 30A as best shown in FIGS. 11B and 11C are substantially similar, so the right motor assembly 142 will be discussed in detail herein. As best shown in FIGS. 12A and 12B, the motor drive train has a three stage gear head. The first stage is the gear head 142B attached to the motor 142A in the motor assembly 142 (as best shown in FIG. 11C), the second stage is a spur gear set made up of the motor spur gear 138 and the driven spur gear 156, and the third stage is a bevel gear set made up of the bevel gear 152 and the driven bevel gear 170. All of these components will be described in further detail below.

As best shown in FIG. 13A, the motor assembly 142 has a drive shaft 144 that is operably coupled to the spur gear 138. In one embodiment, the drive shaft 144 has a flat portion 144A that results in a D-shaped shaft, which helps to rotationally couple the spur gear 138 to the shaft 144. In a further implementation, the spur gear 138 can be further coupled to the shaft 144 using a bonding material such as, for example, JB-Weld. Alternatively, the spur gear 138 can be coupled to the shaft 144 in any known fashion using any known mechanism.

As best shown in FIGS. 13A, 13B, 13C, 13D, and 13E, the motor assembly 142 is positioned within a lumen 145 defined in the spur gear housing 120. According to one embodiment, the assembly 142 can be coupled or otherwise retained within the lumen 145 using a clamping assembly 146 (as best shown in FIGS. 13C and 13D). That is, once the motor assembly 142 is positioned within the lumen 145, the screw 140 can be urged into the hole, thereby urging the clamping assembly 146 against the motor assembly 142, thereby frictionally retaining the assembly 142 in the lumen 145. Alternatively, the assembly 142 can be secured to the housing 120 via adhesive or any other known coupling or securement mechanisms or methods.

As best shown in FIGS. 12A, 12B, 14A, and 14B, the second stage spur gear set is made up of the motor spur gear 138 and the driven spur gear 156. The two gears 138, 156 are rotationally coupled to each other within the spur gear housing 120 as shown. Further, the driving bevel gear 152 is operably coupled with the driven spur gear 156, with bearings 154, 158 positioned on either side of the spur gear 156, thereby creating the spur/bevel assembly 150. The spur gear 156 is rotationally coupled to the bevel gear 152 such that neither the spur gear 156 nor the bevel gear 152 can rotate in relation to each other. In one embodiment, the two gears 156, 152 are rotationally coupled using a D-shaped geometric feature. The spur gear 156 is translationally constrained by the supporting bearings 154, 158, which are preloaded through screw 160. The fully assembled assembly 150 can be positioned in the lumen 151 in motor housing 120.

As shown in FIGS. 15A, 15B, 16A, 16B, 17A, 17B, and 17C, the third stage bevel gear set is made up of a drive bevel gear 152 and a link bevel gear 170. As discussed above, the drive bevel gear 152 is part of the spur/bevel assembly 150 and thus is operably coupled to and driven by the spur gear 156.

Setting aside for a moment the focus on the motor assembly 142 and related components coupled thereto (and the fact that the description relating to the assembly 142 and related components applies equally to the motor assembly 143), it is understood that there are two link bevel gears 170A, 170B positioned at opposite ends of the upper arm 30A, as best shown in FIGS. 11A, 11B, and 11C. The link bevel gear 170A operably couples the upper arm 30A to the device body 10, while the link bevel gear 170B operably couples the upper arm 30A to the forearm 30B.

Figure 16A:
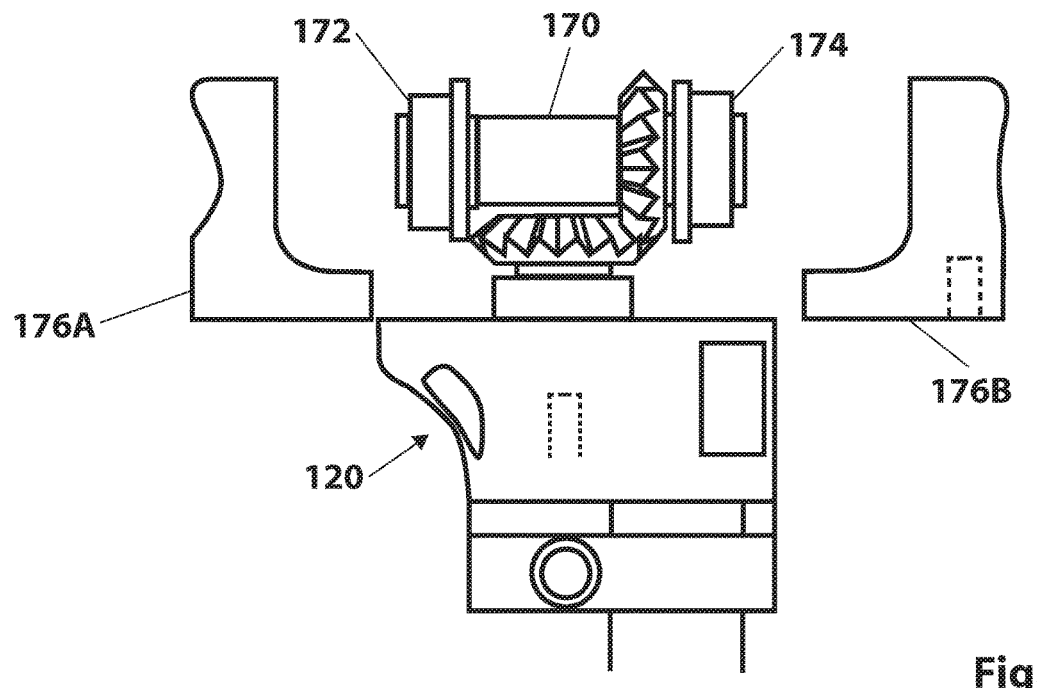
FIG. 16A is a side view of a portion of an upper arm, according to one embodiment.
Figure 16B:
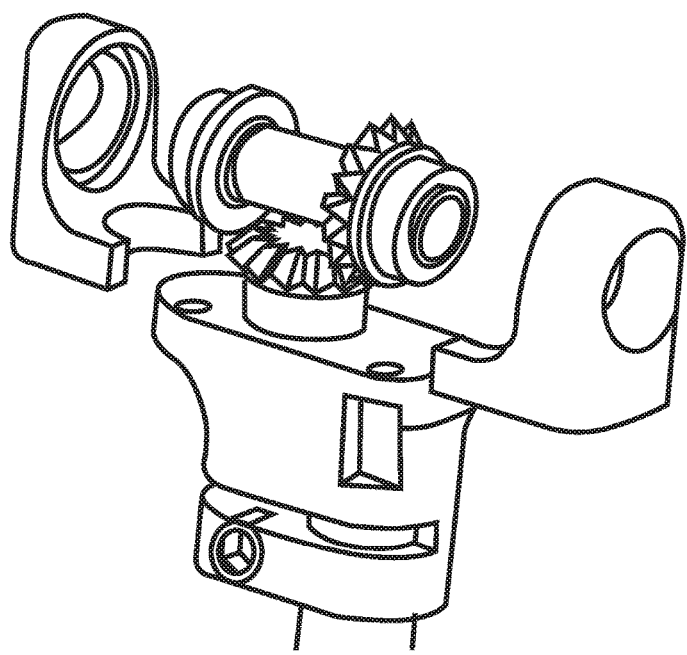
FIG. 16B is a perspective view of the portion of the upper arm in FIG. 16A.
Figure 17A:
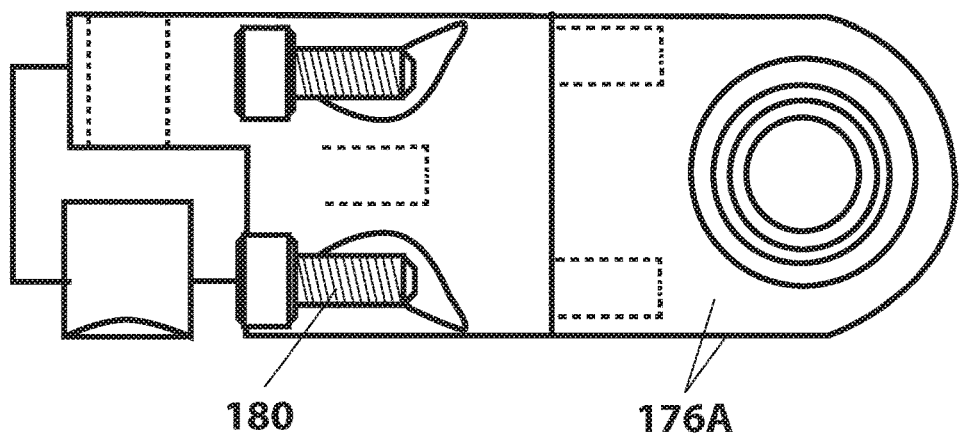
FIG. 17A is a side view of a portion of an upper arm, according to one embodiment.
Figure 17B:
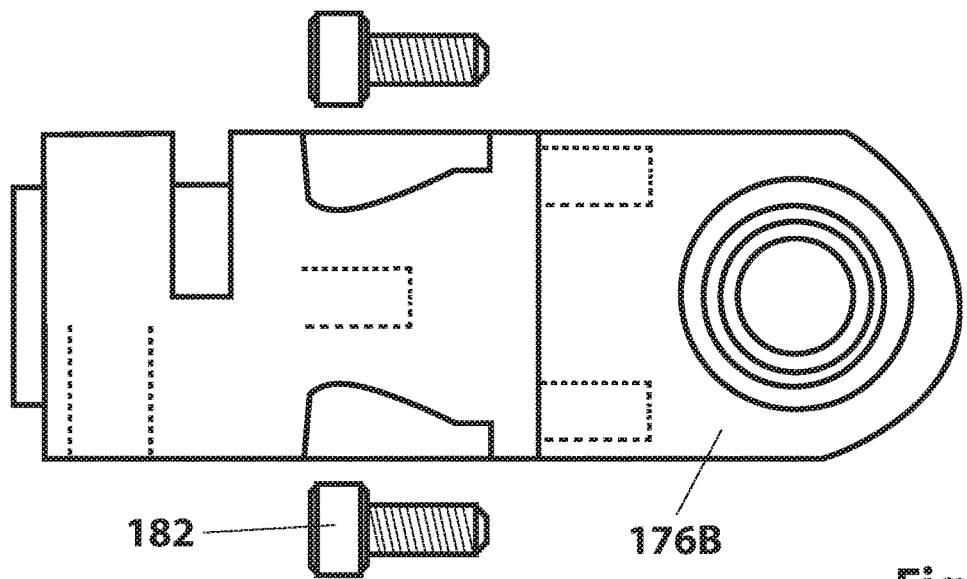
FIG. 17B is another side view of the portion of the upper arm in FIG. 17A.
Figure 17C:
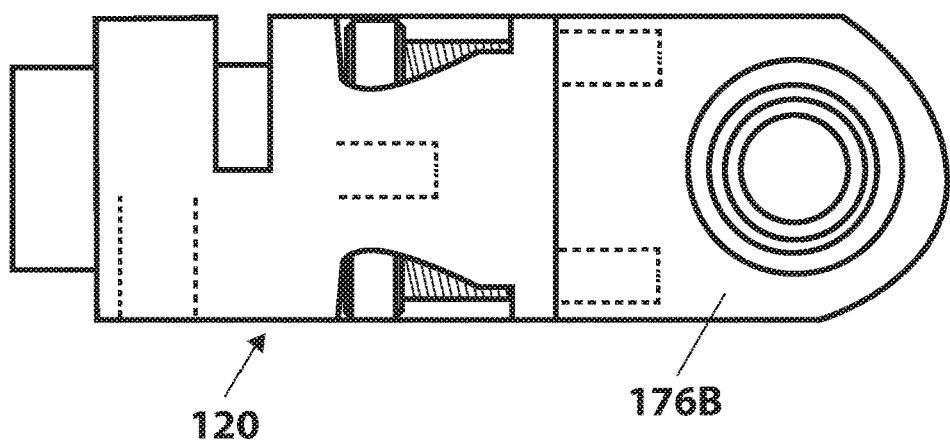
FIG. 17C is another side view of the portion of the upper arm in FIG. 17A.

Returning to FIGS. 15A-17C, the bearings 172, 174 support the link bevel gear 170. As best shown in FIGS. 16A and 16B, the bearings 172, 174 are supported by the bearing housing 176, which is made up of two housing projections 176A, 176B. The bearing housing 176 can apply a preload force to the bearings 172, 174. As best shown in FIGS. 17A-17C, the housing projections 176A, 176B are secured to the motor housing 120 by screws 180, 182, which are threadably coupled through the motor housing 120 and into the housing projections 176A, 176B.

As discussed above, it is understood that the above description relating to the upper arm 30A also applies to upper arm 20A as well. That is, in certain embodiments, the upper arm 30A and upper arm 20A are substantially the same.

FIGS. 18A-21C depict one implementation of a grasper forearm component 200 (which could, of course, be the forearm 30B discussed and depicted above) that can be coupled to the upper arm 30A. More specifically, the forearm 30B has an opening 218 defined at a proximal end of the arm 200 that is configured to be coupled to the link bevel gear 170B as discussed above. This forearm 200 has a grasper end effector (also referred to herein as a "manipulation end effector") 256 discussed in further detail below.

Figure 18A:
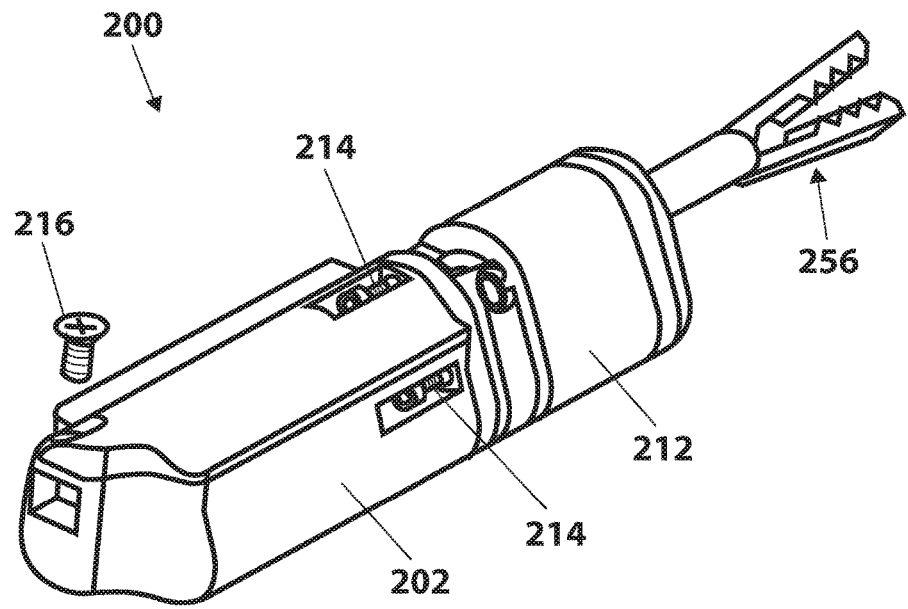
FIG. 18A is a perspective view of a forearm, according to one embodiment.
Figure 18B:
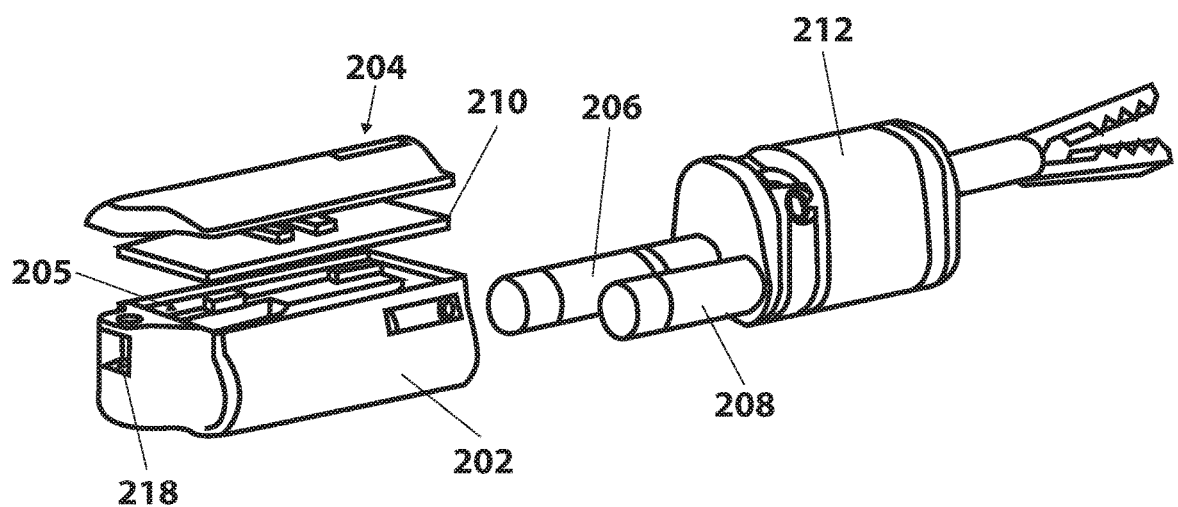
FIG. 18B is a different perspective view of the forearm in FIG. 18A.

As best shown in FIGS. 18A and 18B, in this embodiment, the grasper forearm 200 has a motor housing 202 coupled to a gear housing 212. The two housings 202, 212 contain two motor assemblies 206, 208, which actuate rotation of the grasper end effector 256 and opening/closing of the grasper 256, as described in further detail below. The motor housing 202 also contains the local control board 210 and has a housing cover (also referred to as a "cap") 204 configured to removably cover the opening 205 that provides access to the interior of the motor housing 202. The cover 204 can be coupled to the housing 202 with screw 216. In addition, the screw 216 is threadably positioned into the opening 218 and thus can be threadably coupled to the link bevel gear 170 as discussed above, thereby rotationally coupling the forearm 200 to the upper arm 30A. The motor housing 202 and cover 204 are coupled to the gear housing 212 with screws 214, which are threadably coupled through openings in the housing 202 and cover 204 and into the gear housing 212. In one implementation, the local control board 210 can be the same or similar to the local control board 132 in the upper arm as described above. The board 210 is coupled to the local control board 132 via the flexible electrical ribbon cable 136 in the upper arm 30A as described above.

Figure 19A:
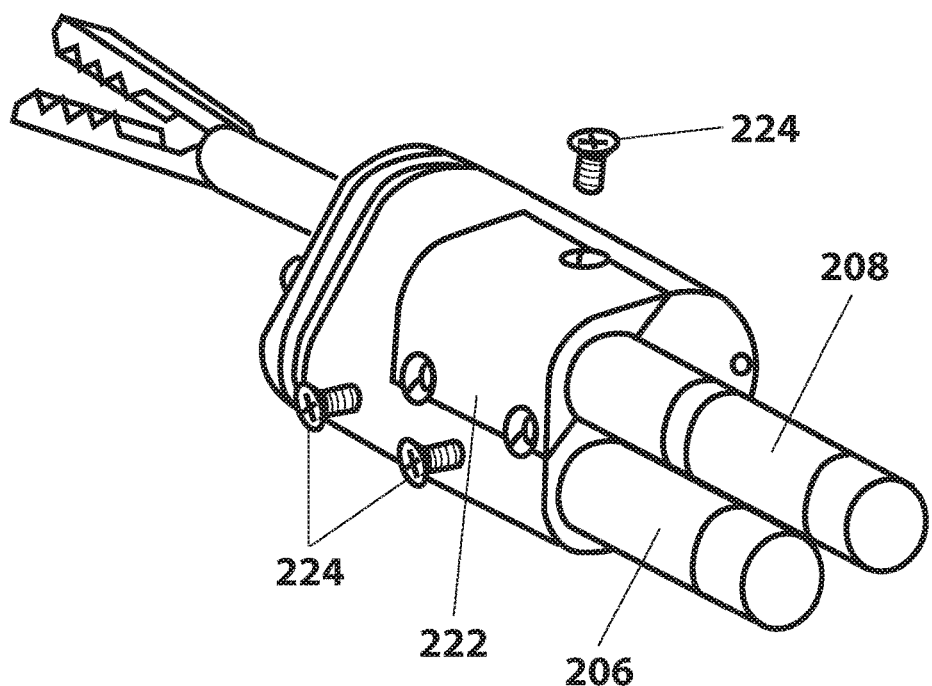
FIG. 19A is a perspective view of a portion of a forearm, according to one embodiment.
Figure 19B:
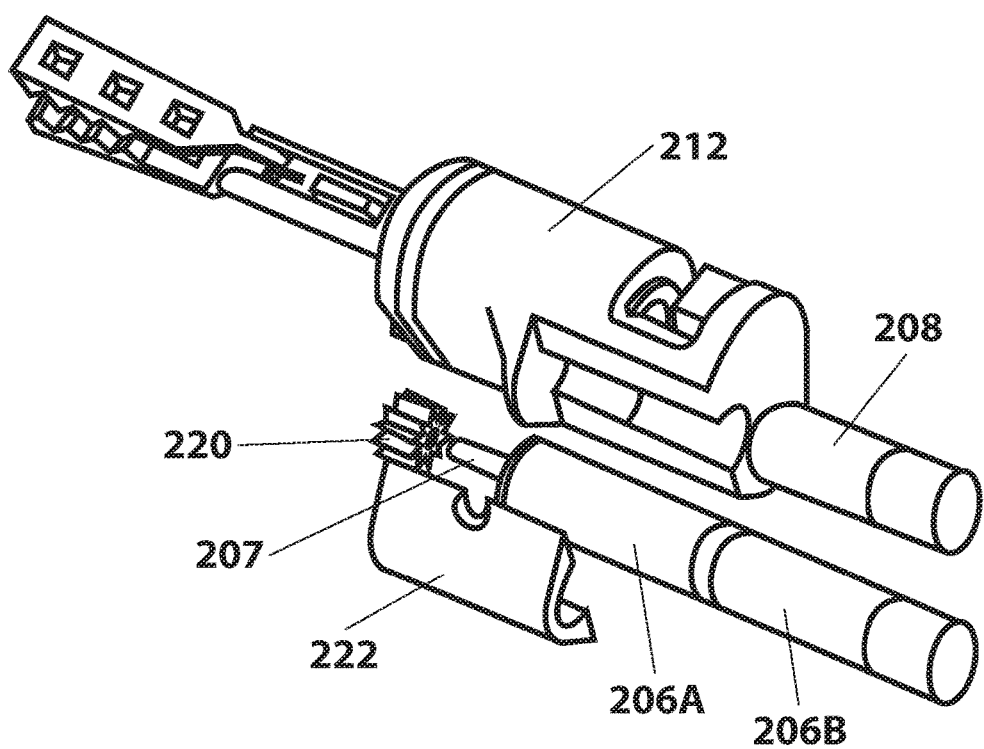
FIG. 19B is a different perspective view of the forearm in FIG. 19A.
Figure 20A:
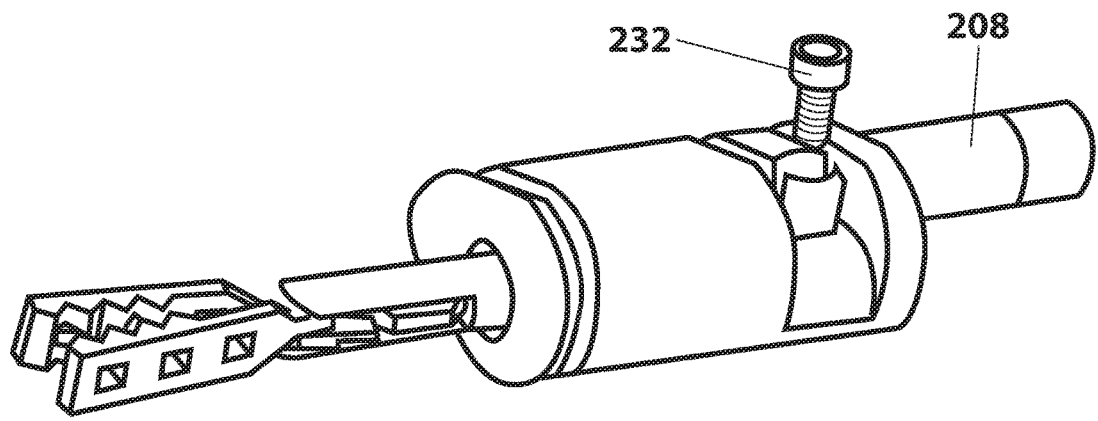
FIG. 20A is a perspective view of a portion of a forearm, according to one embodiment.
Figure 20B:
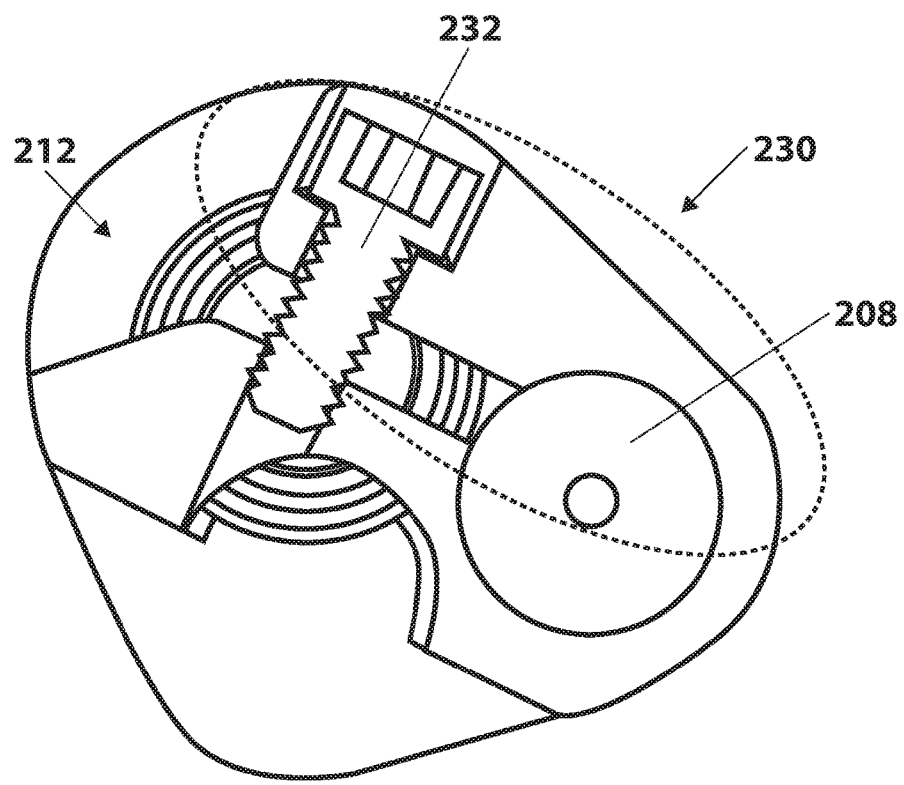
FIG. 20B is a cross-section view of the forearm in FIG. 20A.

As best shown in FIGS. 19A-20B, the two motor assemblies 206, 208 are coupled to the gear housing 212 via clamps 222, 230. More specifically, the motor assembly 206 is coupled to the housing 212 with the clamp 222 as best shown in FIGS. 19A and 19B, while the motor assembly 208 is coupled to the housing with the clamp 230 as best shown in FIGS. 20A and 20B. Alternatively, the assemblies 206, 208 can be secured to the housing 212 via adhesive or any other known coupling or securement mechanisms or methods.

As best shown in FIGS. 19A and 19B, the clamp 222 is coupled to the gear housing 212 with screws 224, which are threadably positioned through holes in the clamp 222 and into the gear housing 212. According to one embodiment, the clamp 222 secures the motor assembly 206 by frictional force applied by urging the clamp 222 against the housing 212 with the screws 224. As best shown in FIG. 19B, the motor assembly 206 contains two parts: a motor 206B and gear head 206A. In accordance with one implementation, the gear head 206A is operably coupled to the motor 206B. A drive gear (which is also a "spur gear") 220 is operably coupled to the shaft 207 extending from the motor assembly 206. In one embodiment, the shaft 207 has a flat portion resulting in a "D shaped" geometry, and the gear 220 has a hole that mates that geometry, thereby ensuring that the shaft 207 and gear 220 are not rotatable in relation to each other when they are coupled. In a further alternative, the gear 220 is also adhesively coupled to the shaft 207 with JB Weld or any known adhesive material. Alternatively, the gear 220 and shaft 207 can be coupled in any known fashion using any known coupling mechanism or configuration.

As best shown in FIGS. 20A and 20B, the clamp 230 is urged toward the housing 212 with screw 232, thereby creating frictional retention of the motor assembly 208. As such, the clamp 230 can retain the assembly 208 in the housing 212.

Figure 21A:
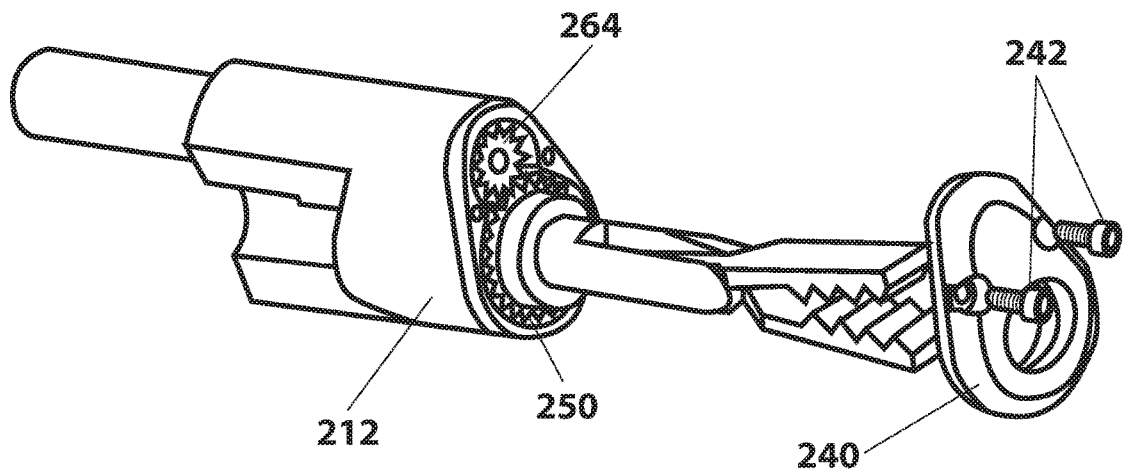
FIG. 21A is a perspective view of a portion of a forearm, according to one embodiment.
Figure 21B:
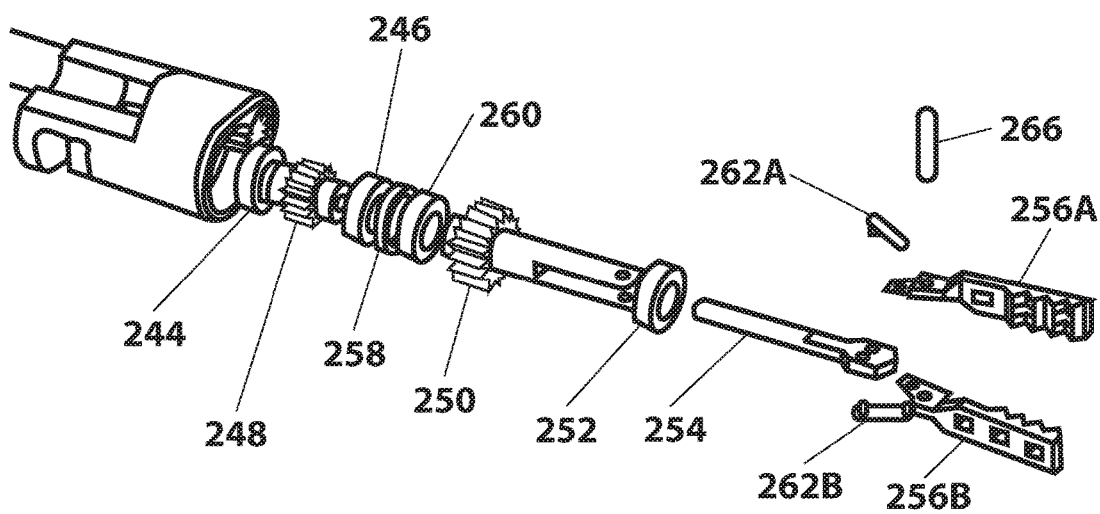
FIG. 21B is a different perspective view of the forearm in FIG. 21A.
Figure 21C:
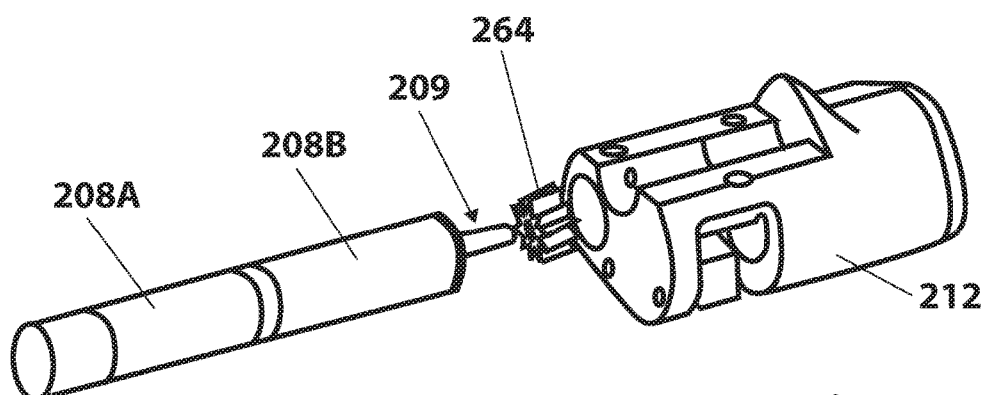
FIG. 21C is a different perspective view of the forearm in FIG. 21A.

As best shown in FIG. 21C, the motor assembly 208 has two parts: a motor 208A and a gear head 208B coupled to the motor 208A. A drive gear (which is also a "spur gear") 264 is operably coupled to the shaft 209 extending from the motor assembly 208. In one embodiment, the shaft 209 has a flat portion resulting in a "d shaped" geometry, and the gear 264 has a hole that mates that geometry, thereby ensuring that the shaft 209 and gear 264 are not rotatable in relation to each other when they are coupled. In a further alternative, the gear 264 is also adhesively coupled to the shaft 209 with JB Weld or any known adhesive material. Alternatively, the gear 264 and shaft 209 can be coupled in any known fashion using any known coupling mechanism or configuration.

As best shown in FIG. 21A, drive spur gear 264 is coupled in the gear housing 212 with driven spur gear 250, and actuation of the drive spur gear 264 (and thus the driven spur gear 250) causes the grasper end effector 256 to rotate. Further, as best shown in FIGS. 19B and 21B, the drive spur gear 220 is coupled in the gear housing 212 with driven spur gear 248, and actuation of the drive spur gear 220 (and thus the drive spur gear 248) causes the grasper end effector 256 to move between its open and closed positions.

Continuing with FIG. 21A, the gear housing 212 has a bearing cover (also referred to as a "cap") 240, which is attached to the gear housing 212 by screws 242 which are threadably coupled through holes in the cover 240 and into the gear housing 212. The screws 242 can also be configured to apply a preload force to bearings 244, 246, 260, 252. As shown in FIG. 21B, the bearings 244, 246, 260, 252 are supported within the gear housing 212. Bearings 244, 246 support the driven spur gear 248 of the end effector actuation spur gear set 220, 248.

Continuing with FIG. 21B, the spur gear 248 has a lumen with internal threads formed in the lumen and thus can be threadably coupled to the grasper drive pin 254, which can be positioned at its proximal end in the lumen of the spur gear 248. As the spur gear 248 rotates, the threads in the lumen of the spur gear 248 coupled to the threads on the drive pin 254 cause the drive pin 254 to translate, thereby causing the grasper links 256 to move between open and closed positions. In this particular embodiment, translation of the drive pin 254 is transferred through a four bar linkage made up of links 262A, 262B and grasper links 256A, 256B. Alternatively, this actuation of the grasper 256 can be accomplished through any other known mechanisms such as a pin and slot or worm gear drive train. A pin 266 secures the four bar linkage 262A, 262B, 256A, 256B to the spur gear 250. The pin 266 is threadably coupled to spur gear 250.

The bearings 260, 252 support the driven spur gear 250. The driven spur gear 250 is coupled to the grasper 256 such that when spur gear 250 is rotated, the grasper 256 is rotated. To rotate the grasper 256 without also actuating the grasper to move between its open and closed positions, the spur gear 248 must rotate in the same direction and at the same speed as the spur gear 250. That is, as described above, the drive pin 254 is rotationally coupled to spur gear 250 (otherwise translation of the pin 254 is not possible) such that when spur gear 250 is rotated (to cause the end effector to rotate), the drive pin 254 is also rotated. Hence, if spur gear 248 is not also rotated in the same direction at the same speed as the spur gear 250, the drive pin 254 will translate, thereby causing the grasper 256 to open or close. As a result, to rotate the grasper 256 without opening or closing it, the spur gears 250 and 248 must rotate together. The spacer 258 can provide spacing between the bearings 246, 260 and can also transfer the preload force through each bearing within the assembly.

Figure 22A:
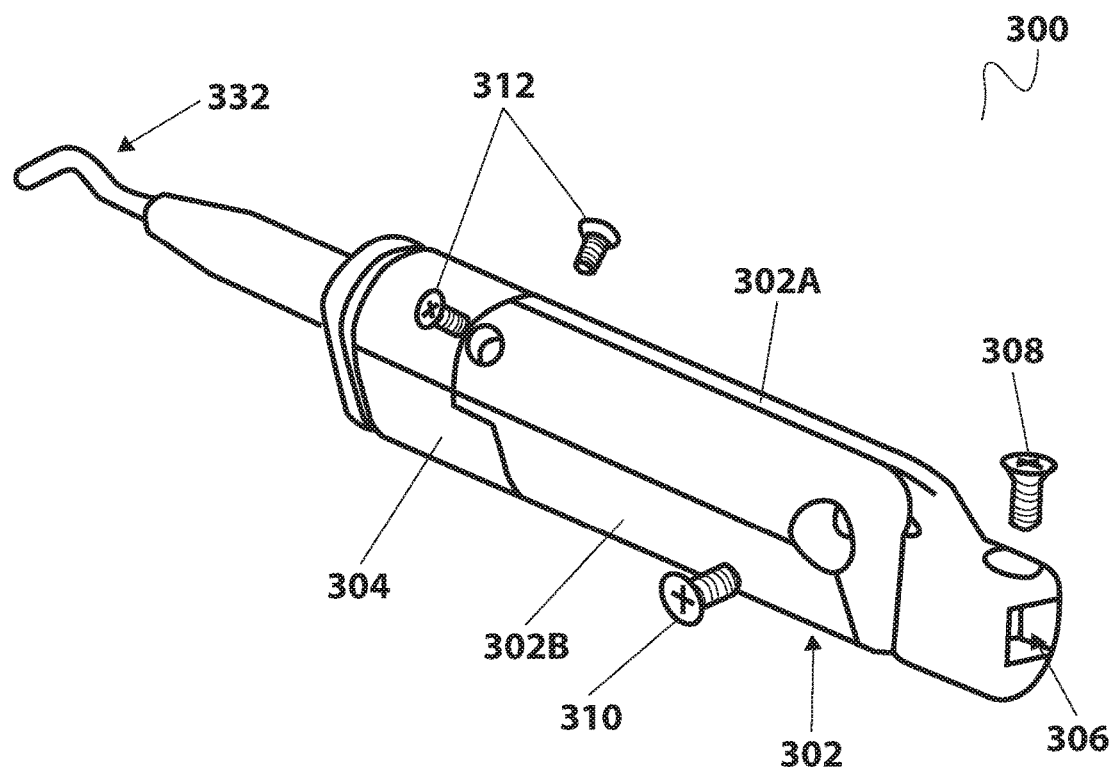
FIG. 22A is a perspective view of a forearm, according to one embodiment.

FIGS. 22A-24C depict an alternative embodiment relating to a cautery forearm component 300 (which could, of course, be the forearm 30B discussed and depicted above) that can be coupled to the upper arm 30A. More specifically, as best shown in FIG. 22A, the forearm 300 has an opening 306 defined at a proximal end of the arm 300 that is configured to be coupled to the link bevel gear 170B as discussed above. In one implementation, a screw 308 secures or threadably couples the link bevel gear 170B to motor housing 302A. This forearm 300 has a cautery end effector 332 that can be a monopolar electrocautery device as discussed in further detail below.

Figure 22B:
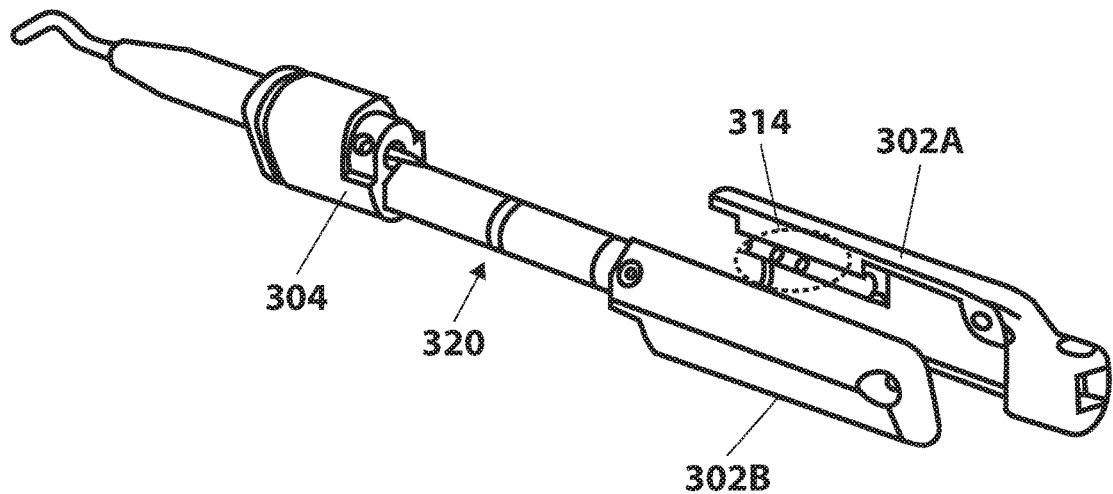
FIG. 22B is a different perspective view of the forearm in FIG. 22A.

As shown in FIGS. 22A and 22B, the forearm 300 is made up a motor housing 302 that is coupled to a gear housing 304. A motor assembly 320 is positioned within the motor housing 302 and gear housing 304. The motor housing 302 is actually made up of two housing components—a first motor housing component 302A and a second motor housing component 302B—that are coupled to each other to make up the housing 302. The first component 302A and second component 302B are secured to each other at least in part by the screw 310, which is inserted through holes in both components 302A, 302B and threadably coupled to both. The motor housing 302 is secured to the gear housing 304 via screws 312, which are positioned through holes in the motor housing 302 and into the gear housing 304.

As best shown in FIGS. 23A-24C, the motor assembly 320 is comprised of two parts: a motor 320B and a gear head 320A, which is operably coupled to the motor 320B. A drive gear (which is also a "spur gear") 324 is operably coupled to the shaft 322 extending from the motor assembly 320. In one embodiment, the shaft 322 has a flat portion resulting in a "d shaped" geometry, and the gear 324 has a hole that mates that geometry, thereby ensuring that the shaft 322 and gear 324 are not rotatable in relation to each other when they are coupled. In a further alternative, the gear 324 is also adhesively coupled to the shaft 322 with JB Weld or any known adhesive material. Alternatively, the gear 324 and shaft 322 can be coupled in any known fashion using any known coupling mechanism or configuration.

Figure 23A:
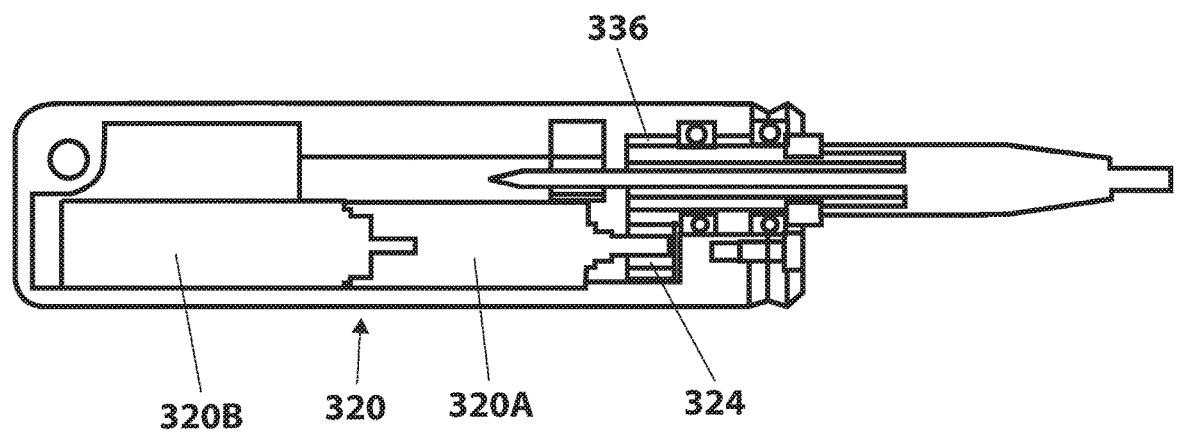
FIG. 23A is a cross-section view of a forearm, according to one embodiment.
Figure 23B:
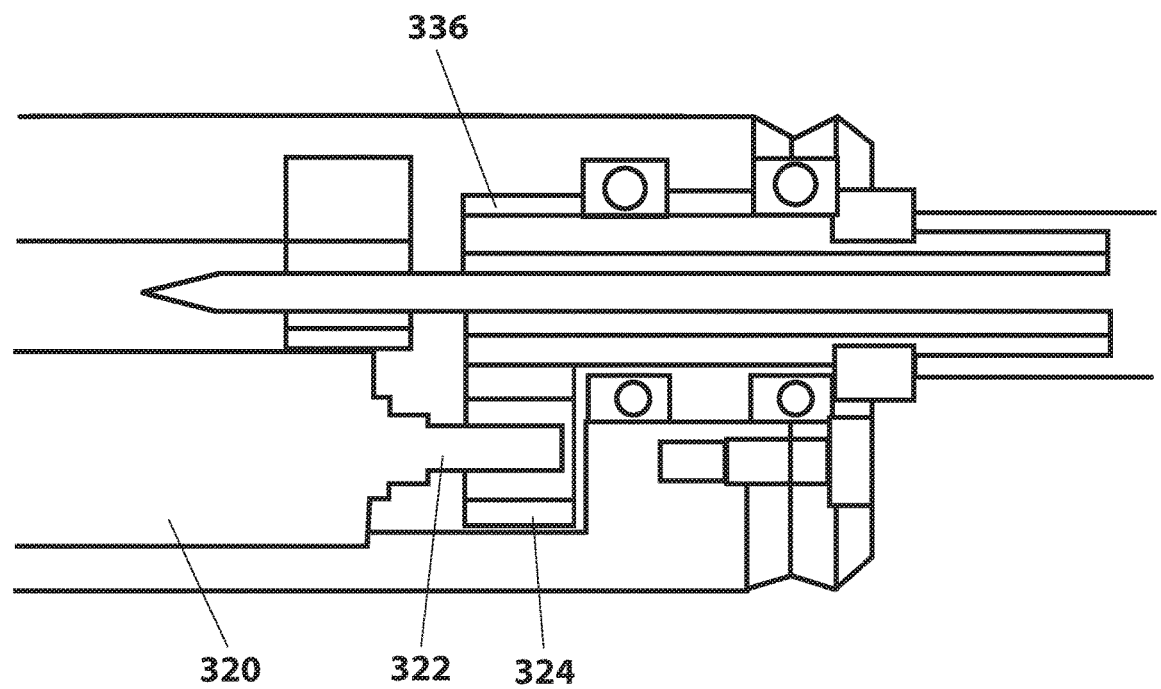
FIG. 23B is an expanded cross-section view of the forearm in FIG. 23A.
Figure 24A:
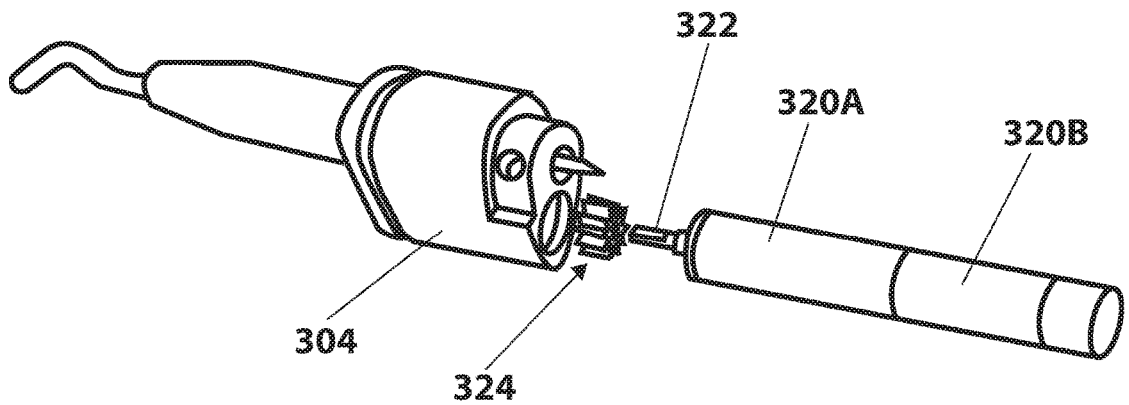
FIG. 24A is a perspective view of a portion of a forearm, according to one embodiment.
Figure 24B:
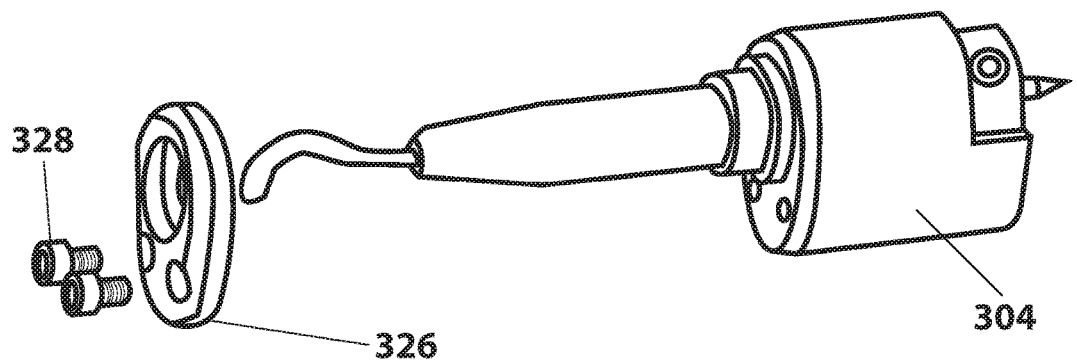
FIG. 24B is a different perspective view of the portion of the forearm in FIG. 24A.
Figure 24C:
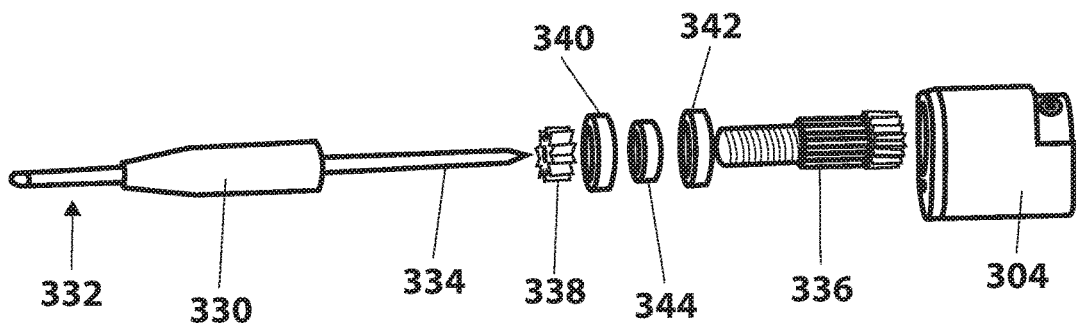
FIG. 24C is a different perspective view of the portion of the forearm in FIG. 24A.

As best shown in FIG. 24B, the gear housing 304 has a housing cover (also referred to as a "housing cap") 326 that is coupled to the distal portion of the gear housing 304 with screws 328 that are threadably coupled through holes in the cover 326 and into the gear housing 304. The housing cover 326 and screws 328 can, in some embodiments, apply a preload force to bearings 340, 342 positioned inside the housing 304 (as best shown in FIG. 24C). As best shown in FIGS. 23A and 23B, the drive spur gear 324 is operably coupled in the gear housing 304 to the driven spur gear 336. As shown in FIG. 24C, the driven spur gear 336 is operably coupled to the cautery end effector 332 and is supported by bearings 340, 342. The bearings 340, 342 are translationally fixed to the driven spur gear 336 by a nut 338 that is threadably coupled to the spur gear 336. The nut 338 does not apply a preload to the bearings 340, 342. In one embodiment, a spacer 344 is included to provide bearing spacing. The monopolar electrocautery end effector 332 is threadably coupled at a proximal end of the end effector 332 to the spur gear 336.

In use, electricity is transferred from the proximal tip 334 of the end effector 332 to the distal portion of the end effector 332 through a slip ring (not pictured) that is secured to the motor housing 302. In one embodiment, the slip ring is secured to a configuration 314 formed in the motor housing 302 as shown in FIG. 22B. The distal end of the end effector 332 is used to cauterize tissue.

In the embodiment described herein, the cautery forearm 300 has only one motor assembly 320 that has a two-stage gearhead. The first stage is the gear head 320A coupled to the motor 320B, and the second stage is the spur gear set made up of the drive spur gear 324 and the driven spur gear 336.

In accordance with one implementation, the cautery forearm component 300 does not contain a local control board. Instead, the component 300 can have a flexible electrical ribbon cable (not shown) operably coupled to the motor that connects to the local control in the upper arm (such as the local control board 132 in FIG. 11A). In one embodiment, the local control board in the upper arm (such as board 132, for example) can have one or more extra components to facilitate an additional motor. The single motor (not shown) in the cautery forearm component 300 can actuate rotation of the end effector 332.

FIGS. 25-29B depict yet another alternative embodiment of a cautery forearm component 400 (which could, of course, be the forearm 30B discussed and depicted above) that can be coupled to the upper arm 30A. This forearm 400 has a cautery end effector 402 that has an "inline" configuration that minimizes the overall cross-section of the forearm 400 and ultimately the robotic device to which it is coupled, thereby aiding in both surgical visualization and insertion. As described in further detail below, according to one embodiment, the inline configuration has a direct-drive configuration that enables the size of the forearm 400 to be reduced by almost half.

As best shown in FIGS. 25, 26A, 26B, and 28A, according to one implementation, the cautery end effector 402 is a removable cautery tip 402. The end effector 402 is removably coupled to the arm 400 at the drive rod 404. More specifically, in this embodiment, the end effector 402 has a lumen at its proximal end with threads formed on the inside of the lumen such that the threads 404A on the distal portion of the drive rod 404 can be threaded into the lumen in the end effector 402. The coupling of the end effector 402 and the drive rod 404 results in an electrical connection between the end effector 402 and the drive rod 404.

Figure 25:
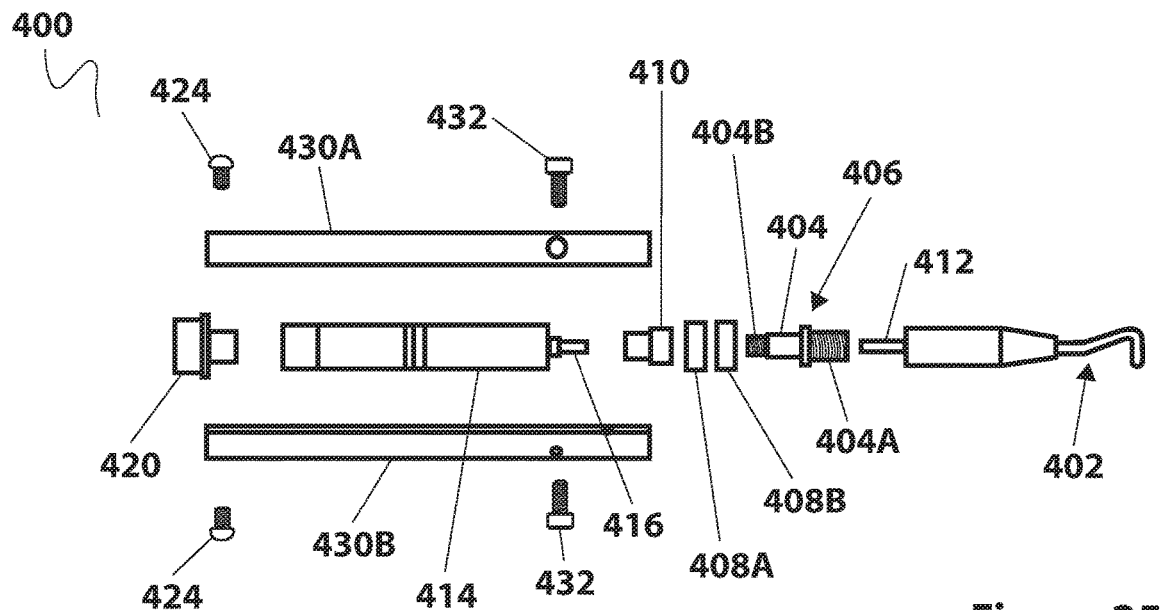
FIG. 25 is an exploded view of a forearm, according to one embodiment.
Figure 26A:
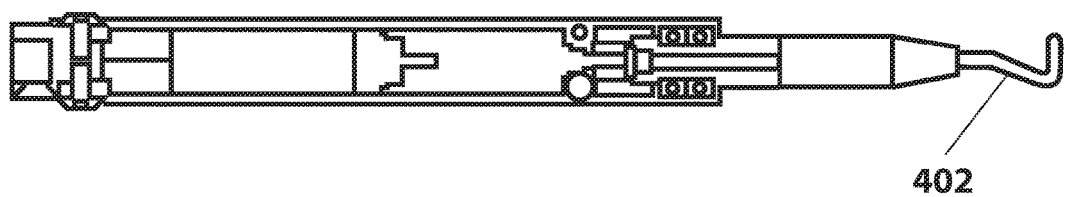
FIG. 26A is a cross-section view of a forearm, according to one embodiment.
Figure 26B:
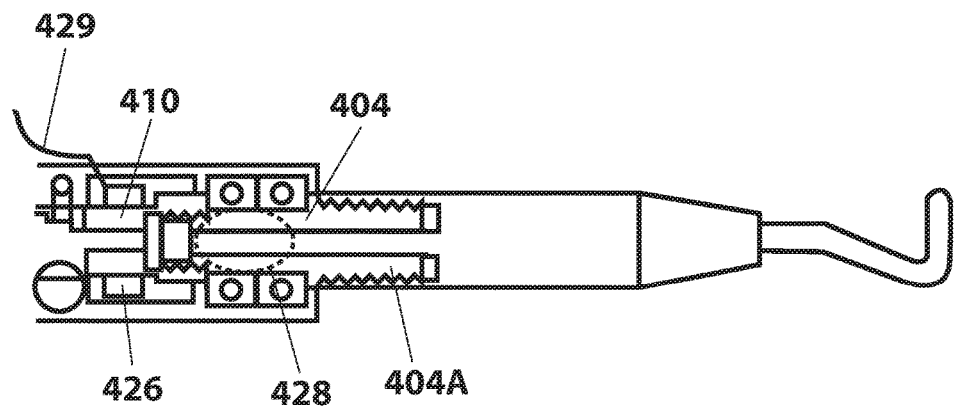
FIG. 26B is an expanded cross-section view of the forearm in FIG. 26A.
Figure 27A:
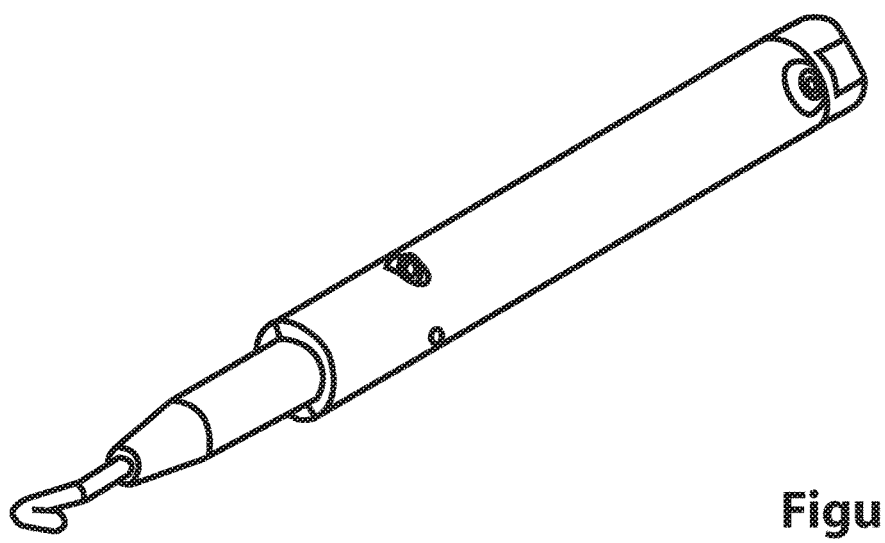
FIG. 27A is a perspective view of a forearm, according to one embodiment.
Figure 27B:
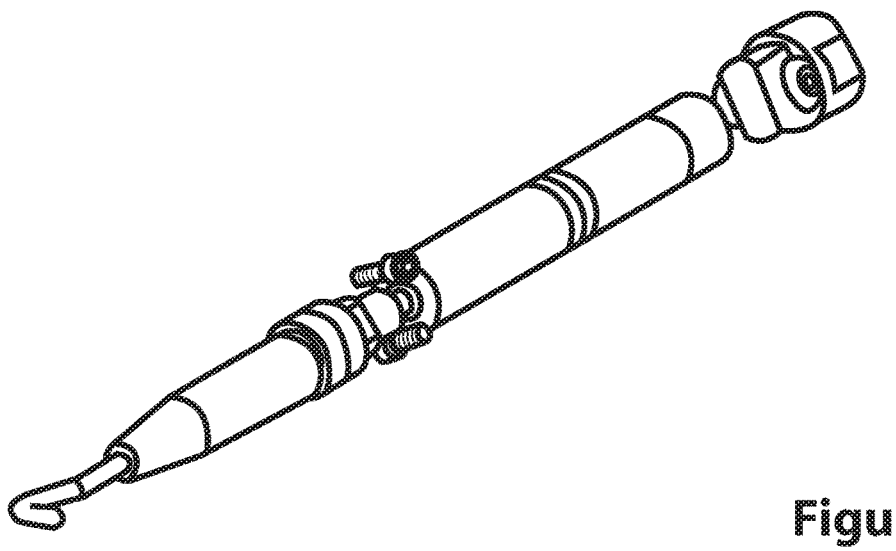
FIG. 27B is a different perspective view of the forearm in FIG. 27A.
Figure 27C:
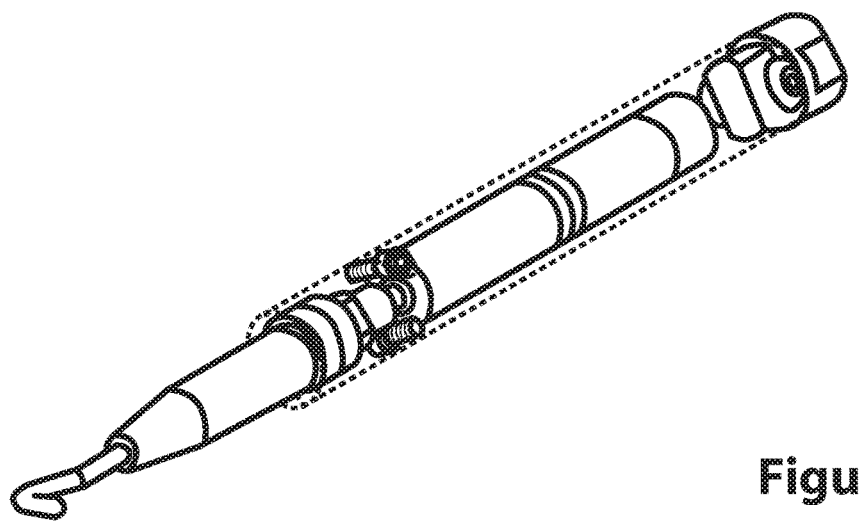
FIG. 27C is a different perspective view of the forearm in FIG. 27A.

As best shown in FIG. 26B, a first slip ring 426 electrically couples the monopolar cautery generator (the power source for the end effector 402, which is not shown) to the motor coupler 410. More specifically, the first slip ring 426 is coupled to a wire 429 that is coupled to the generator (not shown), thereby electrically coupling the ring 426 to the generator. Further, the slip ring 426 is secured to the body portions 430A, 430B (as best shown in FIG. 25 and discussed in further detail below) such that the ring 426 does not rotate in relation to the body 430. In contrast, the slip ring 426 is rotatably coupled to the motor coupler 410 such that the ring 426 and coupler 410 are electrically coupled and can rotate in relation to each other. The motor coupler 410 is threadably and electrically coupled to the drive rod 404. The cautery end effector 402 is coupled to the electrical cautery interface (also referred to herein as a "pin") 412. This pin 412 is coupled to the drive rod 404 via a second slip ring, which is positioned generally in the area identified as 428 in FIG. 26B, thereby ultimately resulting in an electrical connection between the end effector 402 and the first slip ring 426. In one embodiment, the second slip ring 428 is secured to the drive rod 404 or is a part of the drive rod 404. Alternatively, the slip ring 428 can be a separate component. This electrical connection of the first slip ring 426 to the end effector 402 through the motor coupler 410 enables transfer of the electrical energy to the end effector 402 that is necessary for cauterization. This is explained further below. According to one embodiment, the coupling of the end effector 402 and the drive rod 404 is maintained by the friction of the threadable coupling of the two components, along with the deformability of the end effector 402, which reduces the amount of force applied to that coupling. In accordance with one implementation, the end effector 402 has an o-ring at its distal end that helps to create a seal at the coupling to the drive rod 404 that inhibits inflow of biological material.

Alternatively, the end effector 402 can be non-removable. Instead, the end effector 402 can be integrated into the drive rod such that the need for the removable threaded connection would be eliminated. In such an embodiment, the second slip ring 428 could be replaced with a rigid electrical connection.

As best shown in FIGS. 25, 28A, 28B, 28C, and 28D, two bearings 408A, 408B are positioned over a proximal portion of the drive rod 404 and help to provide support to the end effector 402. The shoulder 406 on the drive rod 404 help to maintain the position of the bearings 408A, 408B in relation to the drive rod 404. In addition, the motor coupler 410 is threadably coupled to threads 404B on the proximal end of the drive rod 404 and thus also helps to retain the bearings 408A, 408B in place on the drive rod 404. The electrical connection discussed above extends through all three components: the motor coupler 410, the drive rod 404, and the end effector 402. According to one embodiment, as noted above, the pin 412 extending from the proximal portion of the end effector 402 (as best shown in FIGS. 25 and 26A) makes the electrical connection of the three components possible. This configuration of the three components allows for easy removal of one end effector 402 and replacement with another end effector 402 that is positioned such that the electrical connection is re-established by the simple threaded coupling of the new end effector 402 to the drive rod 404.

Alternatively, the bearings 408A, 408B can be replaced with other support components. One example would be bushings.

Figure 28A:
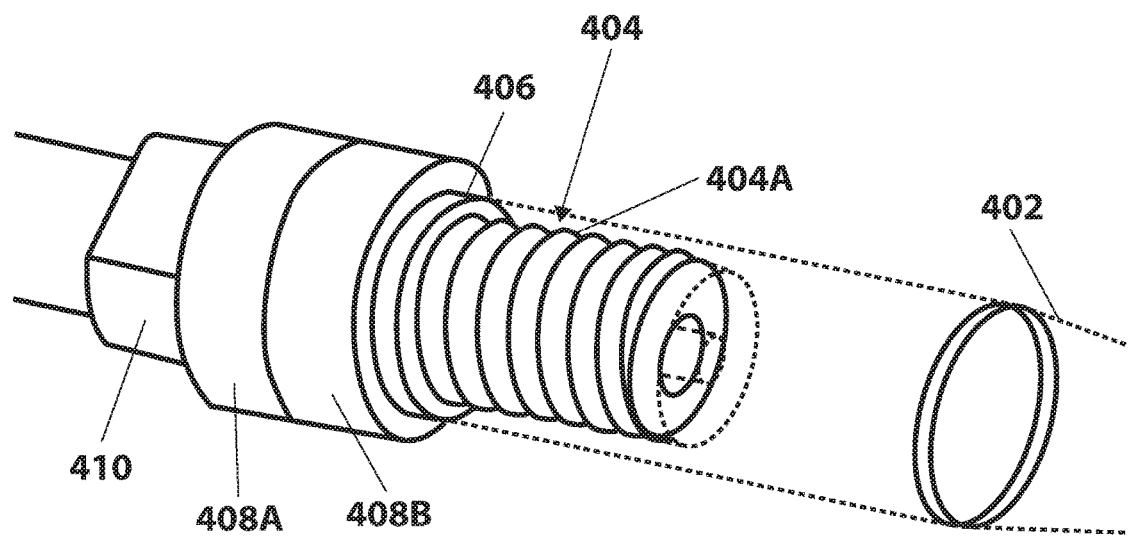
FIG. 28A is a perspective view of a portion of a forearm, according to one embodiment.
Figure 28B:
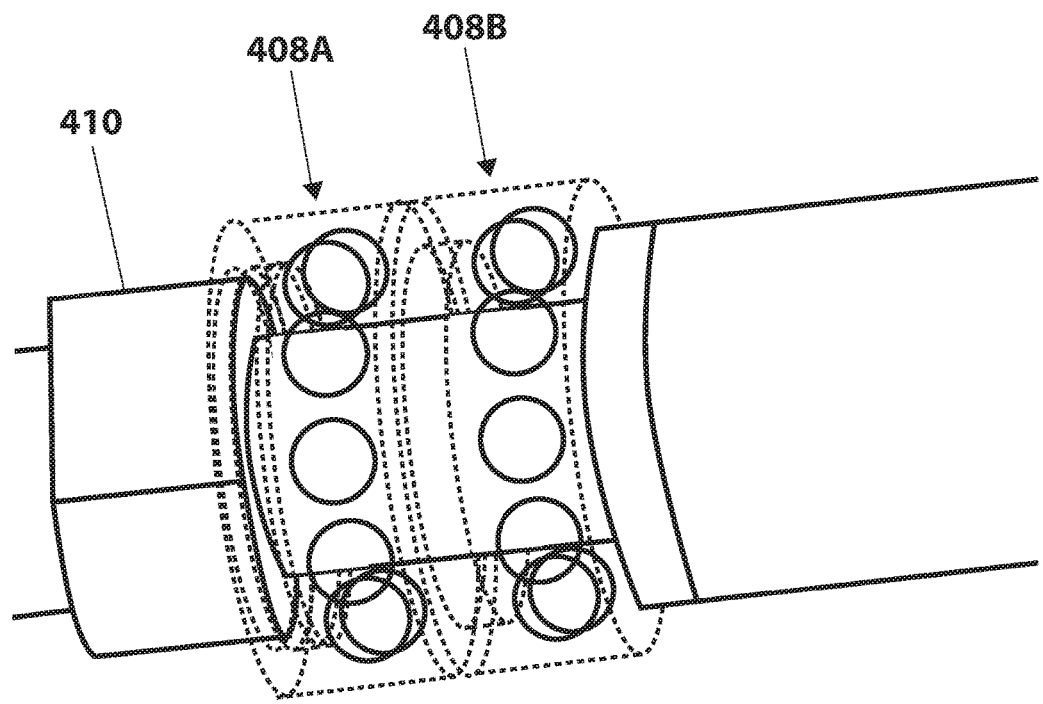
FIG. 28B is a different perspective view of the portion of the forearm in FIG. 28A.
Figure 28C:
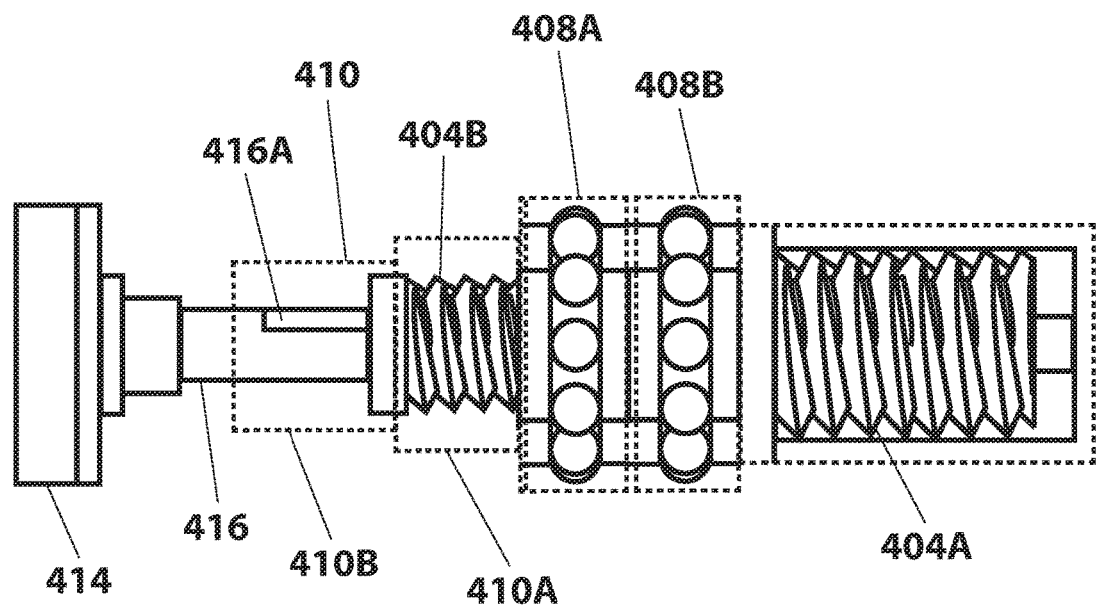
FIG. 28C is a different perspective view of the portion of the forearm in FIG. 28A.
Figure 28D:
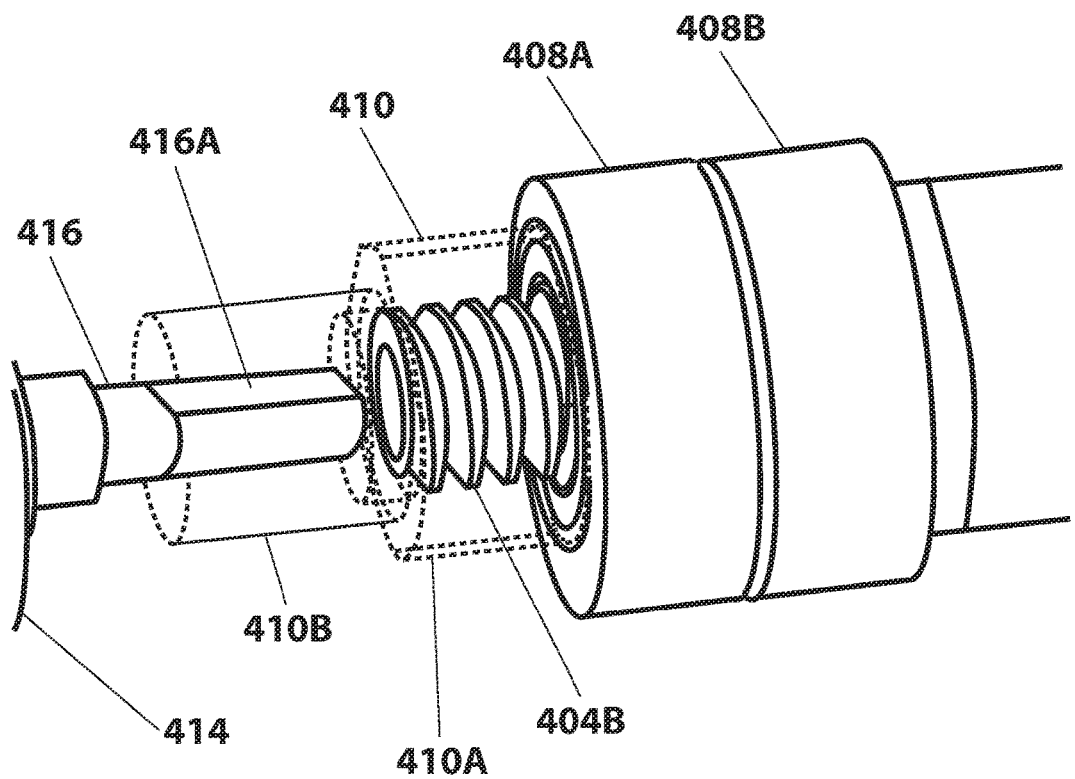
FIG. 28D is a different perspective view of the portion of the forearm in FIG. 28A.

Continuing with FIGS. 25, 28C, and 28D, the motor coupler 410 couples the motor assembly 414 to the end effector 402 through the drive rod 404. More specifically, the motor coupler 410 is coupled with the motor shaft 416 such that the coupler 410 is positioned over the shaft 416. In one embodiment, the motor shaft 416 has a flat portion 416A on the shaft that creates a "D-shaped" configuration and the motor coupler 410 has a corresponding "D-shaped" configuration that mates with the shaft 416 such that the shaft 416 and coupled 410 are not rotatable in relation to each other when they are coupled.

In accordance with one embodiment as best shown in FIGS. 28C and 28D, the motor coupler 410 has two portions with different diameters: a large portion 410A and a small portion 410B. The small portion 410B is sized to receive the first slip ring 426 discussed above that creates the necessary electrical connection. That is, as discussed above, when positioned over the small portion 410B of the motor coupler 410, the slip ring 426 can provide a constant clamping force on the motor coupler 410 that maintains the electrical connection between the motor coupler 410 and the motor shaft 416 during rotation. This type of connection (the slip ring) allows for infinite rotation without twisting of any wires. With respect to the coupling of the motor coupler 410 with the drive rod 404, the coupling in some implementations is reinforced or further secured with an adhesive. For example, the adhesive could be a Loctite® adhesive or any other known adhesive for use in medical device components.

Figure 29A:
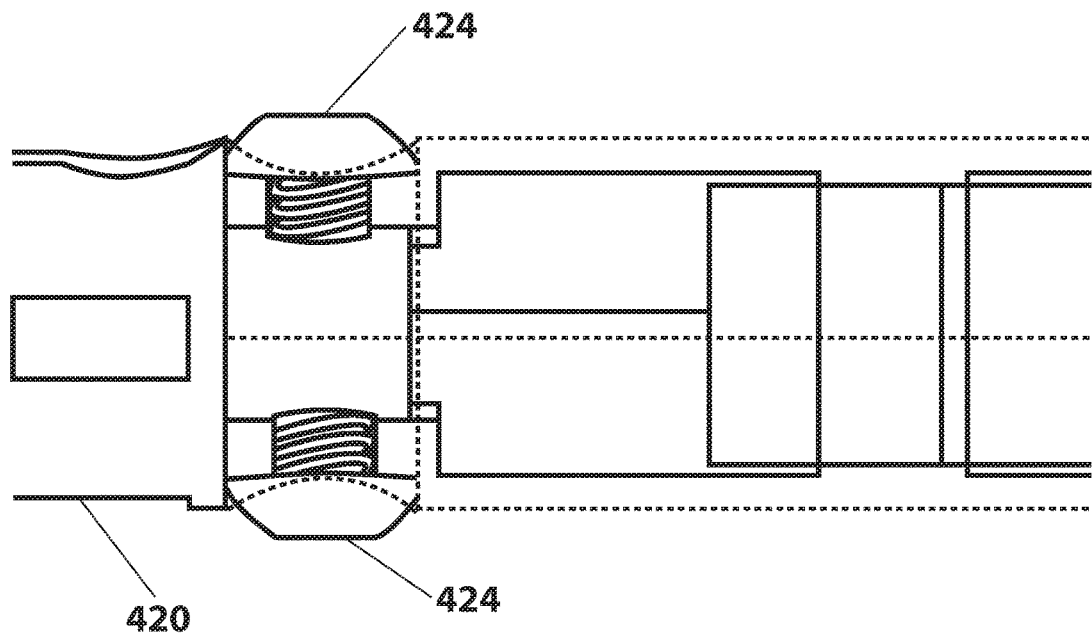
FIG. 29A is a side view of a portion of a forearm, according to one embodiment.
Figure 29B:
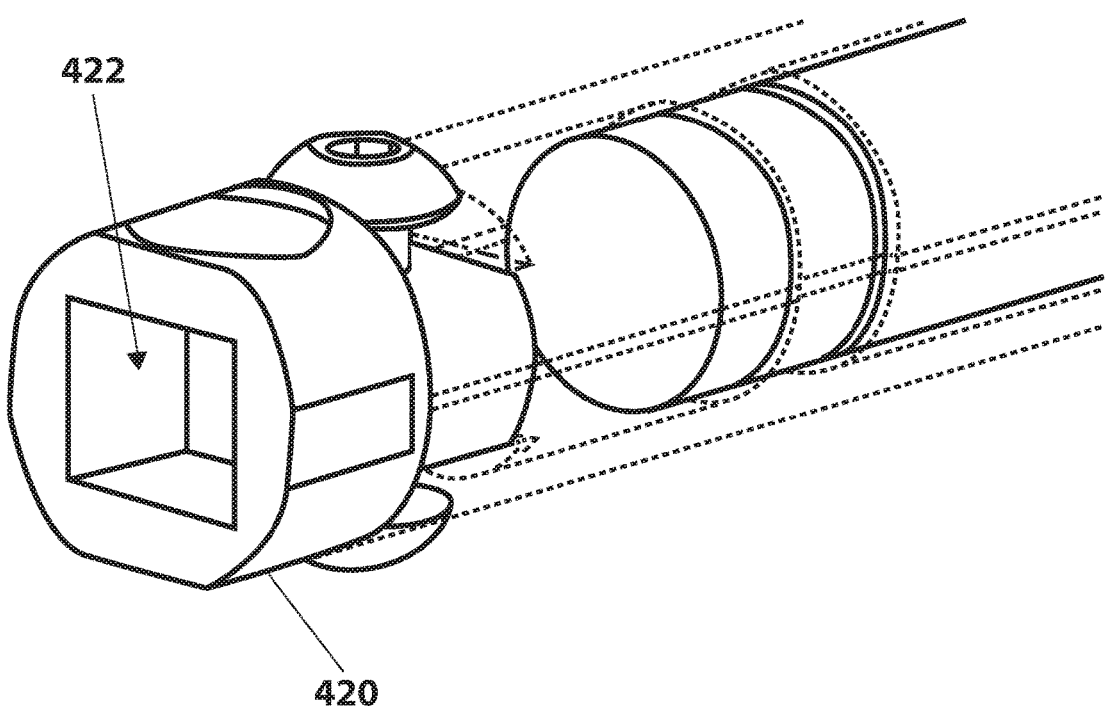
FIG. 29B is a perspective view of the portion of the forearm in FIG. 29A.

As best shown in FIGS. 29A and 29B, the proximal end of the forearm 400 has a coupling component 420 that allows for coupling the forearm 400 to the rest of the surgical system with which the forearm is incorporated. For example, in the device 10 depicted and discussed above, the coupling component 420 would be coupled to the upper arm 30A. The coupling component 420 is coupled to the proximal portion of the forearm 400 with two screws 424 that are positioned through holes in the forearm 400 and into a portion of the coupling component 420 as shown.

The coupling component 420 has an opening 422 defined in the component 420 (as best shown in FIG. 29B) that couples to the appropriate component of the surgical system. In this embodiment, the opening 422 is a rectangular-shaped opening 422, but it is understood that it could be any configuration of any type of coupling component or mechanism, depending on the system to which the forearm 400 is being coupled.

Alternatively, the coupling component 420 can be eliminated in those embodiments in which the forearm 400 is an integral part of the upper arm of a device or in any embodiment in which there is no forearm.

Returning to FIGS. 25 and 26A, the body 430 of the forearm 400 is made up of two body portions (also referred to as "shells") 430A, 430B. The two portions 430A, 430B are coupled together with the screws 432 and the aforementioned screws 424. According to one embodiment, each of the two body portions 430A, 430B have internal features as best shown in FIG. 26A that help to retain the motor assembly 414, bearings 408A, 408B, and other internal components in position with respect to each other inside the body 430. In one implementation, there is space provided within the body 430 to allow for inclusion of any excess wires. It is understood that additional components or mechanisms can be included on an outer portion of the portions 430A, 430B to aid in fluidically sealing the body 430. For example, in one embodiment, the interface of the portions 430A, 430B may have mating lip and groove configurations to provide a fluidic seal at the coupling of the two portions 430A, 430B.

Figure 30:
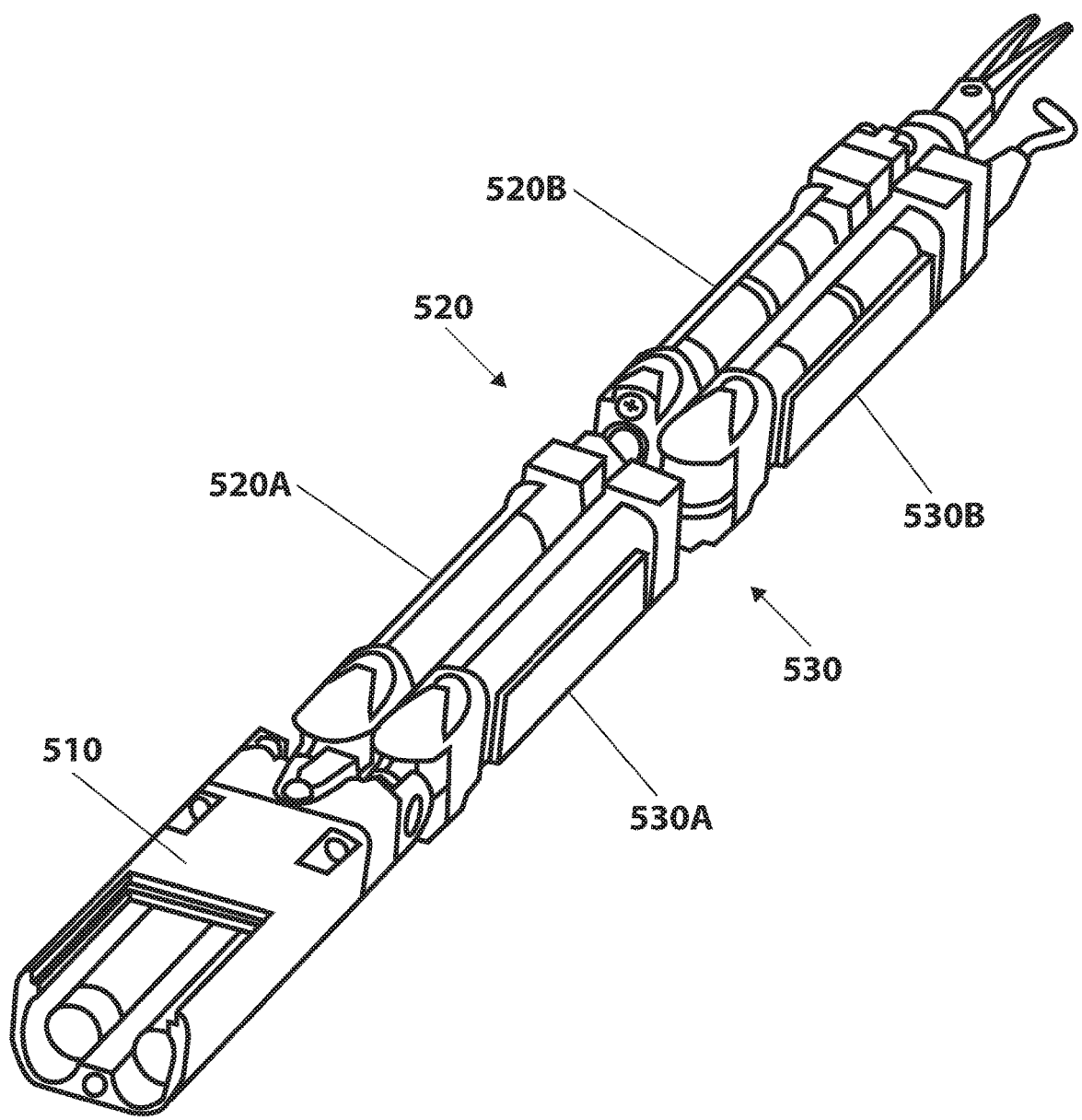
FIG. 30 is a perspective view a robotic medical device, according to one embodiment.

Another embodiment of a robotic device 500 is depicted in FIGS. 30-39B. This embodiment has a device body 510, a left arm 520, and a right arm 530, as shown in FIG. 30. Both the left and right arms 520, 530 are each comprised of 2 segments: an upper arm (or "first link") and a forearm (or "second link"). Thus, the left arm 520 has an upper arm 520A and a forearm 520B and the right arm 530 has an upper arm 530A and a forearm 530B.

In this embodiment, the robotic device 500 is similar in some respects to the device embodiment described above and depicted in FIGS. 1A-2. However, the current device 500 is unique because of its "clutch-like" joint configuration as described in detail below. To insert a device or platform in a NOTES procedure through a natural orifice, the device 500 needs to be very flexible to navigate the natural curvature of the natural orifice. The clutch-like joint configuration at each joint in this device 500 provides the device 500 with the necessary flexibility. According to one embodiment, this device 500 will be locally controlled by a control system similar to the system described above with respect to the previous embodiments.

Figure 32A:
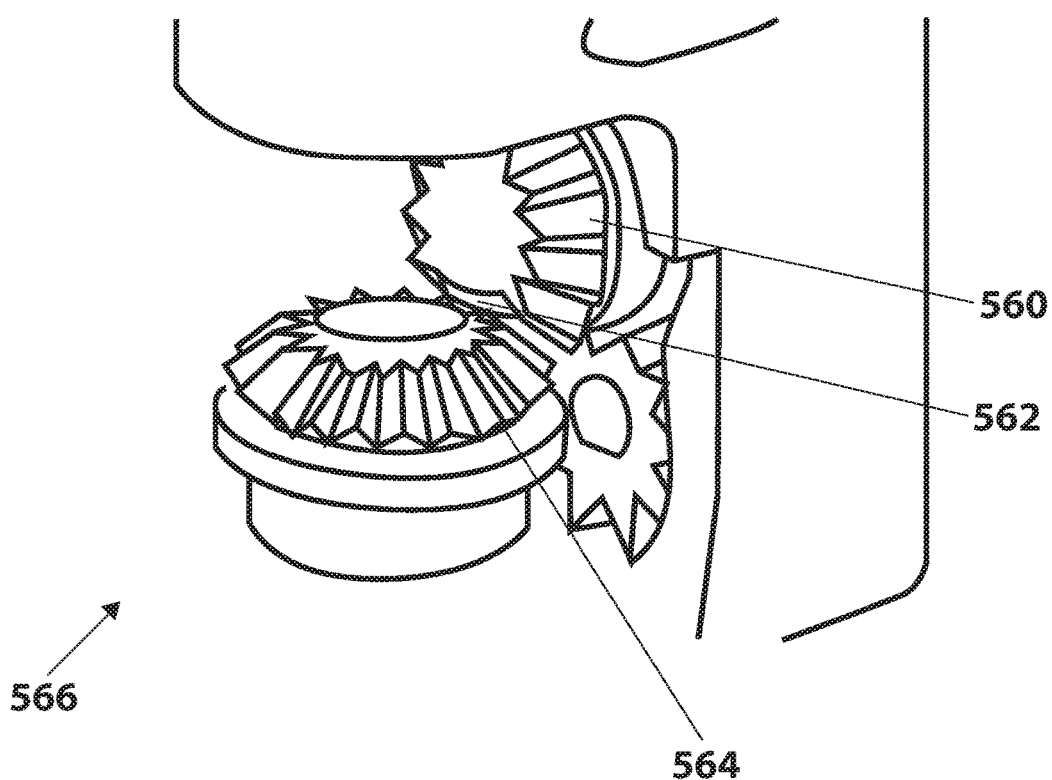
FIG. 32A is a perspective view of a joint of a medical device, according to one embodiment.
Figure 32B:
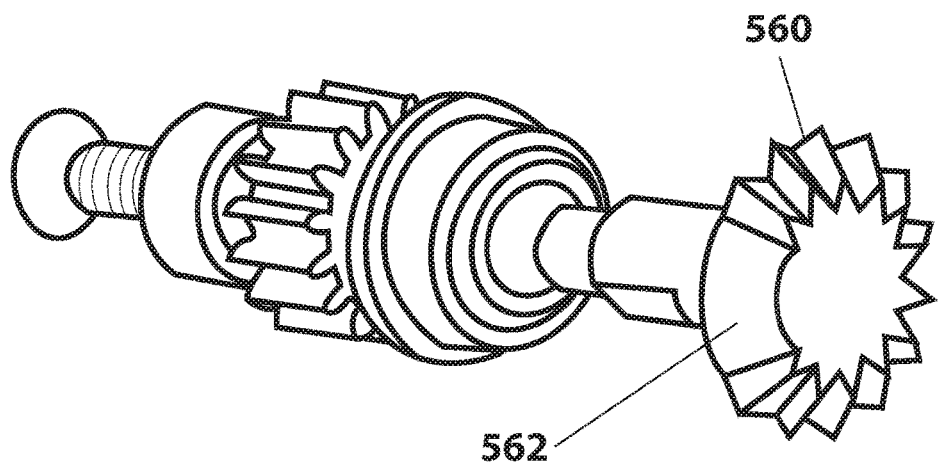
FIG. 32B is a perspective view of a gear from the joint of FIG. 32A.

The clutch-like configuration, according to one embodiment, is best shown in FIGS. 32A and 32B. As can be seen in these figures, the overall joint design is fairly similar to the joint design of the embodiments described above. However, in this embodiment, the drive bevel gear 560 has a portion 562 of the gear 560 that has no teeth. The tooth-free portion 562 creates the clutch-like configuration. That is, when the drive bevel gear 560 is positioned such that the tooth-free portion 562 is in contact with or adjacent to the driven gear 564 such that no teeth are engaged, the overall joint 566 is free to move and thus has flexibility that can be helpful during insertion.

Figure 31C:
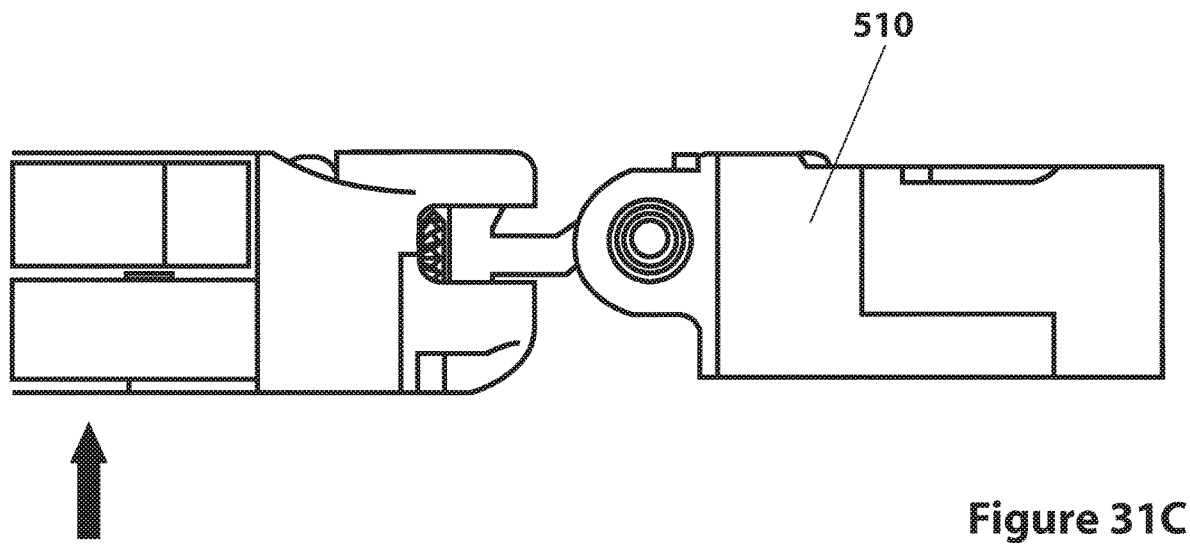
FIG. 31C is a side view of the portion of the device in FIG. 31B.

As best shown in FIGS. 31A, 31B, and 31C, this embodiment can also have one or more rubber band-like components (also referred to herein as "elastomers" or "elastic bands") 550 that can be used to keep each joint stabilized and thus each arm positioned to keep the robotic device 520 as compact as possible during insertion. In a further embodiment, the band(s) 550 can also keep the arms in the correct position for engagement of the bevel gears. More specifically, the device body 510 and the two upper arms 520A, 530A have a channel 552 formed on a top portion of each component as shown in FIG. 31B that is configured to receive the elastic band(s) 550. In certain embodiments, there are also bolts 554 positioned at strategic locations— such as, for example, the locations shown in FIG. 31B—to which the elastic band(s) 550 can be attached. In one implementation, the elastic band (or bands) 550 applies forces to the arms 520A, 530A that urge the arms 520A, 530A together as shown by the arrows in FIG. 31B while also urging both arms upward as shown by the arrow in FIG. 31C.

In one alternative embodiment, this clutch-like configuration could also be used for homing if the positioning of the arms 520, 530 is lost (that is, the joint positions are unknown). In that scenario, each of the drive bevel gears could be positioned so that they are not engaged, whereby the joint positions of the device 500 are known once again. In this embodiment, no additional redundant position sensors would be needed.

Figure 31D:
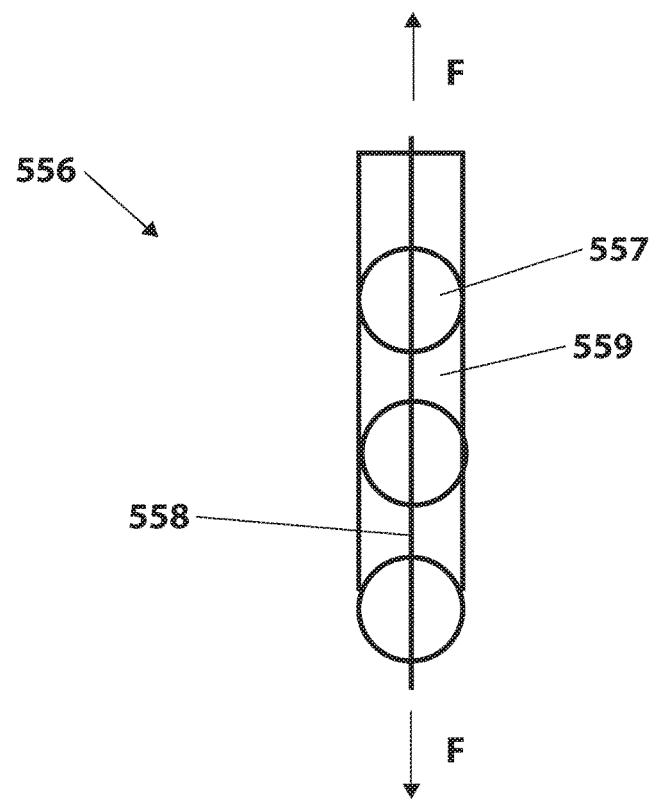
FIG. 31D is a side view of a portion of a medical device, according to another embodiment.

It is understood that other types of stabilization devices or mechanisms could also be used in place of the elastic bands 550. For example, in one alternative embodiment, two torsion springs could be used that are positioned opposite of each other, resulting in equal and opposite rotational forces. Alternatively, other known clutch-like devices or mechanisms could be used, including, for example, any commercially available or custom made clutch. In further alternatives, flexible links could be used in combination with solid bevel gears (no teeth missing). In such embodiments, the flexibility of the flexible links could be activated thermally (thermo plastic), electrically (shape memory alloy), or mechanically (friction based). FIG. 31D depicts one exemplary embodiment of a mechanically-activated link 556. The link 556 becomes flexible when a small force F is applied to the cable 558, thereby reducing the friction between the balls 557 and sockets 559 in the link 556 and thus creating flexibility in the link 556. In contrast, when a large force F is applied to the cable 558, friction is increased between the balls 557 and sockets 559 and the link 556 becomes more rigid.

Figure 33:
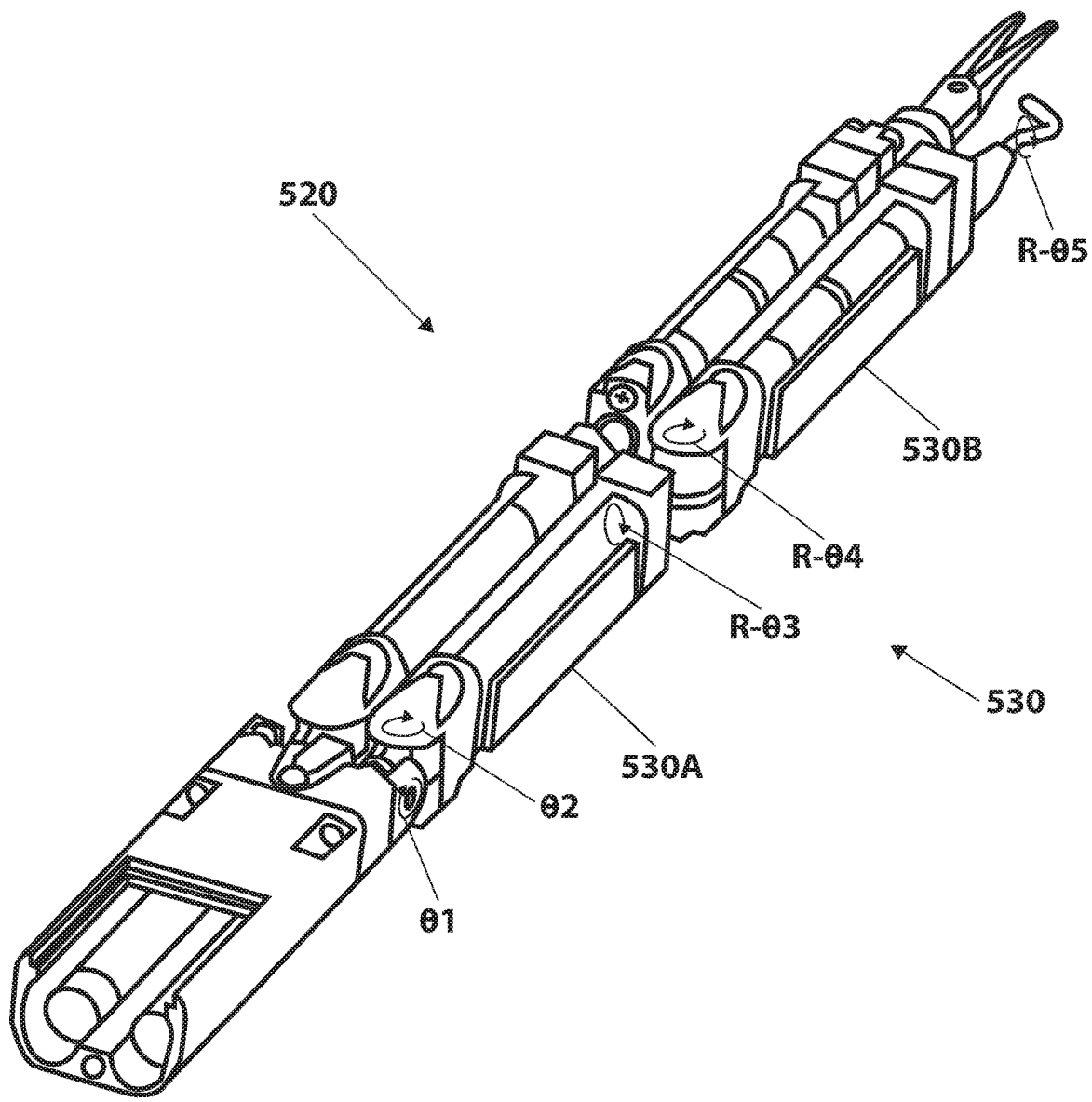
FIG. 33 is a perspective view of the medical device of FIG. 30.

FIG. 33 depicts the various degrees of freedom of the various joints of the two arms 520, 530. In this embodiment, the left arm 520 has four degrees of freedom, while the right arm 530 has five degrees of freedom. More specifically, moving from the proximal end of the right arm 530 to the distal end, the right arm 530 has shoulder pitch ($\theta 1$), shoulder yaw ($\theta 2$), elbow roll ($\theta 3$), elbow yaw ($\theta 4$), and end effector roll ($\theta 5$). In contrast, the left arm 520 has shoulder pitch, shoulder yaw, elbow yaw, and end effector roll, but no elbow roll. Alternatively, any other known kinematic configuration could also be used. The multiple degrees of freedom for each arm results in more dexterous arms for more precision operations.

Figure 34:
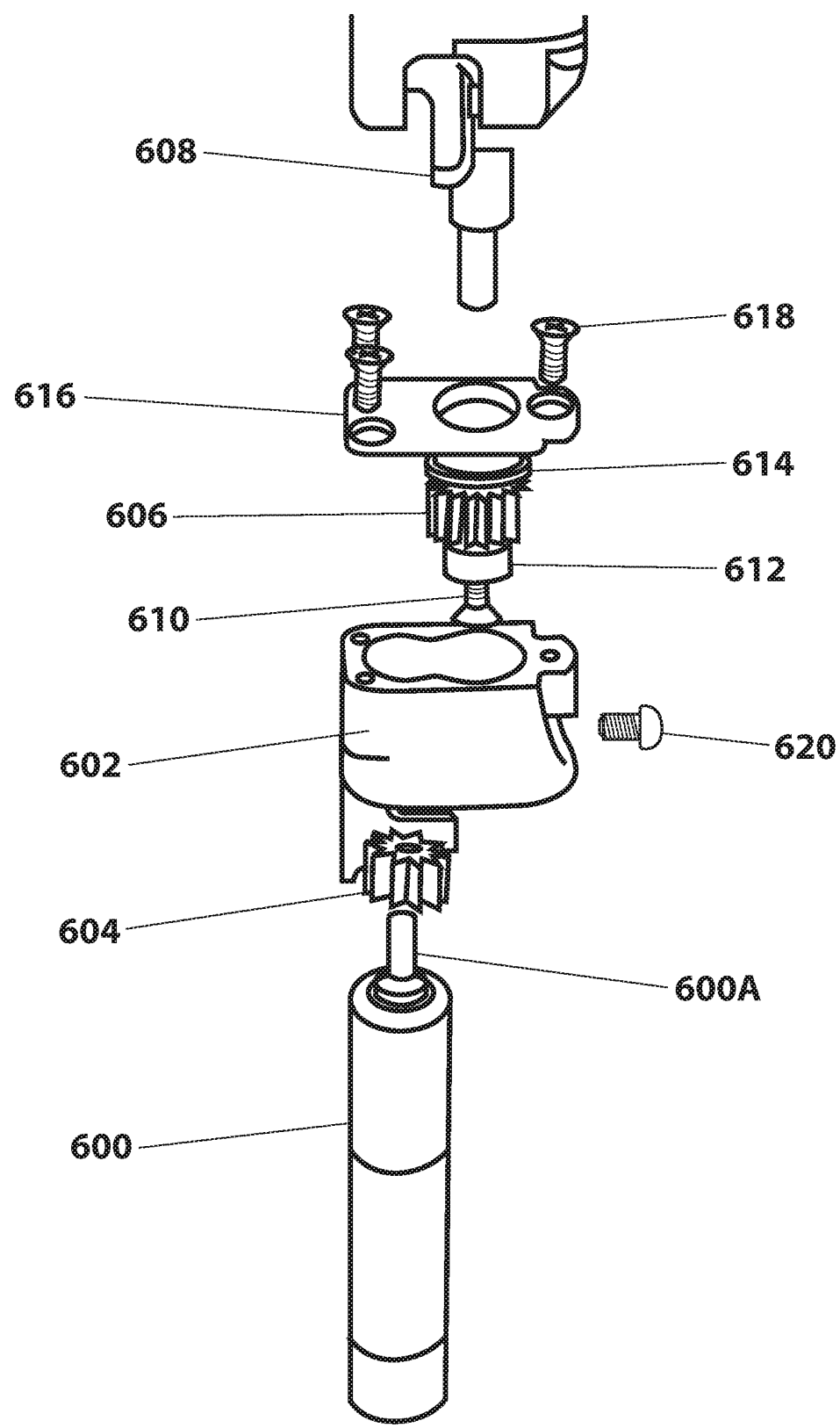
FIG. 34 is an exploded view of a forearm, according to one embodiment.

FIG. 34 depicts the key components that make up the joint (also referred to as an "elbow joint") between the upper arm 530A and the forearm 530B of the right arm 530. The upper arm 530A has a motor assembly 600 that includes a motor, an encoder, and a gearhead. The distal end of the motor assembly 600 is positioned in and coupled to the gear housing 602. In one embodiment, the motor assembly 600 has a flat portion along an exterior portion of the assembly 600 that creates a "D-shaped" configuration that matches a D-shaped configuration of a lumen in the gear housing 602 such that the assembly 600 and housing 602 cannot rotate in relation to each other when the assembly 600 is positioned in the lumen. In a further implementation, an adhesive can also be used to further secure the assembly 600 and housing 602.

The motor assembly 600 has a motor shaft 600A extending from the distal end of the assembly 600. The shaft 600A can be coupled to the motor spur gear 604 such that the spur gear 604 is positioned over the shaft 600A. In one embodiment, the shaft 600A has a flat portion that results in a "D-shaped configuration that matches a "D-shaped" configuration of the lumen in the spur gear 604 such that when the spur gear 604 is positioned over the shaft 600A, neither component can rotate in relation to the other. The motor spur gear 604 couples or mates with the driven spur gear 606 when the two gears are properly positioned in the gear housing 602 such that rotation of the motor spur gear 604 rotates the driven spur gear 606.

The driven spur gear 606 is coupled to the output link 608 such that actuation of the motor assembly 600 causes the output link 608 to rotate. More specifically, the driven gear 606 is positioned over the proximal end of the output link 608. In one embodiment, a portion of the proximal end of the output link 608 has a flat portion that results in a "D-shaped" configuration as described with respect to other components above, thereby resulting in the output link 608 and spur gear 606 being coupled such that they are not rotatable in relation to each other. A screw 610 is threadably coupled to the output link 608 and secures the spur gear 606 on the output link 608, along with the bearings 612, 614, while also translationally securing the output link 608. The bearings 612, 614 can constrain and support the output link 608 and are supported within the gear housing 602. The components are retained in the gear housing 602 with the help of the housing cover 616, which is secured to the housing 602 with the help of screws 618, which also apply a preload force through the gear housing cover 616. According to one embodiment, the screw 620 helps to secure an elastic band between the upper arm 530A and forearm 530B, as described above.

Figure 35:
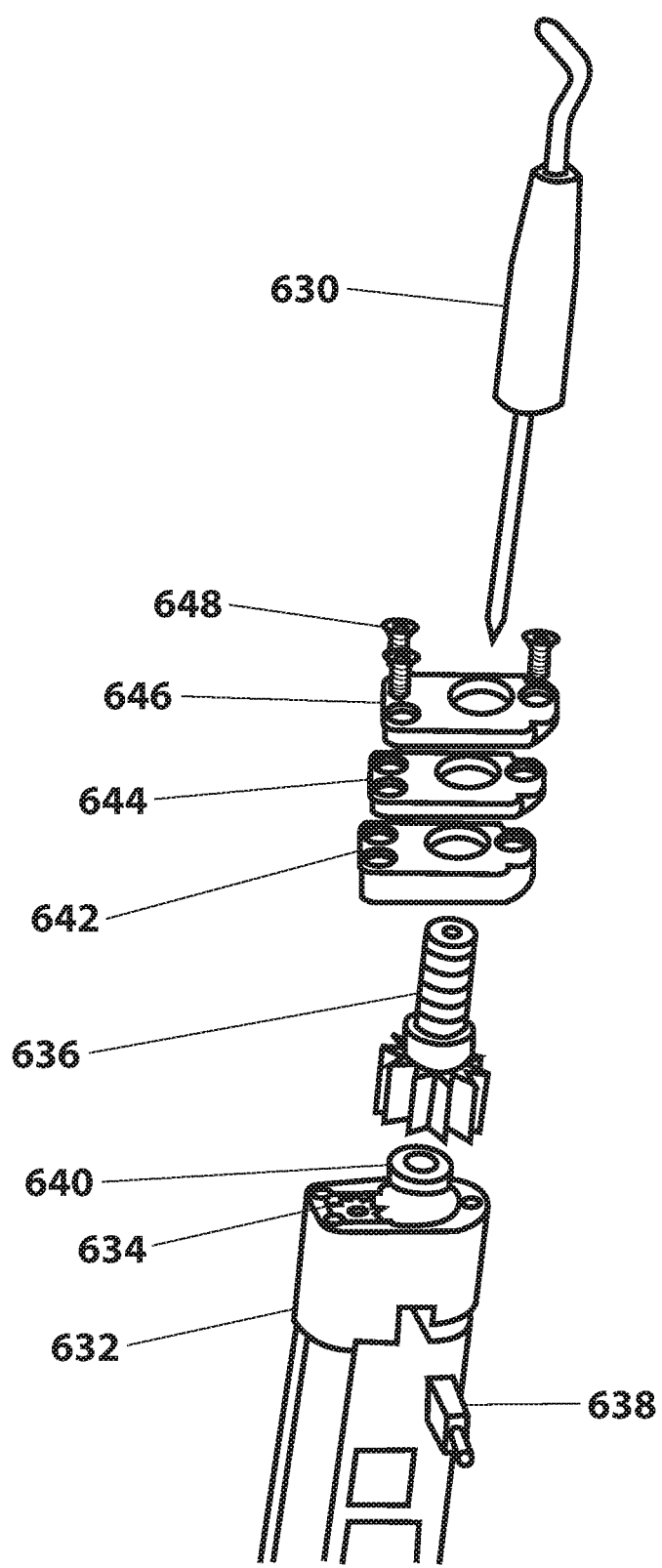
FIG. 35 is an exploded view of a forearm, according to one embodiment.

FIG. 35 depicts the forearm 530B and end effector 630 of the right arm 530. In this embodiment, the end effector 630 is another implementation of a monopolar electrocautery device 630. The forearm 530B has a motor housing 632 that is configured to hold the motor assembly (not shown) and also contains the slip ring 638, which is secured in the housing 632. It is understood that the motor assembly and associated drive train are substantially similar to the same components in the upper arm as described above.

The motor spur gear 634 is operably coupled to the driven spur gear 636 in the motor housing 632. The driven gear 636 is supported and constrained by bearing 640 and bushing 642, which prevents translation of the driven gear 636. The driven gear 636 is threadably coupled to the removable end effector 630 via the threads on the distal portion of the gear 636. The end effector 630 is electrically coupled to the slip ring 638.

In addition, according to one embodiment, the forearm 530B is fluidically sealed such that external fluids (such as body fluids, for example) are prevented from entering the internal portions of the forearm 530B. One component that helps to fluidically seal the forearm 530B is a gasket 644, which is positioned between the housing 632 and the housing cover 646 such that the screws 648 that secure the housing cover 646 to the housing 632 also secures the gasket 644 to the bushing 642. In one embodiment, the gasket 644 is made of soft urethane or silicon. Alternatively, the gasket 644 is made of any material that can help to fluidically seal the housing 632.

Figure 36:
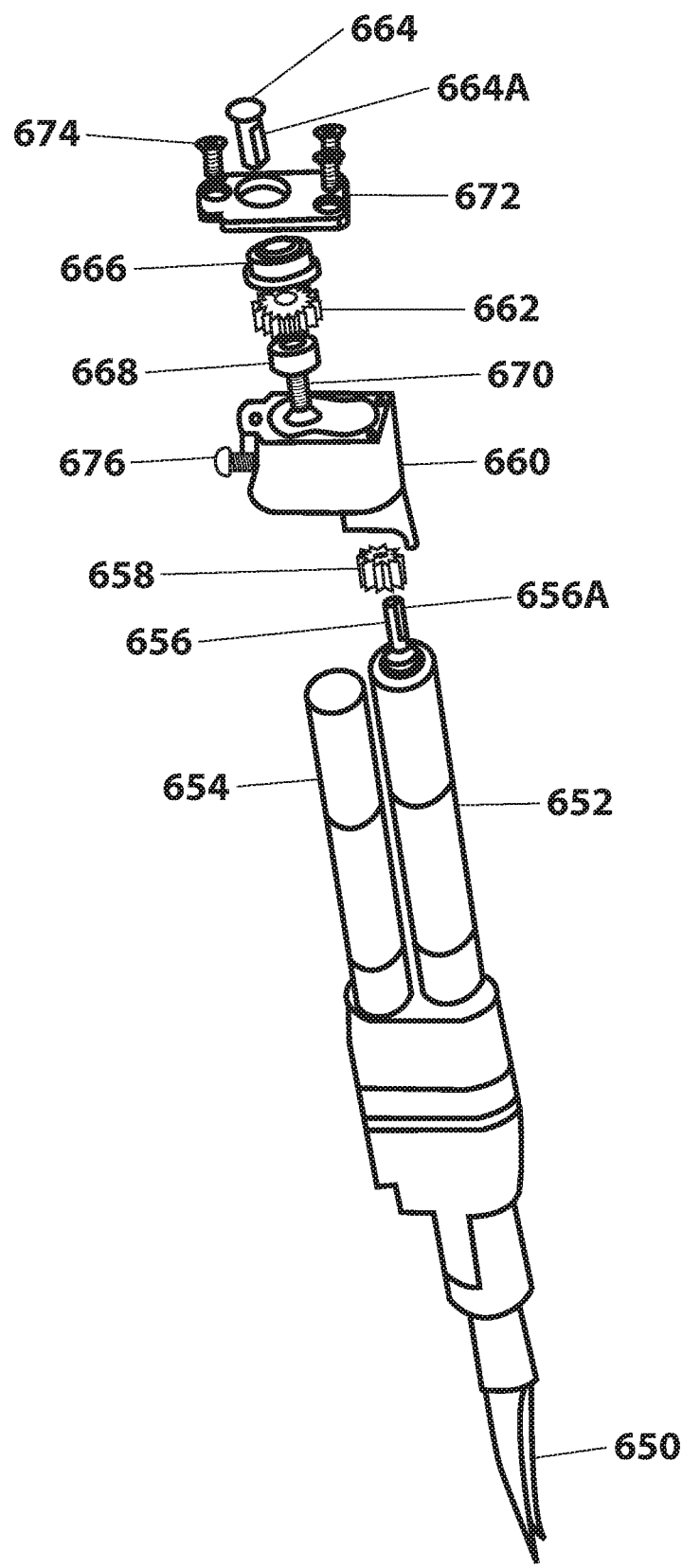
FIG. 36 is an exploded view of a forearm, according to one embodiment.
Figure 37:
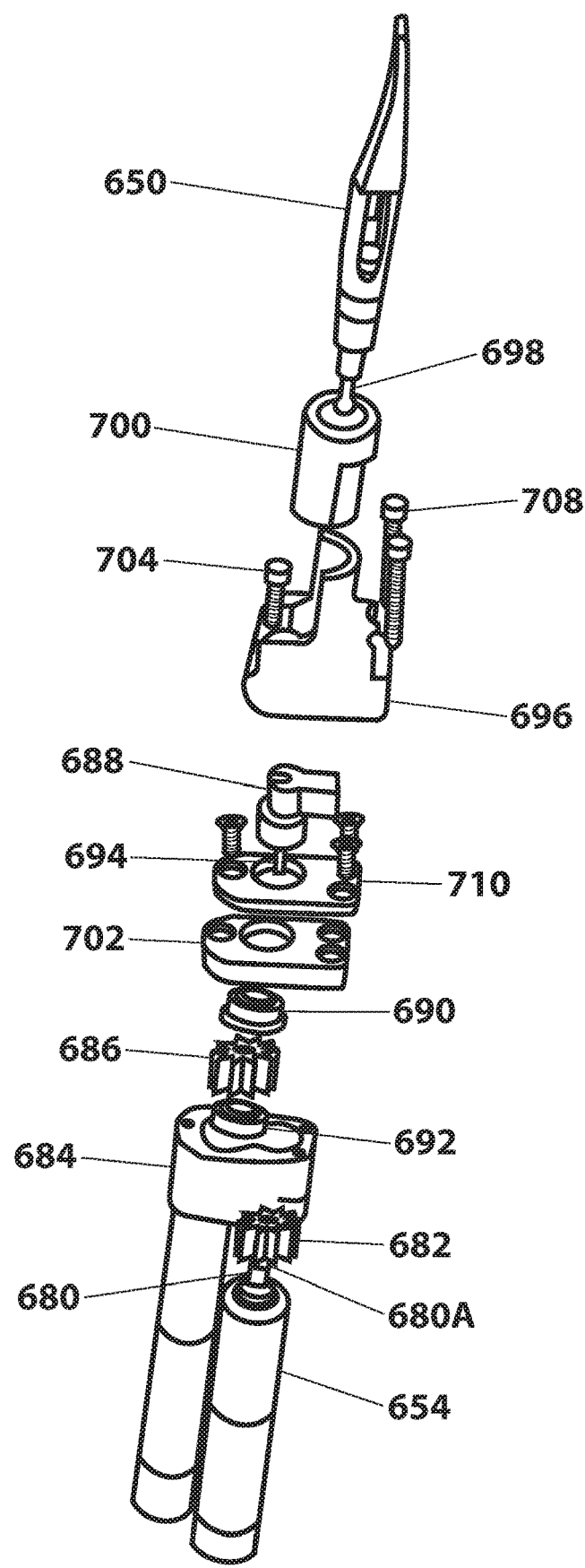
FIG. 37 is an exploded view of a forearm, according to one embodiment.

FIGS. 36-39B depict the forearm 520B and end effector 650 of the left arm 520. In this embodiment, the end effector 650 is another implementation of a grasper component (also referred to herein as a "tissue manipulation component" or "tissue manipulator") 650. As best shown in FIGS. 36 and 37, the forearm 520B has two motor assemblies: the rotation motor assembly 652 and the grasper motor assembly 654. As best shown in FIG. 36, the rotation motor assembly 652 can cause the forearm 520B to rotate. As best shown in FIG. 37, the grasper motor assembly 654 can cause the grasper 650 to move between its open and closed positions.

Returning to FIG. 36, in one embodiment, the rotation motor assembly 652 has a motor, an encoder, and an integrated gear head. Further, the assembly 652 has a motor shaft 656 that couples to the motor spur gear 658. According to one implementation, the shaft 656 has a flat portion 656A that results in the shaft 656 having a "D-shaped" configuration that mates with a "D-shaped" lumen defined in the spur gear 658. As such, the shaft 656 and gear 658 are coupled such that neither component can rotate in relation to the other. A portion of the motor assembly 652 and the motor spur gear 658 are positioned in the proximal gear housing 660, which also houses the driven spur gear 662 such that the motor spur gear 658 and driven spur gear 662 are rotatably coupled to each other when positioned in the housing 660. In one embodiment, the motor assembly 652 is coupled to the housing 660, and in certain implementations, the assembly 652 is geometrically and/or adhesively secured to the housing 660. Actuation of the motor assembly 652 causes rotation of the motor spur gear 658, which causes rotation of the driven spur gear 662.

The driven spur gear 662 is operably coupled to the output link 664, which is coupled to the upper arm 520A and thus is part of the joint between the upper arm 520A and forearm 520B. As shown in FIG. 36, the driven spur gear 662 and two bearings 666, 668 are positioned on the output link 664 such that the bearings 666, 668 are supported within the proximal gear housing 660 and provide some support and constraint to the output link 664. A screw 670 is coupled to the output link 664 and helps to secure the gear 662 and bearings 666, 668 to the link 664 while also translationally constraining the link 664. In one embodiment, the output link 664 has a flat portion 664A that creates a "D-shaped" configuration that mates with a D-shaped lumen defined in the driven spur gear 662 such that the gear 662 and link 664 cannot rotate in relation to each other when the gear 662 is positioned on the link 664.

The housing 660 also has a housing cover 672 that is positioned over the opening in the housing 660 that contains the gears 658, 662. The cover 672 is secured in place by screws 674 and thereby applies a preload force to the bearings 666, 668. The housing also has an additional screw 676 that can be used to secure or otherwise constrain an elastic band that is coupled to both the upper arm 520A and the forearm 520B to stabilize the arms as described above.

In one implementation, the housing 660 is configured to be fluidically sealed such that no liquid can gain access to any interior portions of the housing 660.

Returning to FIG. 37, in one embodiment, the grasper motor assembly 654 has a motor, an encoder, and an integrated gear head. Further, the assembly 654 has a motor shaft 680 that couples to the motor spur gear 682. According to one implementation, the shaft 680 has a flat portion 680A that results in the shaft 680 having a "D-shaped" configuration that mates with a "D-shaped" lumen defined in the spur gear 682. As such, the shaft 680 and gear 682 are coupled such that neither component can rotate in relation to the other. A portion of the motor assembly 654 and the motor spur gear 682 are positioned in the distal gear housing 684, which also houses the driven spur gear 686 such that the motor spur gear 682 and driven spur gear 686 are rotatably coupled to each other when positioned in the housing 684. In one embodiment, the motor assembly 654 is coupled to the housing 684, and in certain implementations, the assembly 654 is geometrically and/or adhesively secured to the housing 684. Actuation of the motor assembly 654 causes the grasper 650 to move between its open and closed positions, as described in detail below.

The driven spur gear 686 is operably coupled to a push/pull mate 688, which is coupled to the grasper 650. More specifically, the driven spur gear 686 and two bearings 690, 692 are positioned on a threaded rod 694 extending from the push/pull mate 688 such that the bearings 690, 692 are supported within the distal gear housing 684 and provide some support and constraint to the driven gear 686. The gear 686 is threadably coupled to the rod 694. A housing cover 702 is configured to cover the opening in the gear housing 684 and thereby applies a preloading force to bearings 690, 692 via screws 704, 708 that are threadably coupled through the cover 702 and into the housing 684. The housing 684 also has a gasket or seal 710 that fluidically seals against the push/pull mate 688, thereby preventing any fluids from entering the interior of the housing 684. In one embodiment, the seal 710 is made of soft urethane or silicon or any other known material for use in creating a fluidic seal.

Figure 38A:
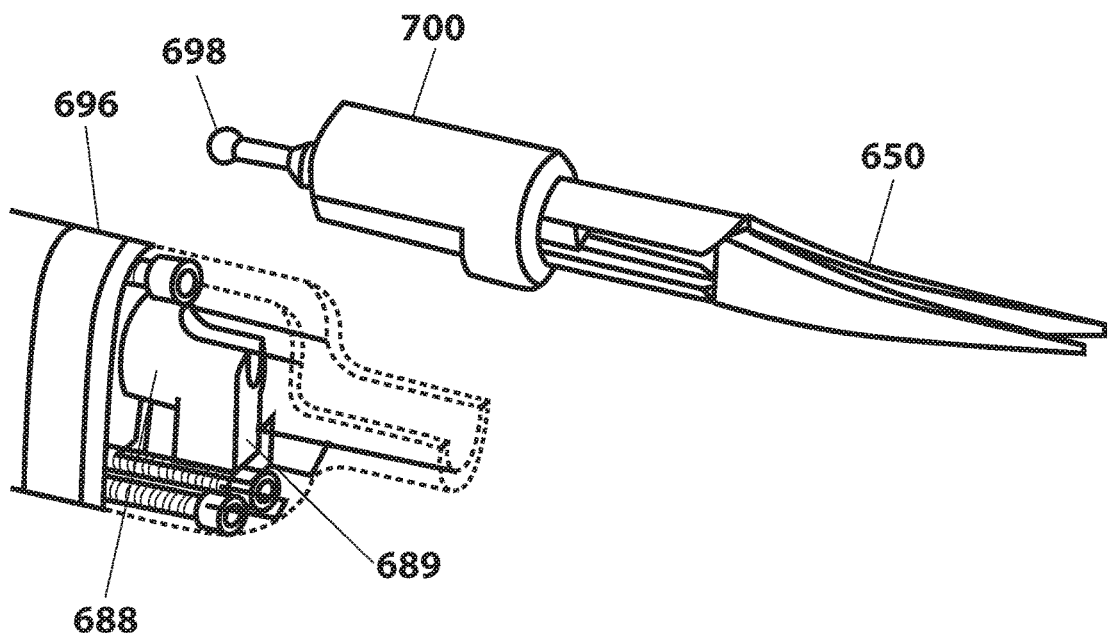
FIG. 38A is an expanded perspective view of a portion of the forearm of FIG. 37.
Figure 38B:
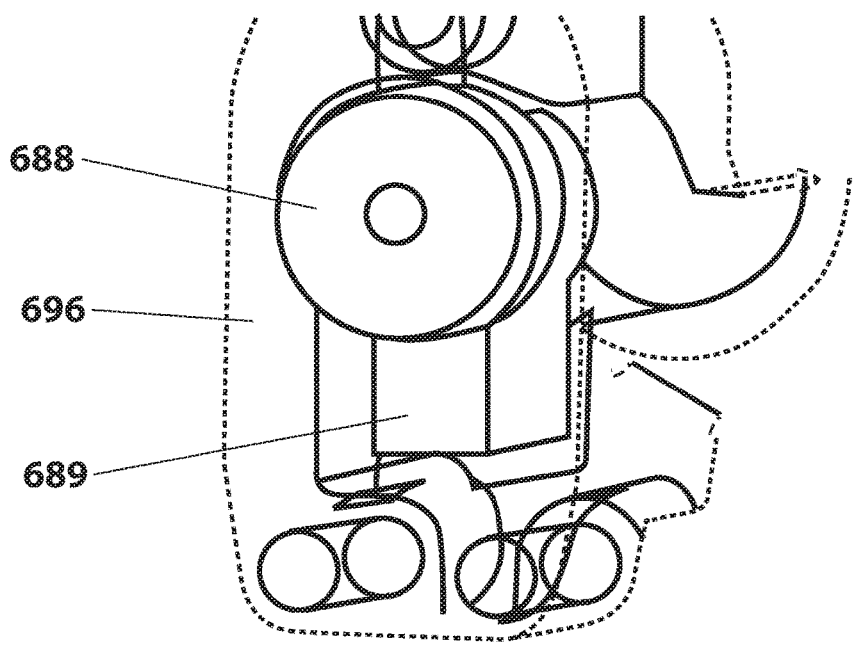
FIG. 38B is an expanded perspective view of a portion of the forearm of FIG. 37.

When the driven spur gear 686 rotates, the push/pull mate 688 translates, because the push/pull mate 688 is rotationally constrained to the grasper housing 696. More specifically, as best shown in FIGS. 38A and 38B, the push/pull mate 688 has a projection 689 that extends away from the push/pull mate 688 at 90 degrees in relation to the longitudinal axis of the forearm 520B. As such, the projection 689 is positioned in the housing 696 such that the push/pull mate 688 cannot rotate in relation to the housing 696.

Figure 39A:
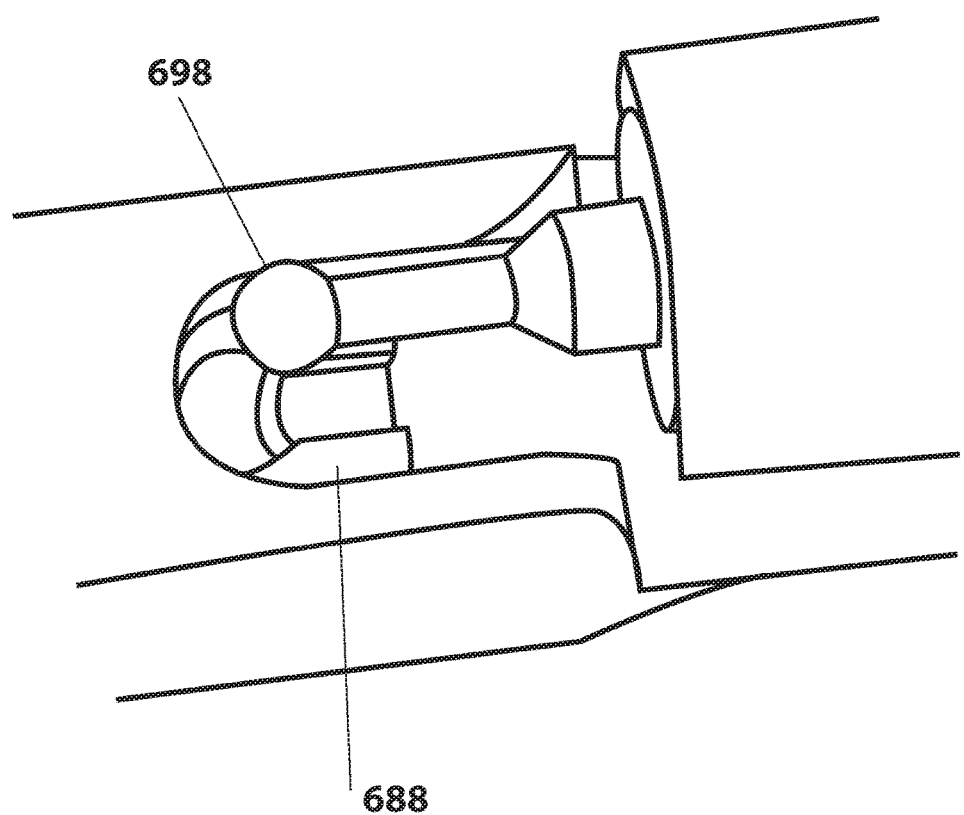
FIG. 39A is an expanded perspective view of a portion of the forearm of FIG. 37.

In one embodiment, as best shown in FIGS. 37, 38A, and 39A, the grasper 650 is removably coupled to the push/pull mate 688 via a ball and socket coupling, with the ball 698 positioned at a proximal end of the replaceable grasper 650. Through this coupling, the translational motion of the push/pull mate 688 is transferred to the grasper 650 jaws such that the jaws move between open and closed positions. The grasper 650 is geometrically and adhesively constrained to the grasper mate 700, which is geometrically constrained to the grasper housing 696.

Figure 39B:
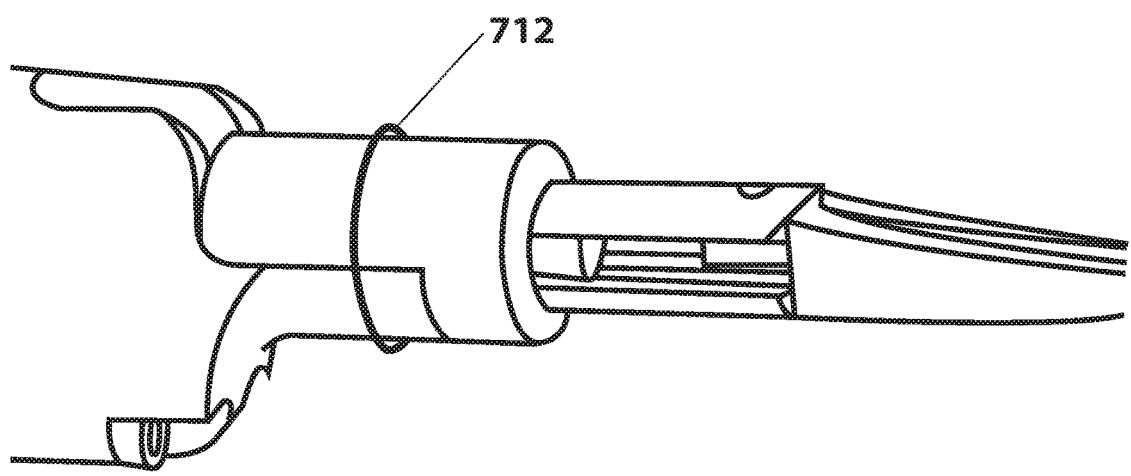
FIG. 39B is an expanded perspective view of a portion of the forearm of FIG. 37.

As best shown in FIGS. 38A, 39A, and 39B, the grasper 650 and the grasper mate 700 are configured to be removably mateable to the distal end of the grasper housing 696 and the push/pull mate 688 as described above. As such, the grasper 650 can be easily coupled for use and just as easily removed and replaced with another end effector. According to one implementation, the grasper end effector 650 could be replaced with other known manipulation devices such as, but not limited to, other toothed graspers, bipolar electrocautery devices, clip appliers, shears, ultrasonic sealers, or the like. When the grasper 650 (or other end effector) has been coupled to the grasper housing 696 and the push/pull mate 688 such that the ball 698 is positioned in the socket of the push/pull mate 688, the end effector 650 can be secured to the housing 696 with an elastic band 712 as shown in FIG. 39B. Alternatively, any other type of band or retention device or mechanism can be used.

The various in vivo robotic devices disclosed herein and other such devices are intended to be inserted into and positioned inside a cavity inside a patient, such as, for example, the peritoneal cavity. Various methods and devices can be used to achieve the insertion of the device into the cavity. FIGS. 40A-45 depict various embodiments of such insertion devices.

Figure 40A:
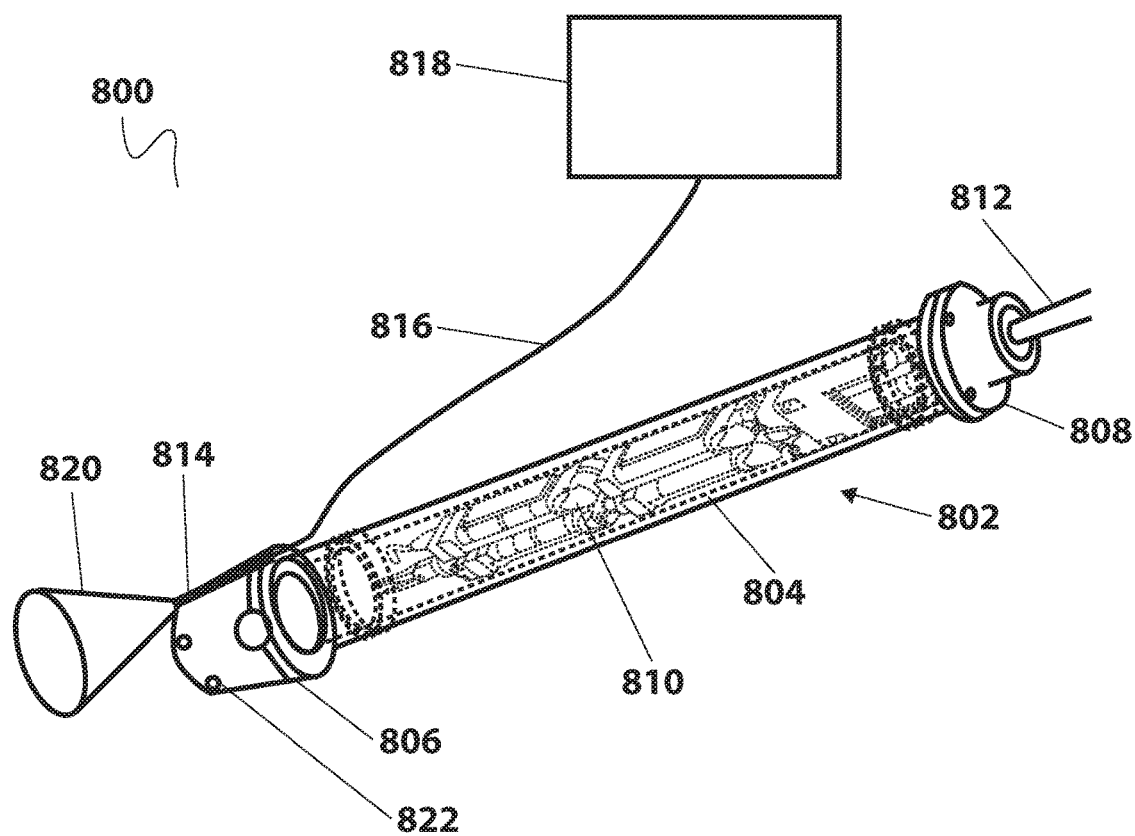
FIG. 40A is a perspective view of an access and insertion device, according to one embodiment.

FIGS. 40A, 41A, and 41B depict an insertion device 800 having an insertion tube 802 defining an insertion chamber 804, an insertion port 806, and a proximal tube cover 808. As shown in FIG. 40A, in use, a robotic device 810 (such as, for example, any of the device embodiments discussed above), can be positioned inside the insertion chamber 804 and coupled to an insertion rod 812 that is positioned through the proximal tube cover 808. The device 800 can be positioned against an incision in a patient that accesses the target cavity such that the insertion port 806 is positioned against or in the incision. Once the device 800 is correctly positioned, a user can use the insertion rod 812 to urge the device 810 out of the chamber 804 through the port 806 and into the patient's cavity.

Figures 1, 40B:
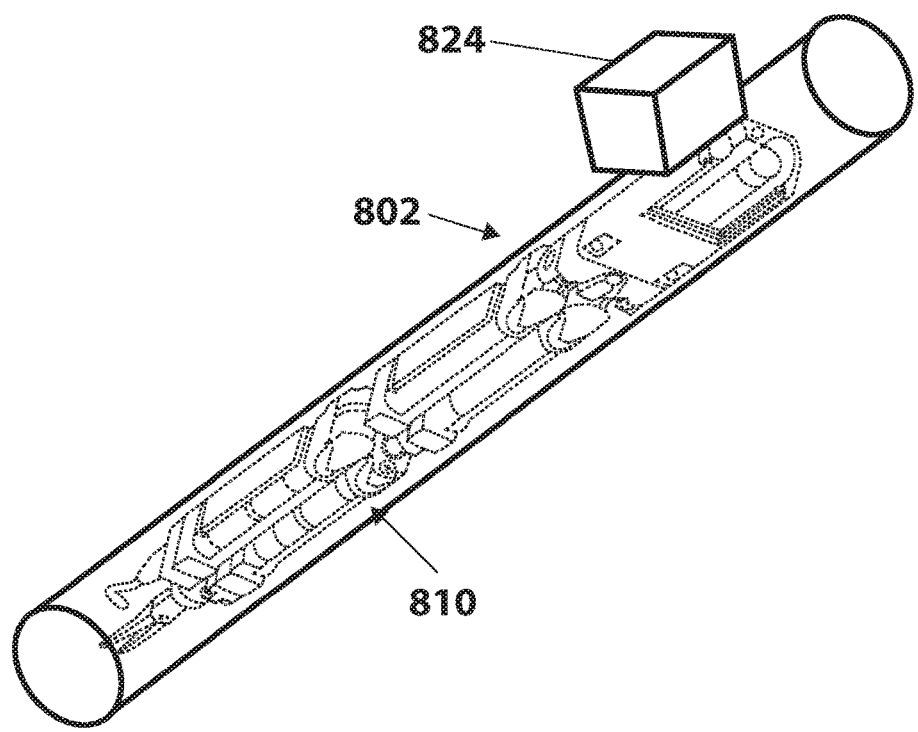
FIG. 40B-1 is a perspective view of an access and insertion device in use, according to one embodiment.
Figures 2, 40B:
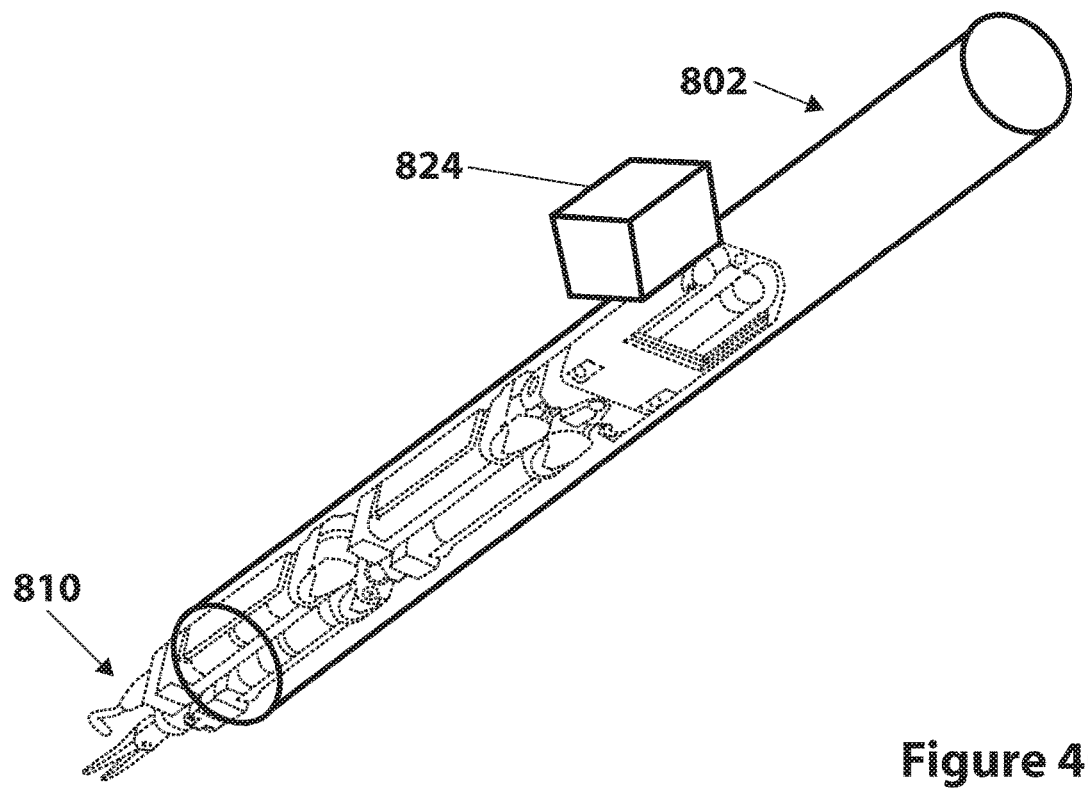
Figures 3, 40B:
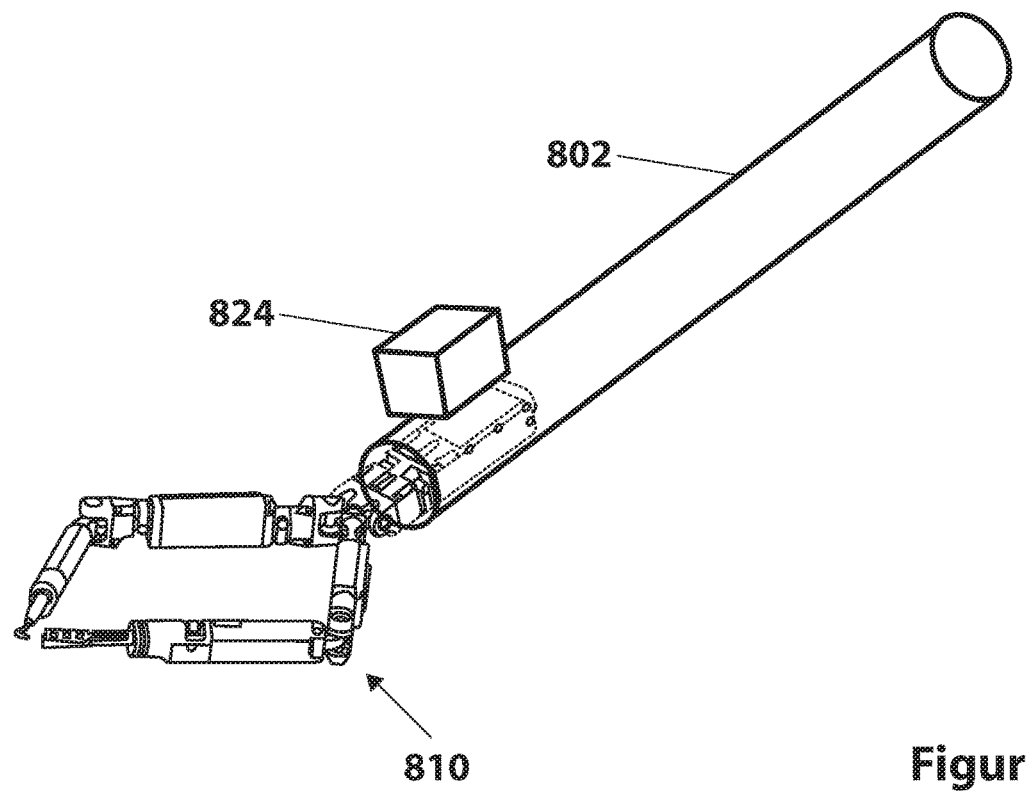
Figures 4, 40B:
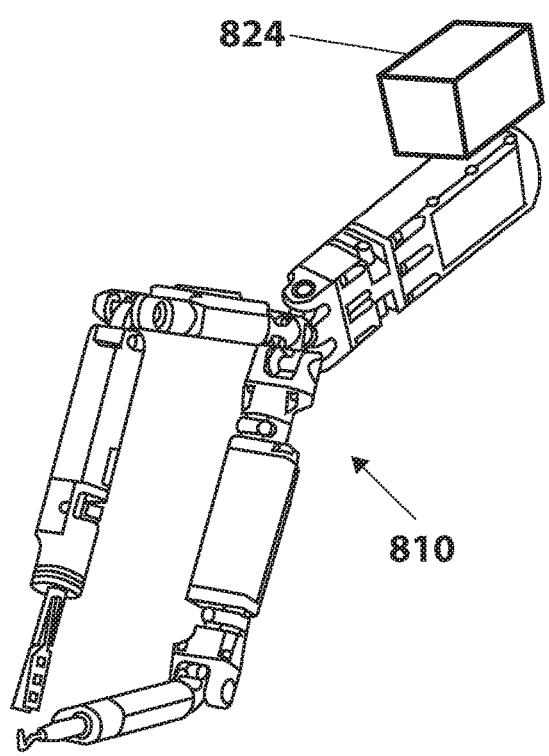

Alternatively, as best shown in FIG. 40B (including FIGS. 40B-1, 40B-2, 40B-3, and 40B-4), the robotic device 810 can be positioned inside the insertion tube 802 and magnetically coupled to a handle 824 positioned along an external portion of the tube 802 (as shown in FIG. 40B-1). According to some implementations, the handle 824 can be used to introduce the robotic device 810 into the abdominal cavity and secure the device 810 to the abdominal wall through a magnetic coupling. More specifically, once an opening is established between the chamber 804 and the patient's cavity, the handle 824 can be urged distally along the outer surface of the tube 802, thereby urging the device 810 via magnetic forces in a distal direction as well such that the device 810 is urged out of the distal end of the tube 802 as best shown in FIG. 40B-2. The handle 824 can then be urged to the end of the tube 802 such that the arms of the device 810 fully exit the chamber 804 as best shown in FIG. 40B-3 and further such that the entire device 810 exits the chamber 804 and is positioned in the cavity using the handle 824 (wherein the handle 824 is positioned outside the patient's body) as best shown in FIG. 40B-4. This insertion method can allow the orifice or insertion tube 802 to remain open for the duration of the surgical procedure. The orifice or insertion tube 802 can be used by other surgical devices as well, such as for specimen removal, for example. Furthermore, the magnetic coupling can allow the robotic device 810 to access a larger area of the abdominal cavity with different platform orientations. According to one embodiment, a channel could be created within the orifice or insertion tube 802 that can pass the communication and power tether to the robotic device 810.

According to one embodiment, the insertion tube 802 is comprised of a single rigid and/or flexible tubular structure. Alternatively, the tube 802 is not limited to a tubular configuration and could have any known shape that could contain a robotic device for insertion into a patient's cavity. For example, in one embodiment, the cross-section of the tube 802 could have a rectangular or oval shape.

In a further alternative, the insertion tube 802 can be flexible. In such an embodiment, once the insertion port 806 is secured to or otherwise coupled with the incision site, the flexible tube 802 (with the robotic device housed within) could be coupled to the port 806. At that point, the abdominal cavity is insufflated and the flexible tube 802 becomes semi-rigid as a result of the insufflation, like a balloon full of air. The robotic device is then inserted and, in one embodiment, the flexible tube 802 collapses at a point parallel to the coupling of the insertion rod to the device, reducing the external size of the tube 802. A pressure release valve would be needed to account for the change in volume.

Figure 42A:
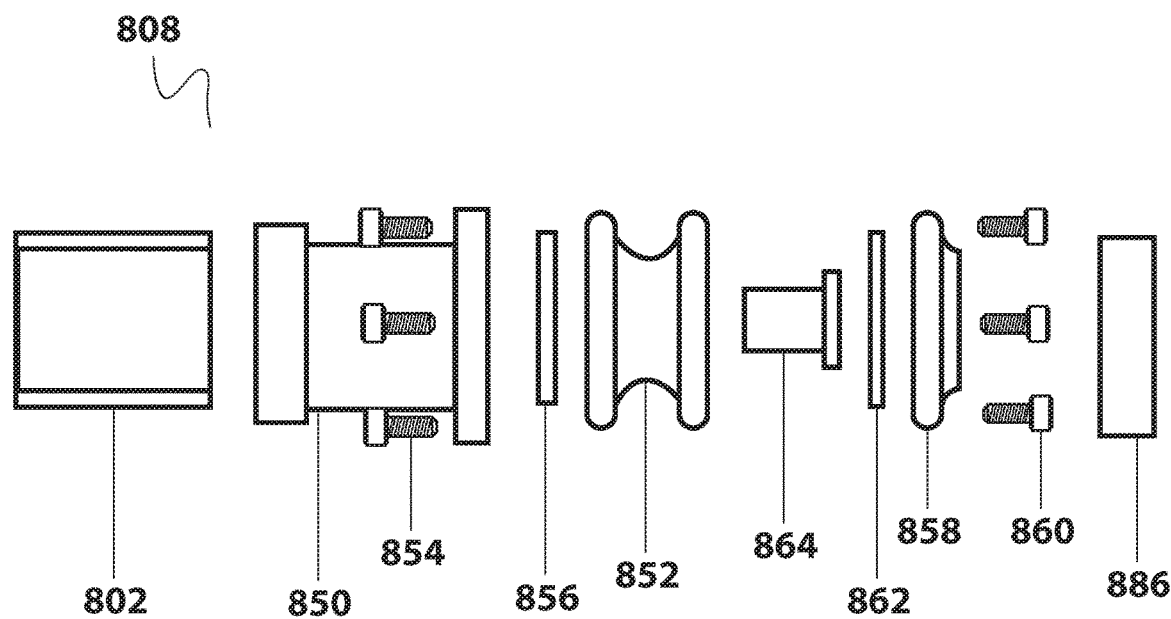
FIG. 42A is a exploded view of a portion of an access and insertion device, according to one embodiment.
Figure 42B:
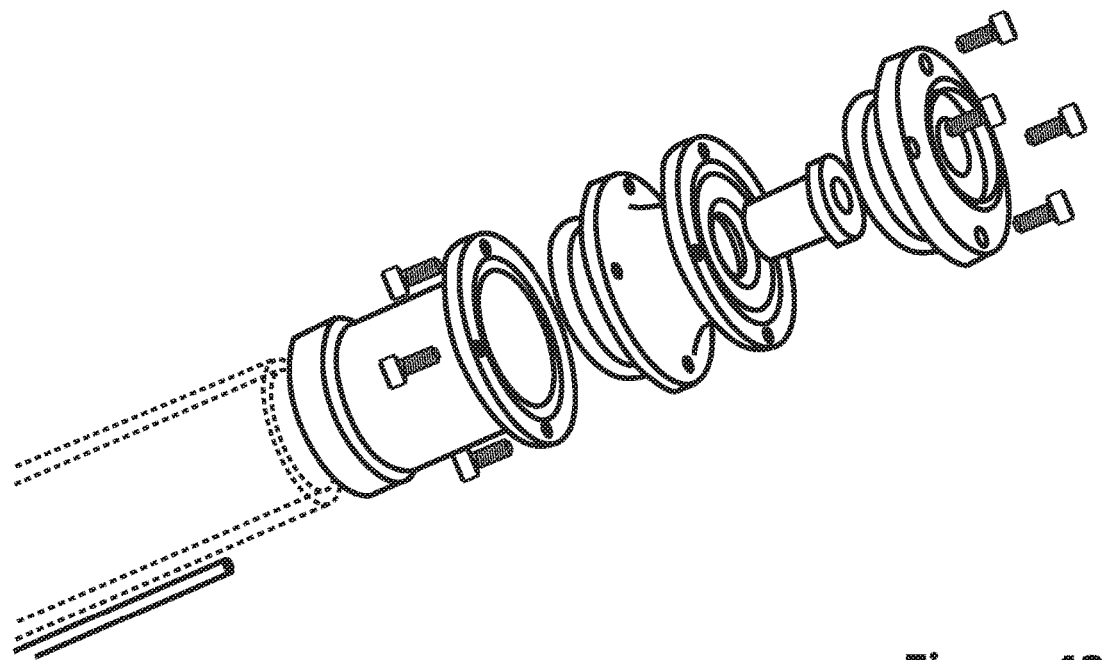
FIG. 42B is a perspective view of the portion of the access and insertion device of FIG. 42A.

FIGS. 42A and 42B depict one embodiment of the proximal tube cover 808. In this embodiment, the cover 808 has a tube mate 850 coupled to the insertion tube 802. In one embodiment, the tube mate 850 is geometrically and/or adhesively secured to the tube 802. The tube mate 850 is coupled at its opposite end to a housing 852. In this embodiment, the tube mate 850 and housing 852 are coupled with screws 854. Alternatively, any known coupling mechanisms or methods can be used. In one implementation, a gasket 856 is positioned between the tube mate 850 and housing 852. A bushing 864 is positioned in and secured to the housing 852. In accordance with one implementation, the bushing 864 can be mated with the insertion rod 812 described above such that the rod 812 can move longitudinally with smooth linear motion. The housing 852 is coupled to a seal cap 858 via screws 860, and a gasket 862 and a seal 866 are positioned between the housing 852 and cap 858. In one embodiment, the seal 866 creates a dynamic seal between the insertion rod 812 and the seal 866 to prevent the loss of insufflation of the abdominal cavity as the rod 812 is moved back and forth during a procedure.

Figure 43:
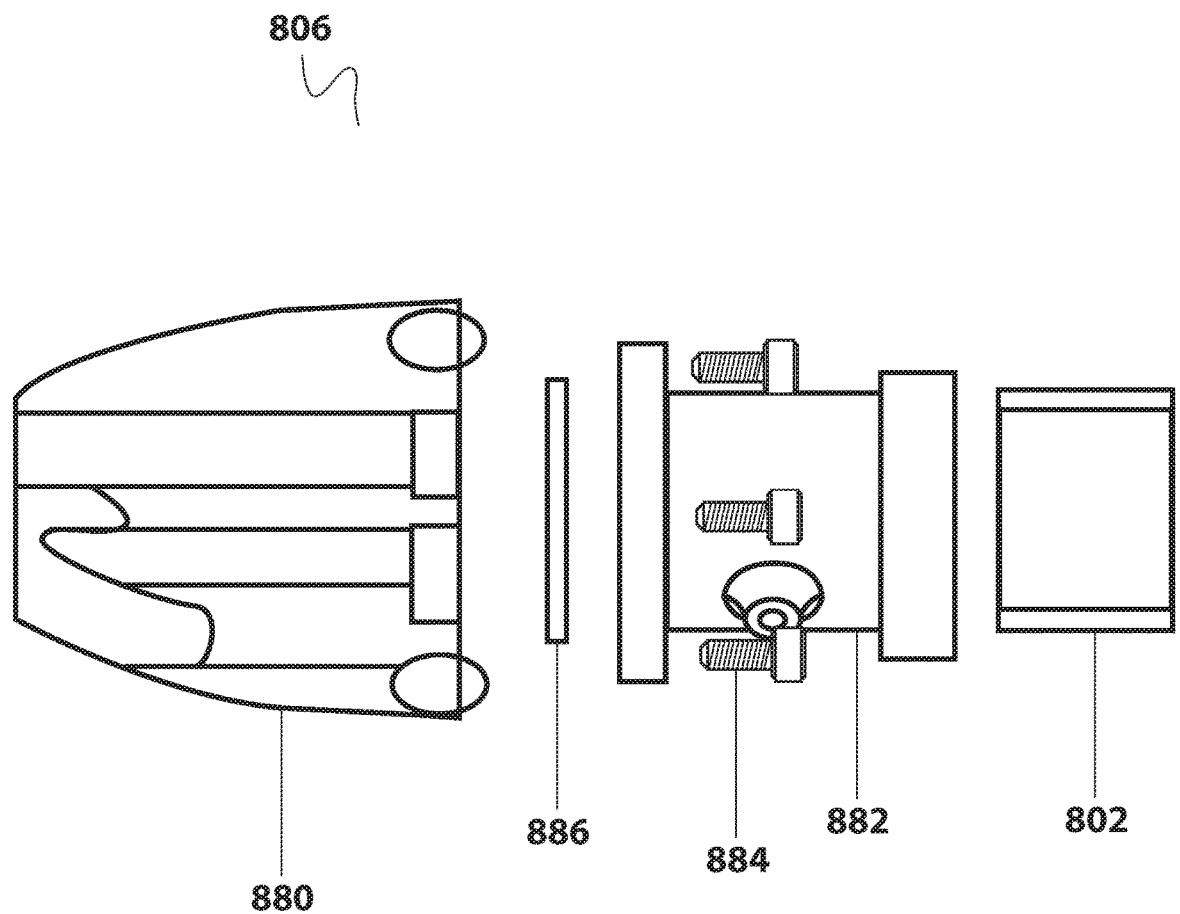
FIG. 43 is a side view of a portion of the access and insertion device of FIG. 42A.
Figure 44A:
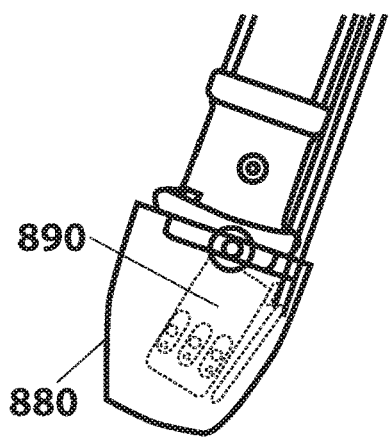
FIG. 44A is a perspective view of an access and insertion device in use, according to one embodiment.
Figure 44B:
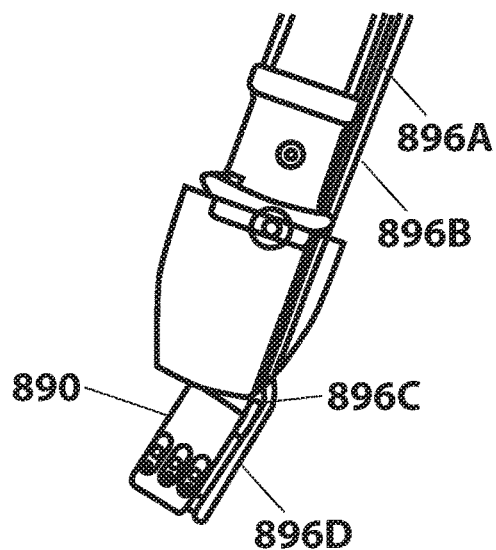
FIG. 44B is a perspective view of the access and insertion device of FIG. 44A in use.
Figure 44C:
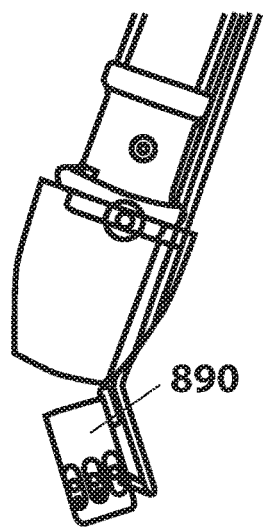
FIG. 44C is a perspective view of the access and insertion device of FIG. 44A in use.
Figure 44D:
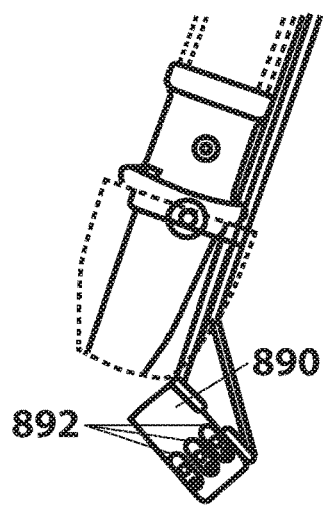
FIG. 44D is a perspective view of the access and insertion device of FIG. 44A in use.
Figure 44E:
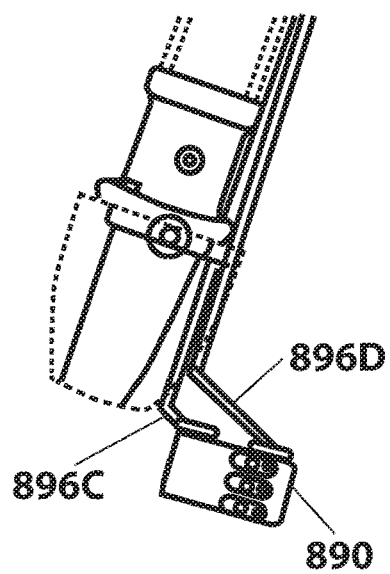
FIG. 44E is a perspective view of the access and insertion device of FIG. 44A in use.
Figure 44F:
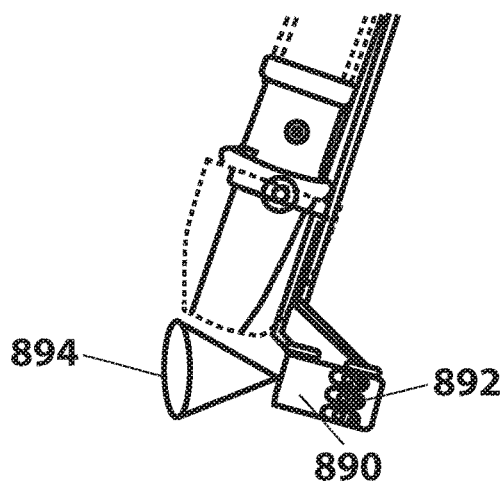
FIG. 44F is a perspective view of the access and insertion device of FIG. 44A in use.

FIG. 43 depicts one implementation of the insertion port 806. As shown, the port 806 includes a insertion cone 880 and a tube mate 882. The tube mate 882 is coupled to the insertion tube 802. The tube mate 882 can be geometrically and/or adhesively coupled to the tube 802. On the opposite end, the tube mate 882 is coupled to the insertion cone 880 with screws 884. In addition, a gasket 886 is positioned between the tube mate 882 and the insertion cone 880.

It is understood that the insertion cone 880 is not limited to conical geometry. That is, the insertion cone 880 could also have a tubular configuration or any other known configuration so long as the component could still operate as a port.

In certain alternative embodiments, any of the robotic devices disclosed or contemplated herein (including, for example, the robotic devices 8, 810) can be manually inserted into the abdominal cavity through the advancement of an insertion rod (such as, for example, the insertion rods 40, 812 described above) or a magnet. Alternatively, any such robotic device (such as robotic device 8, 810) can be robotically inserted into the abdominal cavity through the use of a robotic arm. In such an embodiment, the insertion procedure could be performed by the surgeon or autonomously. It is understood that the robotic devices such as devices 8, 810 have a "sweet spot" or robotic workspace volume with high dexterity and manipulability. The use of a robotic arm can expand this workspace volume such that the volume includes the entire abdominal cavity. According to another implementation, a "soft boundary" can be created between the workspace boundary, or limits, and the "sweet spot" of the workspace. That is, if the device crosses the soft boundary, the system has a sensor or other mechanism that is triggered such that the system actuates the external robotic arm to automatically and/or autonomously grossly position the robotic device back to the "sweet spot" of the workspace. Such repositioning operation can also be done manually or robotically under surgeon supervision. Autonomous gross positioning could eliminate the bed side assistant and human errors that commonly occur between the surgeon and assistant relating to positioning of the robotic device.

Various embodiments of the insertion device 800 can have cameras (also referred to herein as "visualization devices"). The camera embodiments disclosed herein allow the user to view the device during insertion into and use in the patient's cavity.

Returning to FIG. 40A, in one embodiment, a camera 814 is housed within the insertion port 806. According to one embodiment, the camera 814 is a 3 MM CMOS camera 814. The vision cone 820 (the area captured by the camera 814 such that a user can see that area on the display) achieved by the camera 814 is shown. In one embodiment, the camera 814 is coupled to a connection component 816 that couples the camera 814 to a monitor 818 or other type of display. Light, in this embodiment, is provided by LED lights 822 positioned on the distal end of the insertion port 806. Alternatively, any known lights that can be used with a medical device to illuminate a surgical space for viewing with a camera can be used.

FIGS. 44A-44F depict another embodiment of a camera 890 for use with certain embodiments of the insertion device 800. The camera 890 has lights 892 coupled to the camera 890. In this embodiment, the camera 890 is coupled to the device 800 with a four-bar linkage 896 made up of four bars (or "links") 896A, 896B, 896C, 896D. That is, the four bars 896A, 896B, 896C, 896D can be manipulated by a user to move the camera 890 out of the cone 880 and position it to view the robotic device during insertion and use as shown in the figures. The vision cone 894 provides a schematic depiction of the area captured by the camera 890 in one embodiment. This configuration allows for a larger camera (such as, for example, a high definition camera) to be housed in the insertion cone 880 prior to insertion of the device (when the device is not positioned in or through the cone 880) and then moved out of the cone 880 during use. That is, once the port 806 is attached to the incision site and the cavity is insufflated, the camera 890 can be deployed via the four-bar linkage 896. This positioning of the camera in the cone 880 and then moving it out of the cone allows for the robotic device to always be under visualization during insertion.

In a further alternative, any other known actuation device or mechanism could be used to deploy the camera. One such further example is a preformed shape memory alloy or the like.

In one embodiment, the camera 890 is a USB webcam.

Figure 45A:
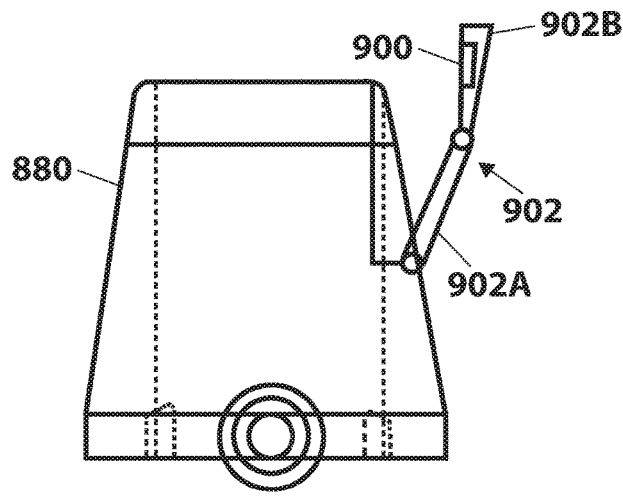
FIG. 45A is a side view of a portion of an access and insertion device, according to one embodiment.
Figure 45B:
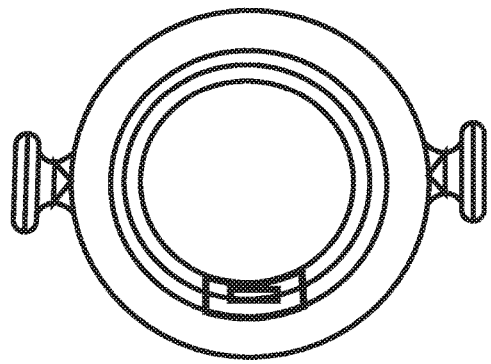
FIG. 45B is a cross-section view of the portion of the access and insertion device of FIG. 45A.
Figure 45C:
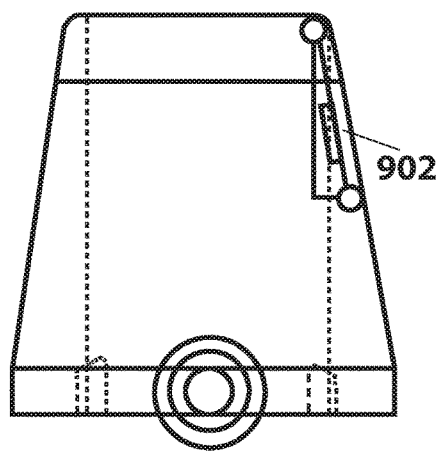
FIG. 45C is a side view of the portion of the access and insertion device of FIG. 45A.
Figure 45D:
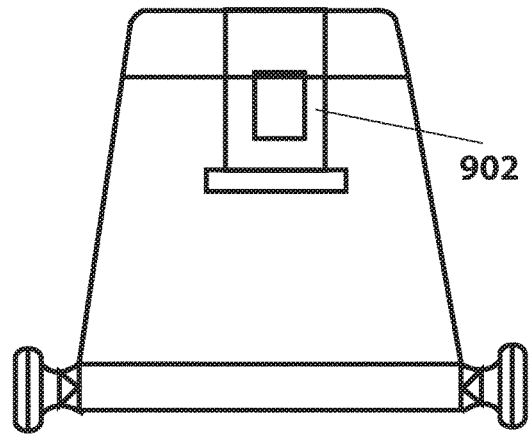
FIG. 45D is a side view of the portion of the access and insertion device of FIG. 45A.

FIGS. 45A-45D depict yet another camera implementation. In this embodiment, the camera 900 is coupled to a linkage 902 that is coupled to an exterior portion of the insertion cone 880. More specifically, the linkage 902 is made up of two links 902A, 902B, and the camera 900 is coupled to the link 902B. The link 902A is pivotally coupled to the insertion cone 880, and the link 902B is pivotally coupled to the link 902A. In an undeployed configuration as shown in FIGS. 45B, 45C, and 45D, the links 902A, 902B are configured such that the camera 900 and links 902A, 902B form a portion of the cone 880. In the deployed configuration as shown in FIG. 45A, the links 902A, 902B are extended so that the camera 900 is in a position to capture images of the surgical area. The lights (not shown) can be coupled to the link 902B or link 902A (or both) to illuminate the viewing area.

It is understood that any of the camera embodiments disclosed above can also have a zoom lens package or mechanical translation parallel to the axis of the vision cone via a linear actuator.

Although the present invention has been described with reference to preferred embodiments, persons skilled in the art will recognize that changes may be made in form and detail without departing from the spirit and scope of the invention.

What is claimed is:

1. A robotic device, comprising:
   (a) an elongate device body configured to be positioned at least partially within a body cavity of a patient through an incision, the device body comprising:
      (i) a first housing comprising a first motor and a second motor; and
      (ii) a second housing disposed at a distal end of the device body, the second housing comprising:
         (A) a first shoulder joint positioned at a distal end of the second housing, the first shoulder joint operably coupled to the first motor; and
         (B) a second shoulder joint positioned at the distal end of the second housing, the second shoulder joint operably coupled to the second motor;
   (b) a first arm operably coupled to the first shoulder joint, wherein the first arm is positioned substantially within a longitudinal cross-section of the device body when the first arm is extended in a straight configuration, the first arm comprising:
      (i) a first upper arm segment comprising a first arm motor;
      (ii) a first forearm segment; and
      (iii) a first end effector; and
   (c) a second arm operably coupled to the second shoulder joint, wherein the second arm is positioned substantially within the longitudinal cross-section of the device body when the second arm is extended in a straight configuration, the second arm comprising:
      (i) a second upper arm segment comprising a second arm motor;
      (ii) a second forearm segment; and
      (iii) a second end effector.

2. The robotic device of claim 1, wherein the second housing comprises first, second, and third housing protrusions disposed at the distal end of the second housing, wherein the first shoulder joint is disposed between the first and second housing protrusions and the second shoulder joint is disposed between the second and third housing protrusions.

3. The robotic device of claim 1, wherein the first and second shoulder joints are positioned substantially within the longitudinal cross-section of the device body.

4. The robotic device of claim 1, wherein the first shoulder joint comprises a first gear, wherein the first arm is operably coupled to the first gear.

5. The robotic device of claim 4, wherein the first gear is configured to rotate around a first axis parallel to a length of the device body.

6. The robotic device of claim 4, wherein the second shoulder joint comprises a second gear, wherein the second arm is operably coupled to the second gear.

7. The robotic device of claim 6, wherein the second gear is configured to rotate around a second axis parallel to a length of the device body.

8. The robotic device of claim 6, wherein the first gear comprises a tooth-free portion and the second gear comprises a tooth-free portion.

9. The robotic device of claim 1, wherein the first upper arm segment and the first forearm segment are collinear when the first arm is extended in the straight configuration.

10. The robotic device of claim 9, wherein the second upper arm segment and the second forearm segment are collinear when the second arm is extended in the straight configuration.

11. The robotic device of claim 1, wherein the first arm motor is operably coupled to a first local control board and the second arm motor is operably coupled to a second local control board.

12. A robotic device, comprising:
   (a) an elongate device body configured to be positioned at least partially within a body cavity of a patient through an incision, the device body comprising:
      (i) a first shoulder joint positioned at a distal end of the device body, the first shoulder joint configured to rotate around a first axis parallel to a length of the device body; and
      (ii) a second shoulder joint positioned at the distal end of the device body, the second shoulder joint configured to rotate around a second axis parallel to the length of the device body;
   (b) a first arm operably coupled to the first shoulder joint, wherein the first shoulder joint is positioned substantially within a longitudinal cross-section of the device body, the first arm comprising:
      (i) a first upper arm segment comprising a first arm motor;
      (ii) a first forearm segment; and
      (iii) a first end effector; and
   (c) a second arm operably coupled to the second shoulder joint, wherein the second shoulder joint is positioned substantially within the longitudinal cross-section of the device body, the second arm comprising:
      (i) a second upper arm segment comprising a second arm motor;
      (ii) a second forearm segment; and
      (iii) a second end effector.

13. The robotic device of claim 12, wherein the first arm is positioned substantially within the longitudinal cross-section of the device body when the first arm is extended in a straight configuration.

14. The robotic device of claim 12, wherein the second arm is positioned substantially within the longitudinal cross-section of the device body when the second arm is extended in a straight configuration.

15. The robotic device of claim 12, wherein the first upper arm segment and the first forearm segment are collinear when the first arm is extended in a straight configuration.

16. The robotic device of claim 12, wherein the second upper arm segment and the second forearm segment are collinear when the second arm is extended in a straight configuration.

17. The robotic device of claim 12, wherein the first shoulder joint comprises a first gear comprising a tooth-free portion and the second shoulder joint comprises a second gear comprising a tooth-free portion.

18. A robotic device, comprising:
（a) an elongate device body configured to be positioned at least partially within a body cavity of a patient through an incision, the device body comprising:
  (i) a motor housing comprising a first motor and a second motor; and
  (ii) a shoulder joint housing disposed at a distal end of the device body, the shoulder joint housing comprising:
    (A) a first shoulder joint positioned at a distal end of the shoulder joint housing, the first shoulder joint operably coupled to the first motor, wherein the first shoulder joint is positioned to rotate around a first axis parallel to a length of the device body; and
    (B) a second shoulder joint positioned at the distal end of the shoulder joint housing, the second shoulder joint operably coupled to the second motor, wherein the second shoulder joint is positioned to rotate around a second axis parallel to the length of the device body; and
（b) a first arm operably coupled to the first shoulder joint, the first arm comprising a first upper arm, a first forearm, and a first end effector, wherein the first arm is positioned substantially within a longitudinal cross-section of the device body when the first arm is extended in a straight configuration such that the first upper arm and the first forearm are collinear, the first upper arm comprising a first arm motor; and
（c) a second arm operably coupled to the second shoulder joint, the second arm comprising a second upper arm, a second forearm, and a second end effector, wherein the second arm is positioned substantially within the longitudinal cross-section of the device body when the second arm is extended in a straight configuration such that the second upper arm and the second forearm are collinear, the second upper arm comprising a second arm motor.

19. The robotic device of claim 18, wherein the first shoulder joint comprises a first gear, wherein the first arm is operably coupled to the first gear.

20. The robotic device of claim 19, wherein the second shoulder joint comprises a second gear, wherein the second arm is operably coupled to the second gear.

* * * * *